(12) United States Patent
Onishi et al.

(10) Patent No.: US 6,636,254 B1
(45) Date of Patent: *Oct. 21, 2003

(54) IMAGE PROCESSING APPARATUS FOR PERFORMING TURN OR MIRROR INVERSION ON AN INPUT VIDEO SIGNAL AND OUTPUTTING DIFFERENT IMAGES SIMULTANEOUSLY

(75) Inventors: Junichi Onishi, Hachioji (JP); Akihiro Taguchi, Hachioji (JP); Kenji Harano, Hachioji (JP); Akinobu Uchikubo, Ome (JP); Kenya Inomata, Mitaka (JP); Makoto Tsunakawa, Chofu (JP); Kuniaki Kami, Machida (JP); Tsutomu Hirai, Hachioji (JP); Takashi Takemura, Hachioji (JP); Mamoru Kaneko, Hannou (JP); Yasukazu Tatsumi, Hino (JP); Kyou Imagawa, Hachioji (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1054 days.

(21) Appl. No.: 08/754,203

(22) Filed: Nov. 20, 1996

Related U.S. Application Data

(63) Continuation of application No. 08/351,063, filed on Nov. 28, 1994, now abandoned.

(30) Foreign Application Priority Data

| Nov. 29, 1993 | (JP) | 5-298515 |
| Dec. 28, 1993 | (JP) | 5-334585 |
| Apr. 1, 1994 | (JP) | 6-65198 |
| Jul. 1, 1994 | (JP) | 6-151350 |

(51) Int. Cl.$^7$ ............................ H04N 7/18
(52) U.S. Cl. ................................ 348/65
(58) Field of Search ........................ 348/65, 66, 72, 348/77, 73, 74, 126, 564, 583, 589; 345/126; 600/117, 118, 167; H04N 7/18

(56) References Cited

U.S. PATENT DOCUMENTS

| 3,755,812 A | 8/1973 | Bechtel et al. |
| 4,869,237 A | * 9/1989 | Eino et al. .................... 348/65 |

(List continued on next page.)

FOREIGN PATENT DOCUMENTS

| EP | 0 174 698 | 3/1986 |
| EP | 0 211 783 | 2/1987 |
| FR | 2 605 825 | 4/1988 |

(List continued on next page.)

Primary Examiner—Richard Lee
(74) Attorney, Agent, or Firm—Armstrong, Westerman & Hattori, LLP.

(57) ABSTRACT

Using an endoscope system, a surgeon A holds an endoscope with a TV camera (hereinafter, an endoscope) and a therapeutic appliance such as forceps and carries out a surgical procedure while viewing a first monitor. A surgeon B holds a therapeutic appliance such as forceps and carries out the surgical procedure while viewing a second monitor. A video signal sent from the TV camera of the endoscope is fed to and processed by an image processing apparatus, and displayed on each of the first and second monitors. The image processing apparatus transfers the video signal sent from the endoscope to each of an image inverting circuit and a selector switch. The image inverting circuit inverts an image (laterally (to produce a mirror image), vertically, or vertically and laterally (180°)), and supplies a processed video signal to the selector switch. The selector switch selects a video signal to be supplied to each of the first and second monitors, which are display units, in response to a control signal sent from a selector. The contents of processing to be performed by the image inverting circuit and the video signal to be selected by the selector are designated using setting switches on an operation panel.

23 Claims, 64 Drawing Sheets

U.S. PATENT DOCUMENTS

| | | | | |
|---|---|---|---|---|
| 4,890,159 A | * | 12/1989 | Ogiu | 348/72 |
| 5,045,935 A | * | 9/1991 | Kikuchi | 348/71 |
| 5,093,653 A | * | 3/1992 | Ikehira | 345/126 |
| 5,126,847 A | | 6/1992 | Kori et al. | |
| 5,196,928 A | * | 3/1993 | Karasawa et al. | 348/65 |

FOREIGN PATENT DOCUMENTS

| | | |
|---|---|---|
| GB | 2 073 988 | 10/1981 |
| JP | 2-68027 | 3/1990 |
| JP | 5 153 485 | 6/1993 |
| JP | 5 215 970 | 8/1993 |

* cited by examiner

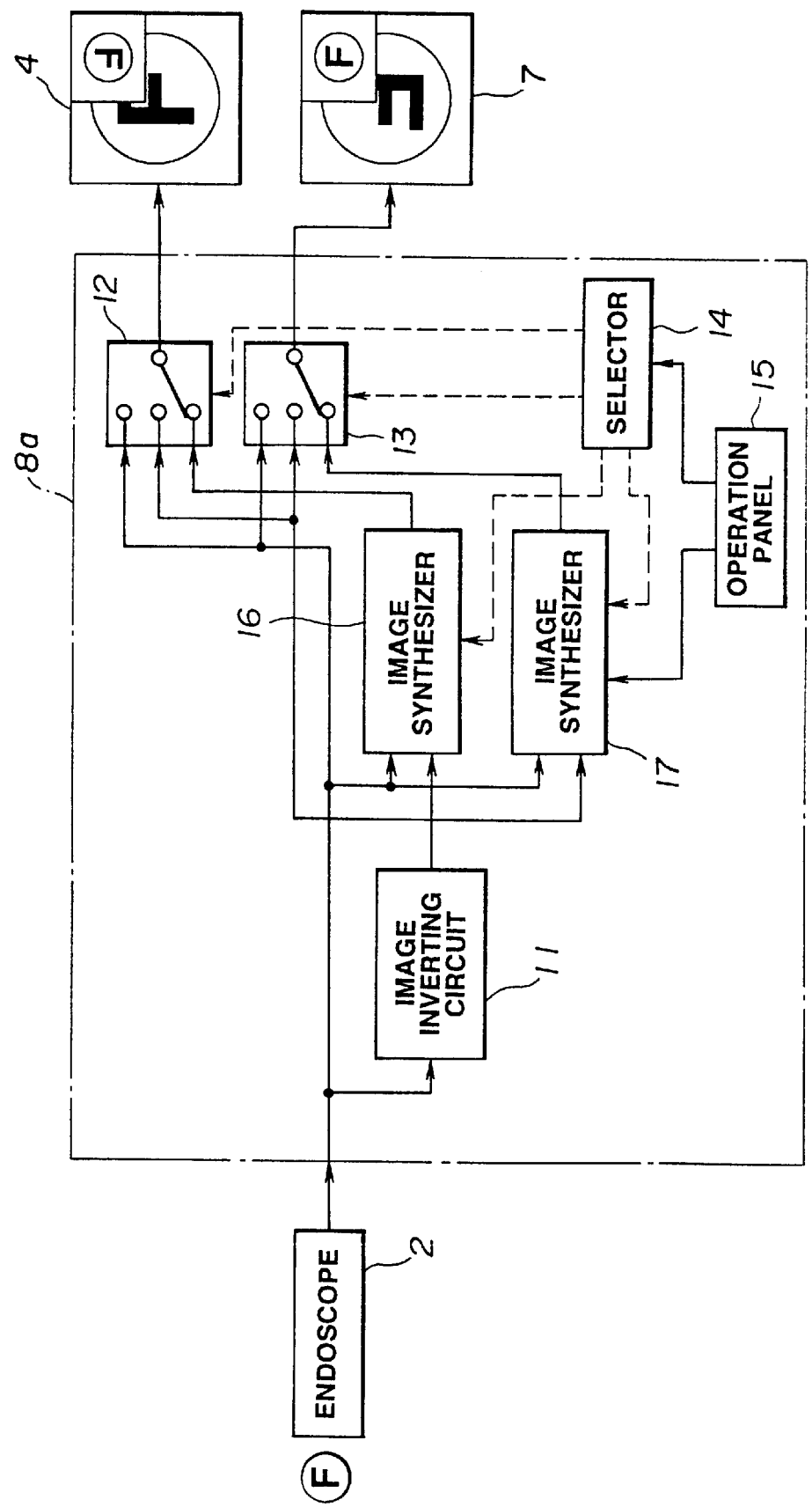

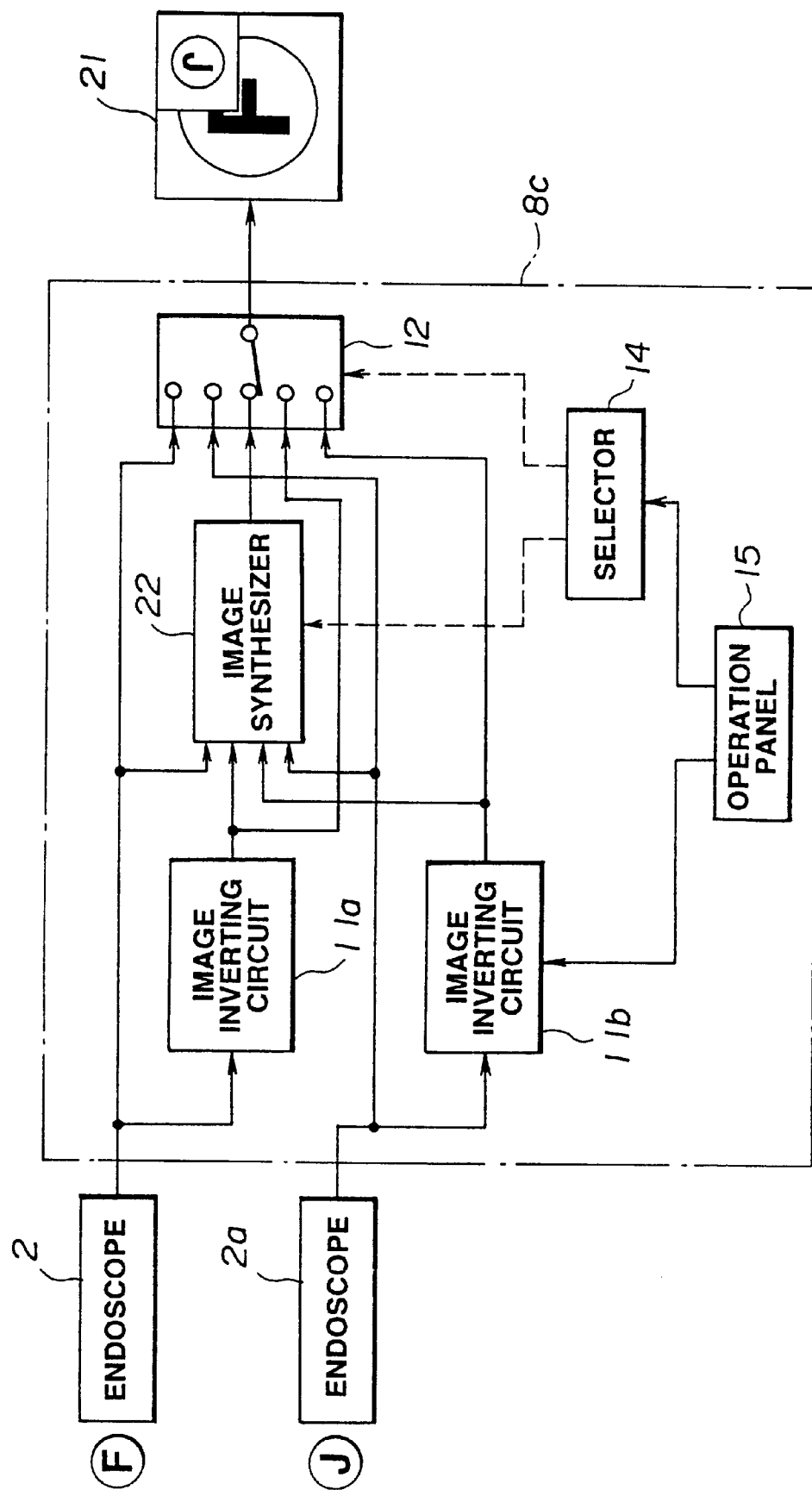

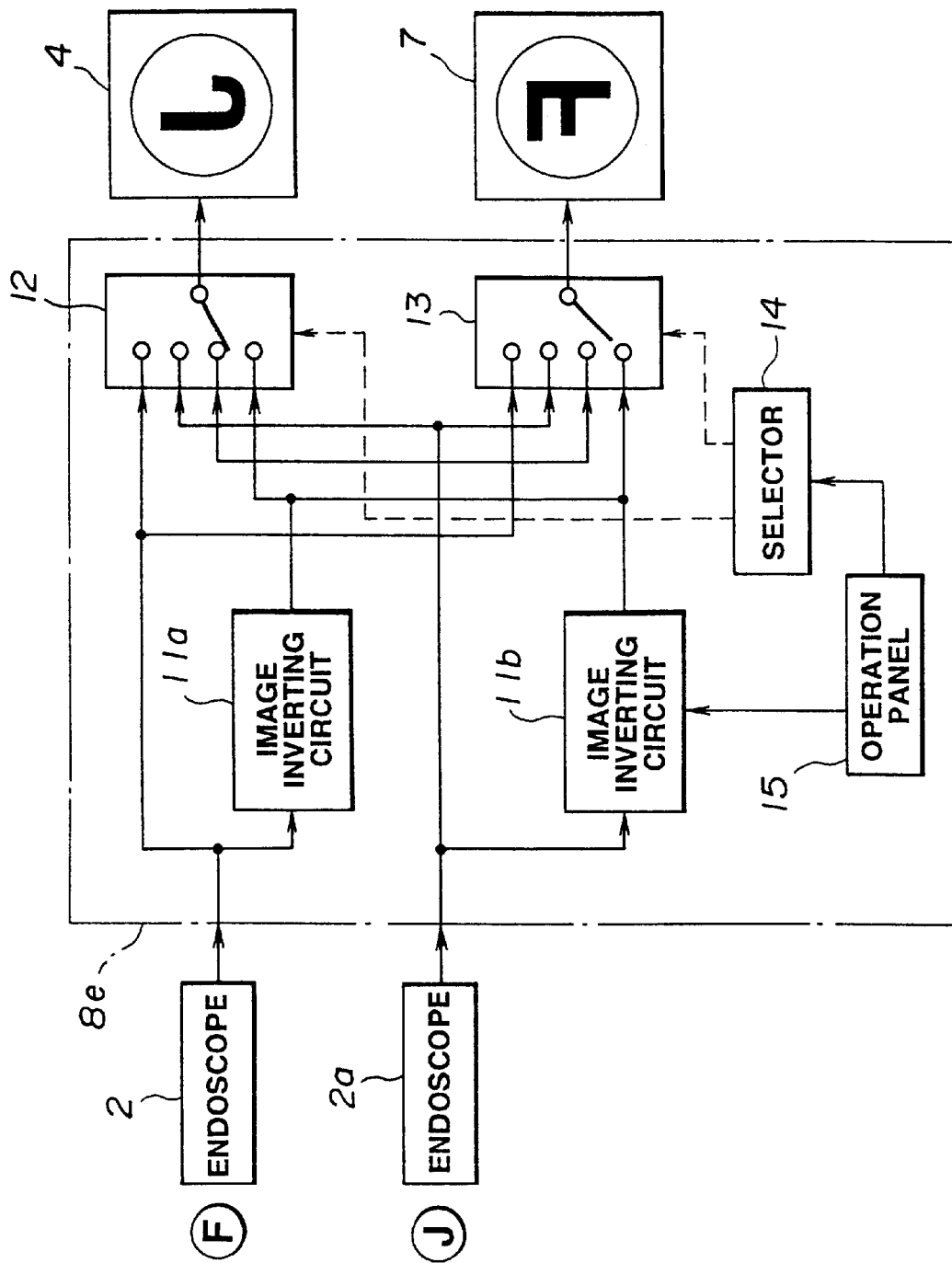

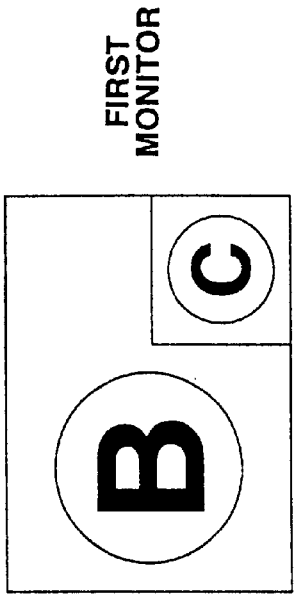
FIG.25A — WHEN INS IS NOT PRESSED:
FIG.25C — WHEN INS IS PRESSED:
FIG.25E — WHEN INS AND MIRR ARE PRESSED: FIRST MONITOR
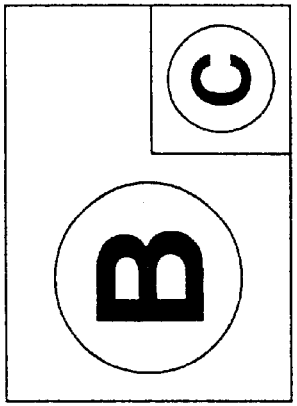
FIG.25B
FIG.25D — SECOND MONITOR
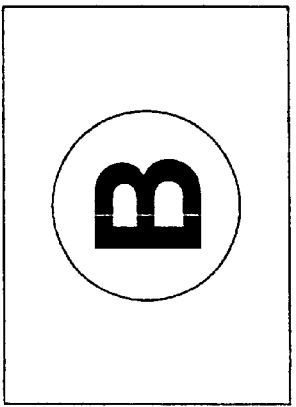

FIG.27A  FIG.27B
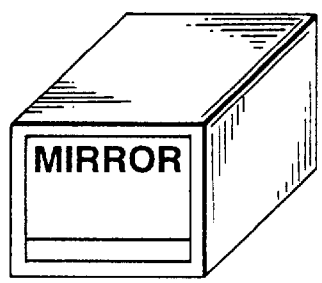
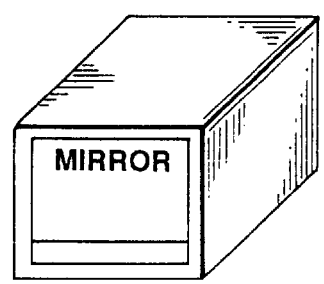
FIG.28
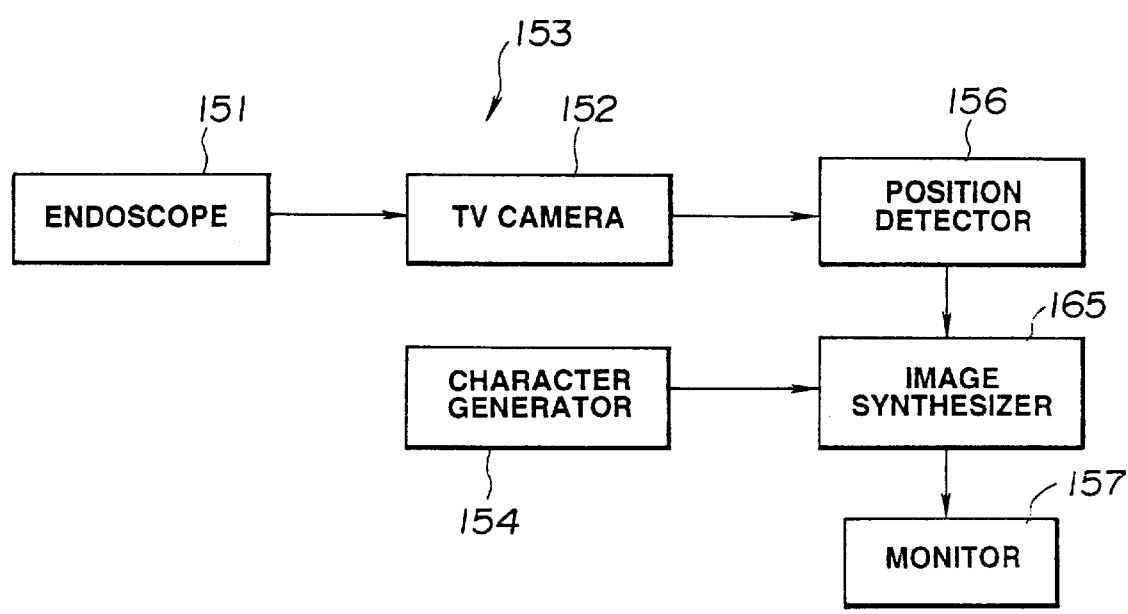

IMAGE PROCESSING APPARATUS FOR PERFORMING TURN OR MIRROR INVERSION ON AN INPUT VIDEO SIGNAL AND OUTPUTTING DIFFERENT IMAGES SIMULTANEOUSLY

This application is a continuation of application Ser. No. 08/351,063, filed Nov. 28, 1994, now abandoned.

BACKGROUND OF THE INVENTION

1. Field of the Invention

The present invention relates to an image processing apparatus for performing image processing on an input video signal.

2. Description of the Related Art

Conventionally, when the inferior cholecyst is enucleated under laparoscopic observation or any other surgical procedure is conducted under endoscopic observation, the lesion is treated using a therapeutic appliance with the help of endoscopic images of the lesion appearing on a TV monitor.

However, it is impossible to grasp the movement or position of forceps or the like in a region outside a field of view which cannot be covered by an endoscope. A positional relationship of a therapeutic appliance with a lesion cannot therefore be understood, thus hindering efficient surgical procedures.

During an endoscope-aided surgical procedure, a surgeon and an assistant stand with an operation table between them. The surgeon and assistant carries out the procedure while viewing monitors located on the opposite sides of them.

However, as long as the surgeon (assistant) facing an endoscope is concerned, his/her right and left hands are inverse to the right and left hands of an endoscopic image. The surgeon (assistant) therefore has difficulty in conducting the procedure.

As shown in FIG. 75, a surgeon A and a surgeon B are opposed to each other with a patient between them. The surgeon A inserts therapeutic appliances 502 and 503 as well as an endoscope 501 with a TV camera (hereinafter, referred to merely as an endoscope) using a trocar and cannula. Assuming that a lesion 506 in a body cavity has the positional relationships as shown in FIG. 76 with the endoscope 501 as well as the therapeutic appliances 502, 503, 504, and 505, an image produced by the endoscope 501 appears as shown in FIG. 77 on a monitor.

When the surgeon B tries to move the therapeutic appliance 505 in a direction indicated with a dotted line in a screen on the monitor shown in FIG. 77 in an attempt to bring the therapeutic appliance 505 close to the lesion, if the surgeon B operates the therapeutic appliance 505 while viewing the monitor, the therapeutic appliance 505 actually moves in a direction indicated with a solid line. The same applies to the therapeutic appliance 504. That is to say, the surgeon B finds positional relationships in the screen on the monitor laterally inverse to the actual ones.

For the surgeon B, an image made by laterally inverting the image on the monitor shown in FIG. 77 (hereinafter, referred to as a mirror image) looks natural and helpful in manipulating therapeutic appliances.

Likewise, in the situation shown in FIG. 75, when the lesion 506 in a body cavity has the positional relationships as shown in FIG. 78 with the endoscope 501 as well as the therapeutic appliances 502, 503, 504, and 505; that is, when the endoscope 501 images the lesion 506 from obliquely upward, an image provided by the endoscope appears as shown in FIG. 79 in a screen on the monitor. In this case, the surgeon B finds the image on the monitor inverse not only laterally but also vertically.

For the surgeon B, an image made by inverting the image shown in FIG. 79 laterally and vertically; that is, by 180° (hereinafter, referred to as an inverted image) looks natural and helpful in manipulating therapeutic appliances.

A conceivable measurement against the foregoing problem is to hang a monitor on a ceiling upside down.

However, when a monitor is placed upside down but not in a normal direction of installation, a problem occurs in terms of durability of the monitor and of electrical safety.

The foregoing drawback that an endoscopic image on a monitor looks laterally and vertically inverse for an observer (surgeon or assistant) occurs only when the observer is opposed to the endoscope. When the view direction of an endoscope changes during surgery, if the orientations of the observer and endoscope become consistent, the monitor must be returned to the normal direction. It is, however, impossible to take time for such cumbersome work in practice; that is, during surgery.

For endoscope-aided surgery, as disclosed in Japanese Patent Laid-Open No.2-68027, two images such as a radiographic image and an endoscopic image may be displayed as a synthetic image on a monitor using a picture-in-picture imaging means or the like.

The picture-in-picture imaging means is adaptable for a endoscope-aided surgical procedure during which a plurality of endoscopes are employed. When a plurality of endoscopes are employed, a surgeon and an assistant are required to manipulate different endoscopes and proceed with the procedure in cooperation and harmony. For a smoother procedure, it is therefore necessary to display an image provided by one's own endoscope as well as an image provided by a partner's endoscope using the picture-in-picture imaging means or the like. In this case, when the partner's endoscope is opposed to the one's own, the aforesaid lateral and vertical inversion occurs.

SUMMARY OF THE INVENTION

An object of the present invention is to provide an image processing apparatus for providing images whose view directions are found consistent by a plurality of observers during a surgical procedure or examination under endoscopic observation and for enabling display of an image provided by a partner's endoscope for confirmation.

Another object of the present invention is to provide an image processing apparatus for efficiently displaying and recording a desired image signal by supplying a plurality of kinds of image signals selectively to a plurality of output channels.

An image processing apparatus of the present invention comprises an image processing means for processing at least one of raw images fed to an image input means so as to produce at least one kind of transformed image; a turned image or a mirror image, and an image output means for simultaneously outputting at least different images among the transformed image produced by the image processing means and the raw images fed to the image input means.

Other features and advantages of the present invention will be fully apparent from the description below.

BRIEF DESCRIPTION OF THE DRAWINGS

FIG. 1 shows a configuration of an endoscope system having an image processing apparatus;

FIG. 2 shows a configuration of the image processing apparatus shown in FIG. 1;

FIG. 3 is an explanatory diagram showing schematically images appearing on the monitors shown in FIG. 1;

FIGS. 4 and 5F relate to the second embodiment of the present invention;

FIG. 4 shows a configuration of an image processing apparatus;

FIG. 5F is the sixth explanatory diagram schematically showing an image processed by the image processing apparatus shown in FIG. 4;

FIGS. 6 to 8 relate to the third embodiment of the present invention;

FIG. 6 shows a configuration of an endoscope system having an image processing apparatus;

FIG. 8 is an explanatory diagram schematically showing an image appearing on the monitor shown in FIG. 6;

FIGS. 9 to 12F relate to the fourth embodiment of the present invention;

FIG. 9 shows a configuration of an endoscope system having an image processing apparatus;

FIG. 10 shows a configuration of the image processing apparatus shown in FIG. 9;

FIG. 12F is the fifth diagram showing an example of a display in the image processing apparatus shown in FIG. 12A;

FIGS. 13 and 14 relate to the fifth embodiment of the present invention;

FIG. 13 shows a configuration of an endoscope system having an image processing apparatus;

FIG. 14 shows a configuration of the image processing apparatus shown in FIG. 13;

FIG. 15A shows a configuration of an image processing apparatus;

FIG. 15B is the first diagram showing an example of a display in the image processing apparatus shown in FIG. 15A;

FIG. 15C is the second diagram showing an example of a display in the image processing apparatus shown in FIG. 15A;

FIG. 16 shows a configuration of an endoscope system having an image processing apparatus;

FIG. 17 shows a configuration of the image processing apparatus shown in FIG. 16;

FIGS. 18 to 21B relate to the eighth embodiment of the present invention;

FIG. 18 is a schematic block diagram showing an image processing apparatus;

FIG. 19 is a block diagram also showing an image processing apparatus;

FIG. 20 is a front view showing a selector switch:

FIG. 21B is the second explanatory diagram showing a display screen on a monitor;

FIG. 22 is a block diagram showing a major portion of a image processing apparatus;

FIG. 23B is the second explanatory diagram showing an example of a display on a monitor provided by the image processing apparatus shown in FIG. 22;

FIGS. 24 and 25E relate to the tenth embodiment of the present invention;

FIG. 24 shows an overall configuration of an image processing apparatus;

FIGS. 25A is the first explanatory diagram showing an example of a display on a monitor;

FIG. 25B is the second explanatory diagram showing an example of a display on a monitor;

FIG. 25C is the third explanatory diagram showing an example of a display on a monitor;

FIG. 25D is the fourth explanatory diagram showing an example of a display on a monitor;

FIG. 25E is the fifth explanatory diagram showing an example of a display on a monitor;

FIG. 26A is a block diagram also showing a major portion of an image processing apparatus;

FIG. 26B shows an example of a display on a monitor in the image processing apparatus shown in FIG. 26A;

FIGS. 27A and 27B relate to the first variant of the eleventh embodiment;

FIG. 27A is the first explanatory diagram showing a display screen on a monitor;

FIG. 27B is the second explanatory diagram showing a display screen on a monitor;

FIGS. 28 and 29 relate to the second variant of the eleventh embodiment;

FIG. 28 shows a configuration of an image processing apparatus;

FIG. 33A is an explanatory diagram showing a screen display on a monitor;

FIG. 33B shows character data to be superposed on the screen shown in FIG. 33A;

FIG. 35 shows a configuration of an endoscope system;

FIG. 36 is an explanatory diagram concerning the display of a mirror image of a lesion provided by the endoscope system shown in FIG. 35;

FIGS. 37 to 39B relate to the eighteenth embodiment of the present invention;

FIG. 37 shows a configuration of an endoscope system;

FIG. 38 is an explanatory diagram concerning the operation of the delay circuit shown in FIG. 37;

FIG. 39B is the second explanatory diagram concerning the operation of a variant of the delay circuit shown in FIG. 37;

FIG. 40 shows a configuration of an endoscope system;

FIG. 41 shows a structure of a distal part of an endoscope;

FIG. 42 shows an overall configuration of an endoscopic image processing apparatus;

FIG. 43 is a schematic block diagram also showing an image processing apparatus;

FIG. 44 is a circuit diagram showing the circuitry of the image processing apparatus;

FIG. 45 is an explanatory diagram concerning a combination of displays of the first and second monitors;

FIG. 46 is a front view showing a selector switch;

FIGS. 48 to 51 relate to the twenty-second embodiment of the present invention;

FIG. 48 shows an overall configuration of an image processing apparatus;

FIG. 49 is a schematic block diagram also showing an image processing apparatus;

FIG. 51 is an enlarged view showing the front of a selector switch;

FIG. 52 shows an overall configuration of an image processing apparatus;

FIG. 53 is a circuit diagram showing the circuitry of an image processing apparatus;

FIG. 54 is an enlarged view showing the front of a selector switch;

FIG. 55 is a circuit diagram showing the circuitry of an image processing apparatus;

FIG. 56 is an enlarged view showing the front of a selector switch;

FIG. 57 is an enlarged view showing the front of a selector switch;

FIG. 58 is an explanatory diagram concerning examples of displays on monitors provided by the image processing apparatus shown in FIG. 57;

FIG. 59 shows a configuration of an image processing apparatus;

FIG. 60J is the tenth explanatory diagram showing an example of a display on a monitor provided by the image processing apparatus shown in FIG. 59;

Figure 61:
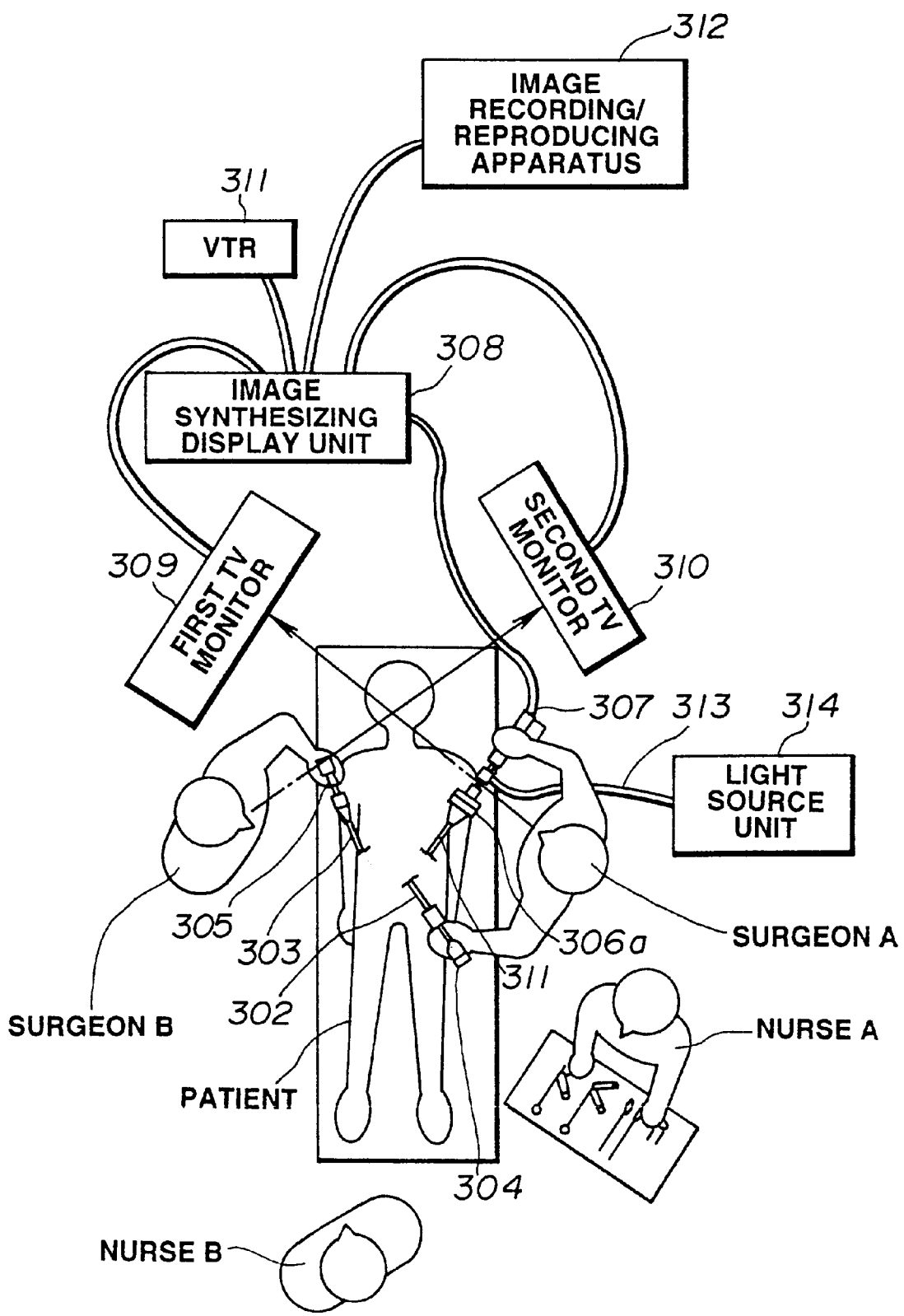
Figure 62:
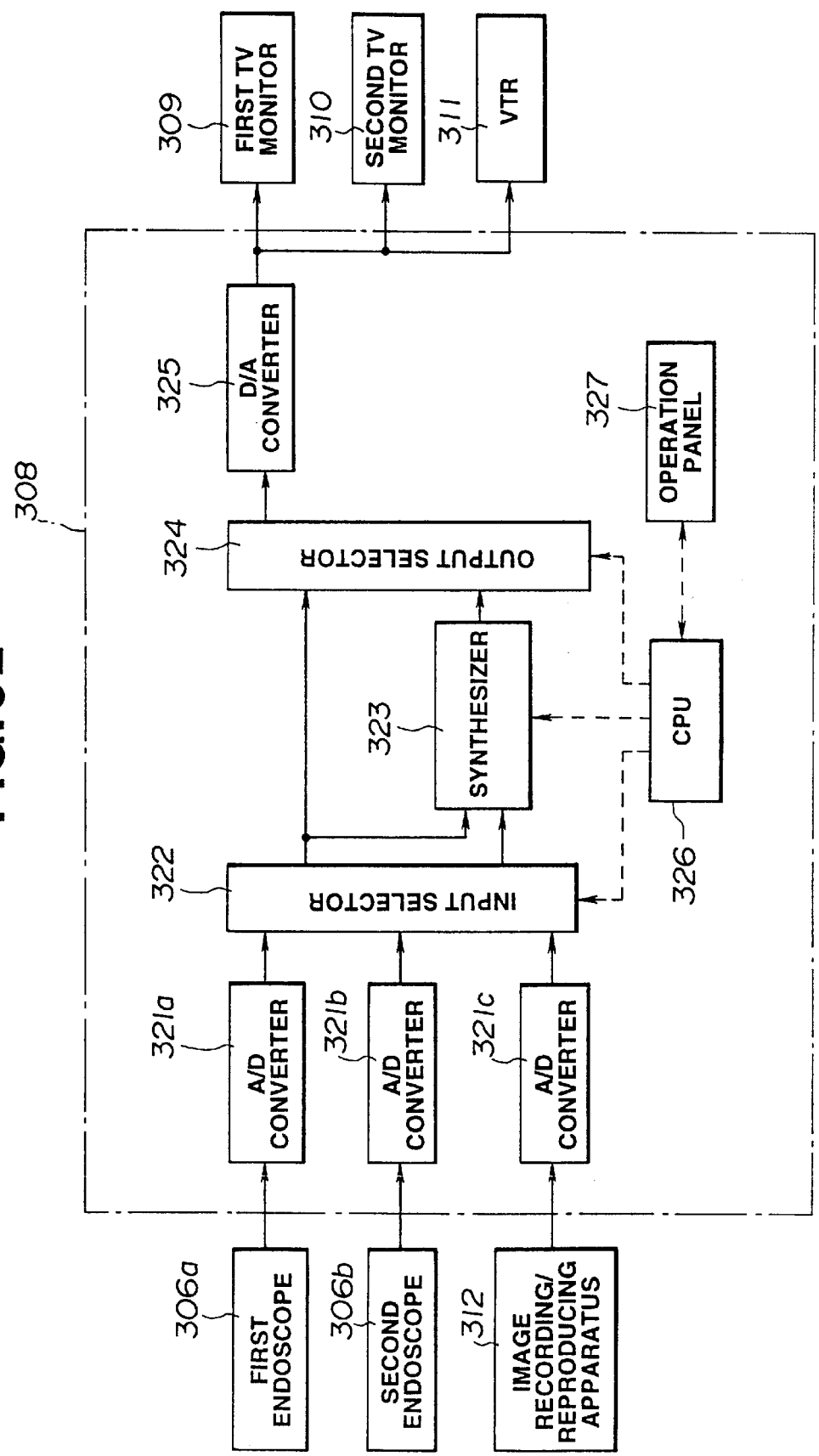
Figure 63:
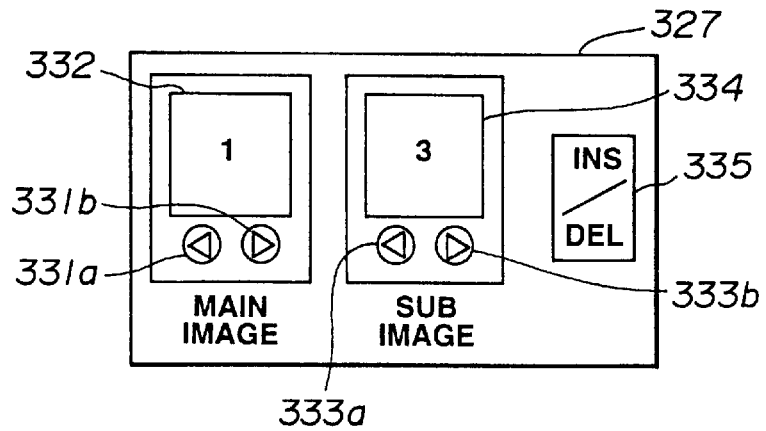
Figure 64:
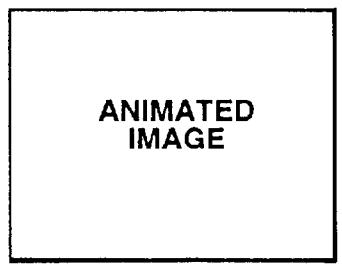
Figure 64:
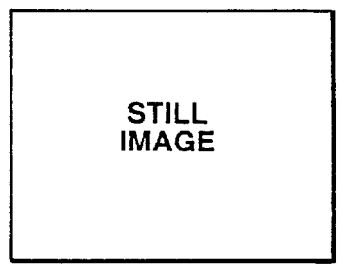
Figure 64:
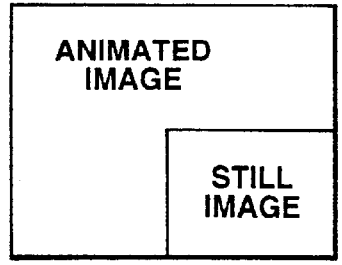
Figure 64:
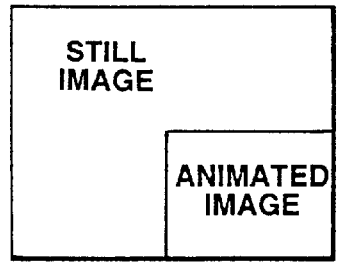
Figure 64:
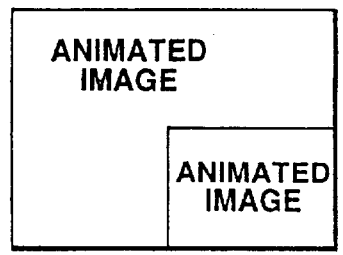
Figure 64:
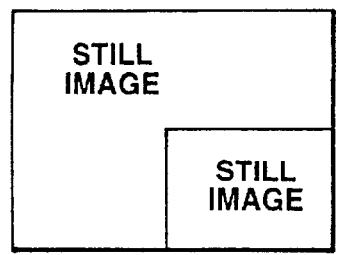
Figure 65:
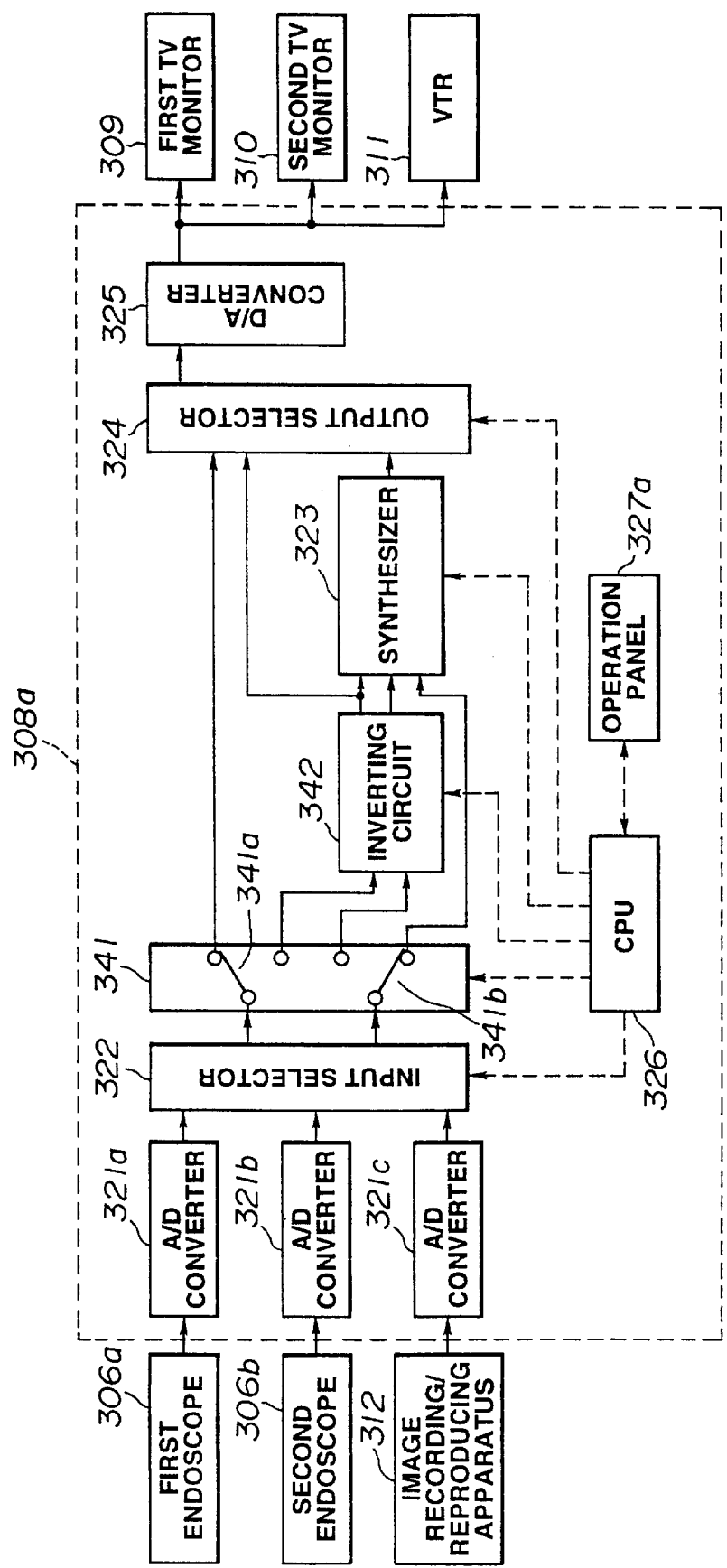
Figure 66:
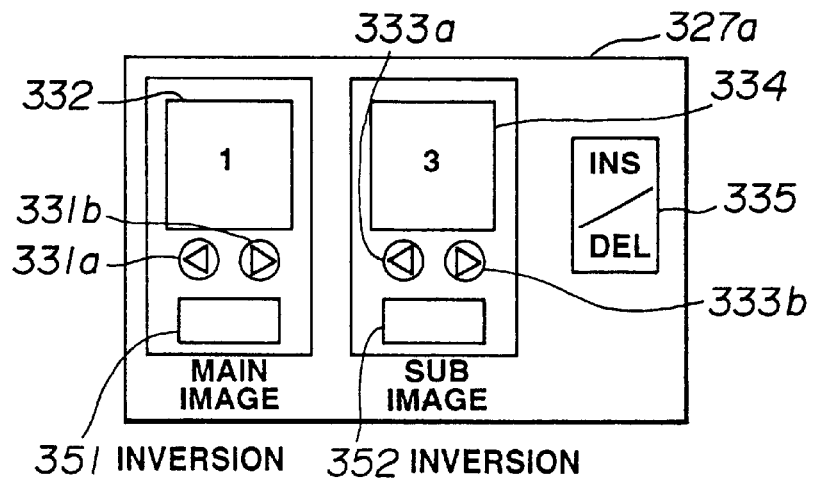
Figure 67:
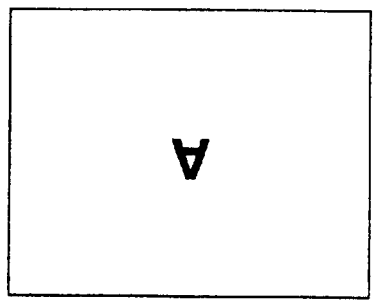
Figure 67:
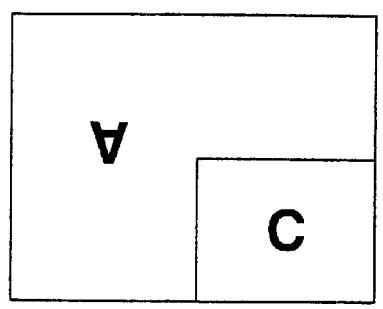
Figure 67:
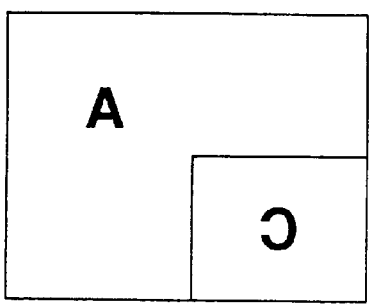
Figure 67:
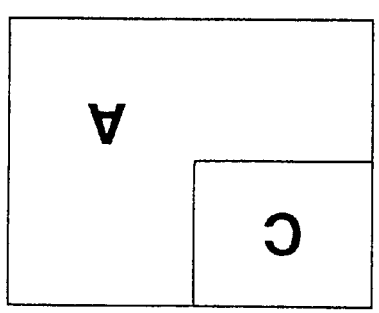
Figure 68:
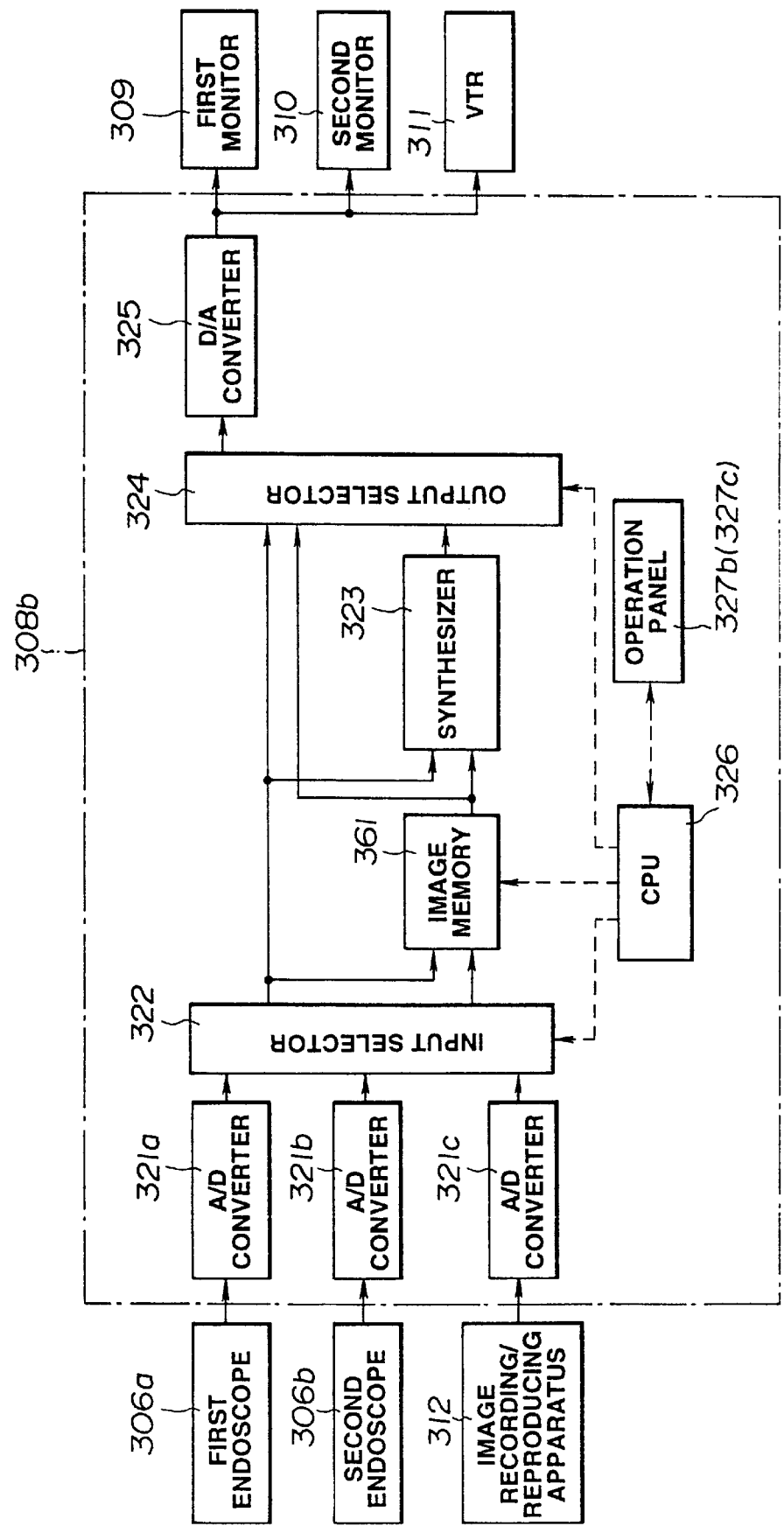
Figure 69:
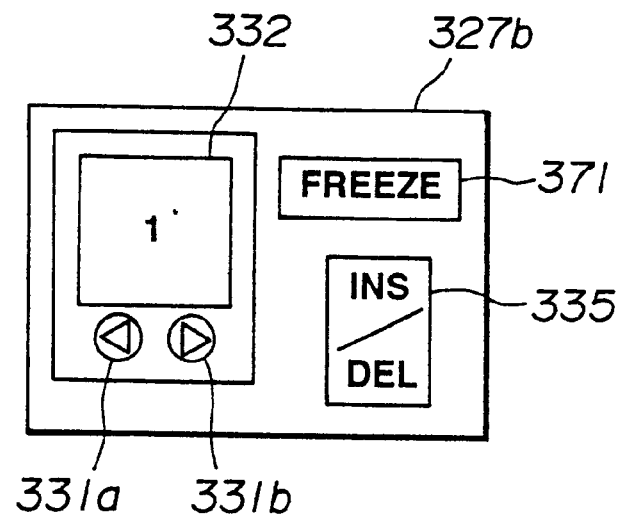
Figure 69:
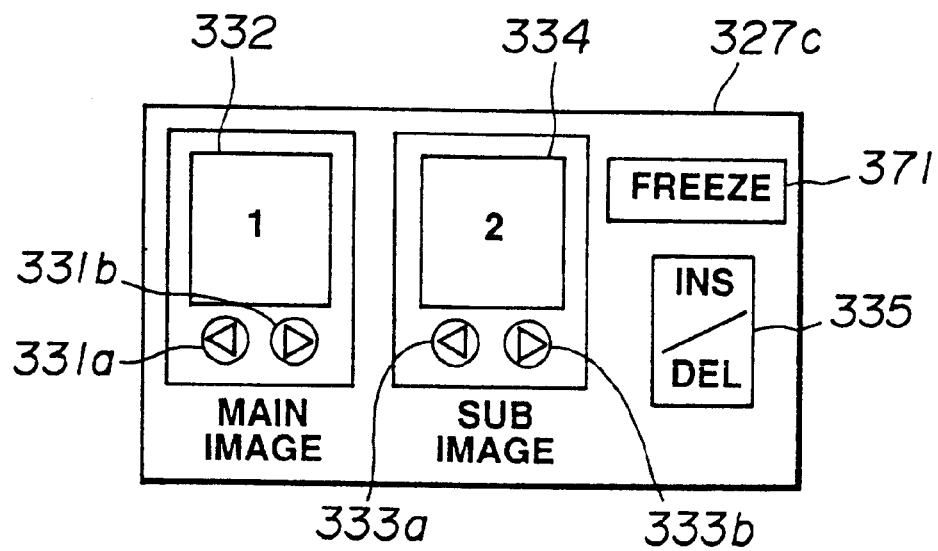
Figure 70A:
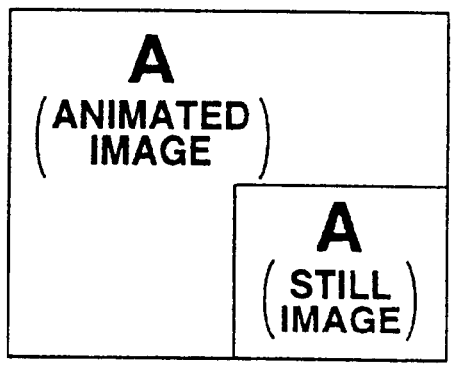
Figure 70B:
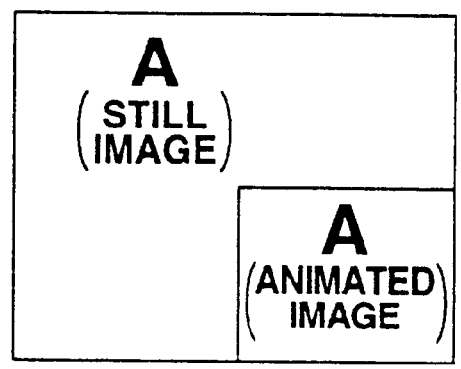
Figure 70C:
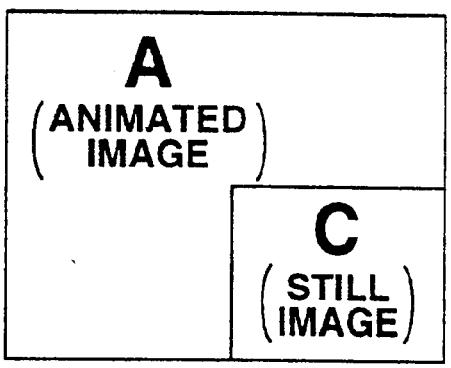
Figure 70D:
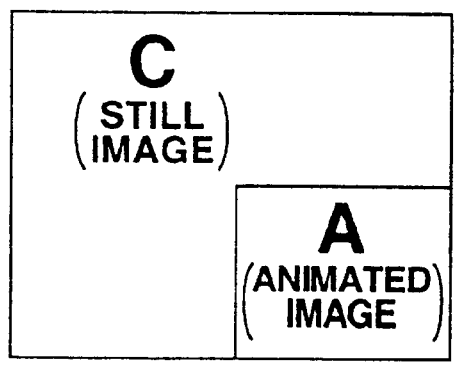
Figure 70E:
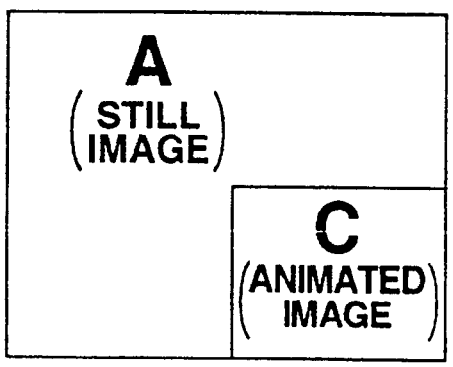
Figure 70F:
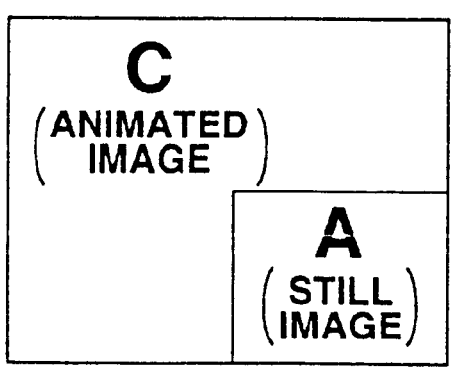
Figure 71:
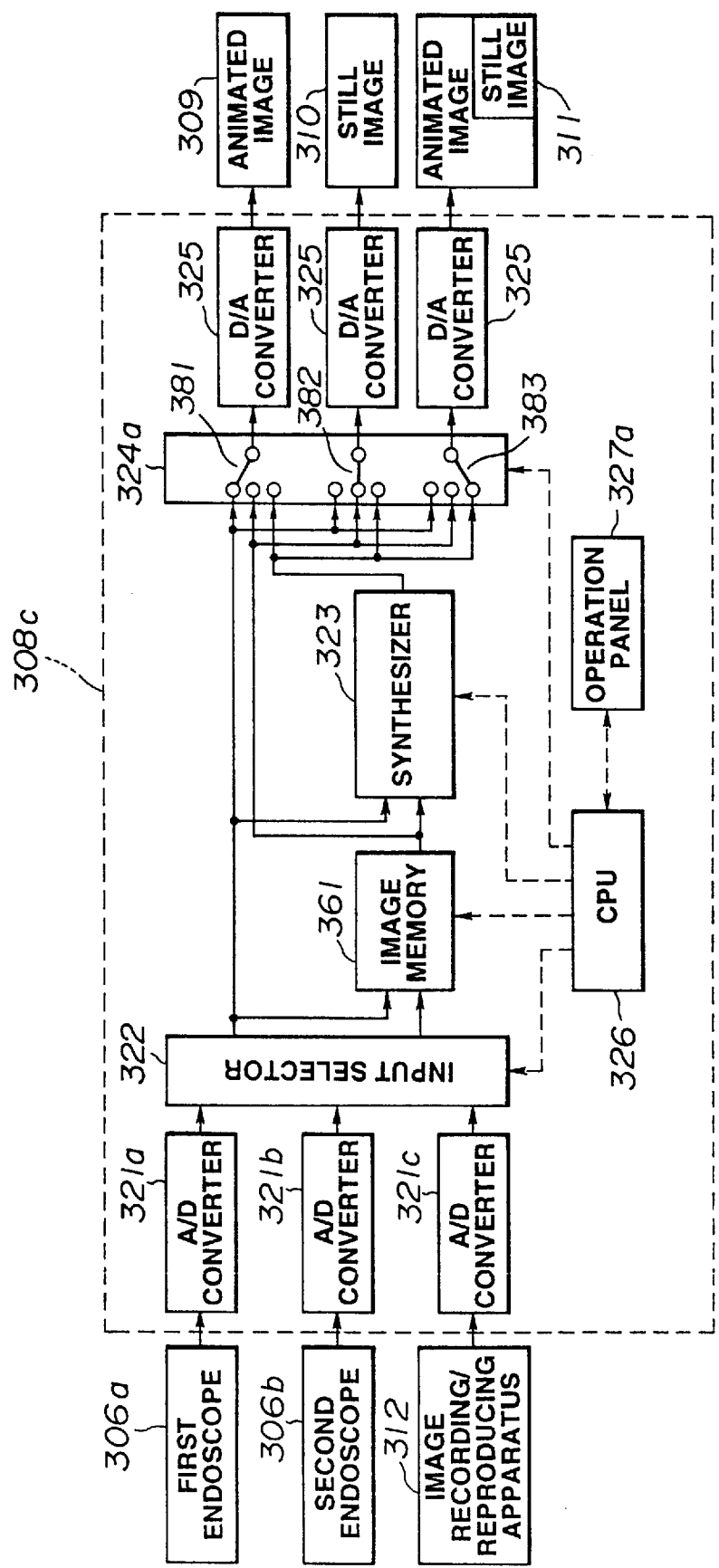
Figure 72:
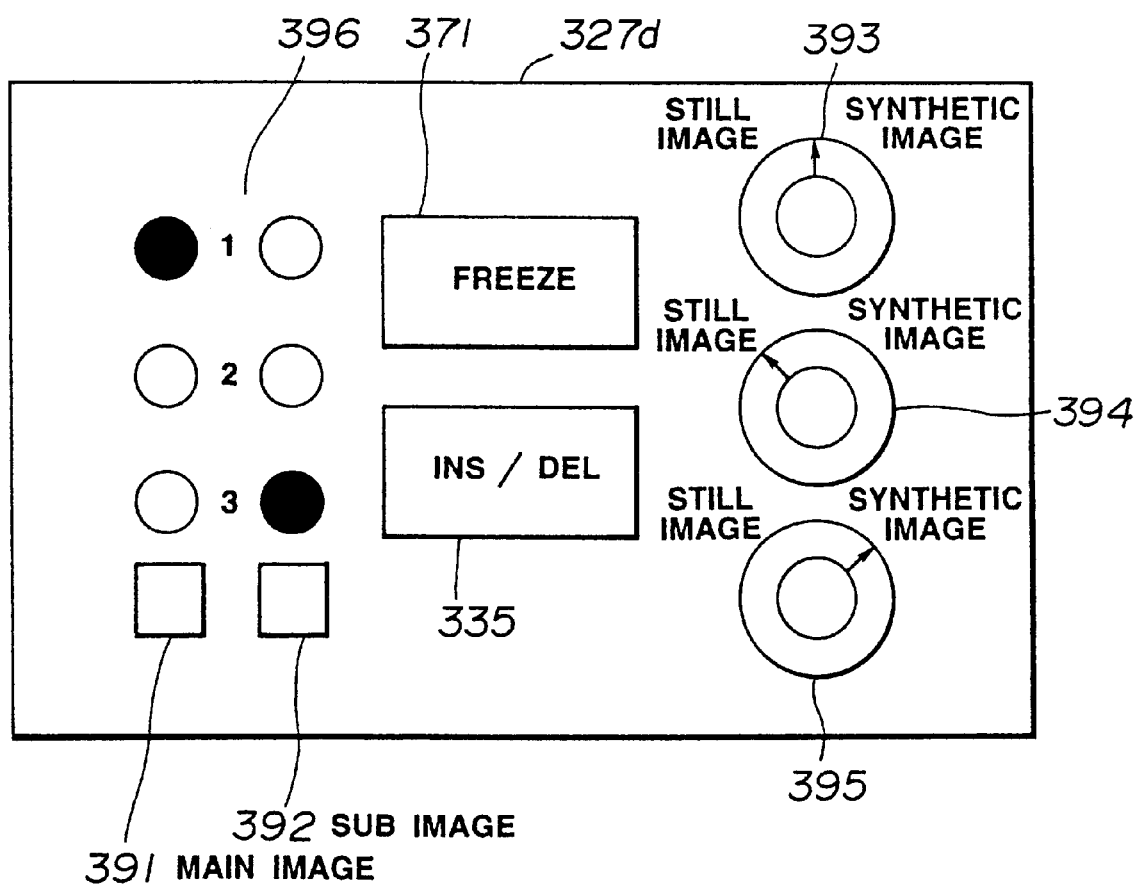
Figure 73:
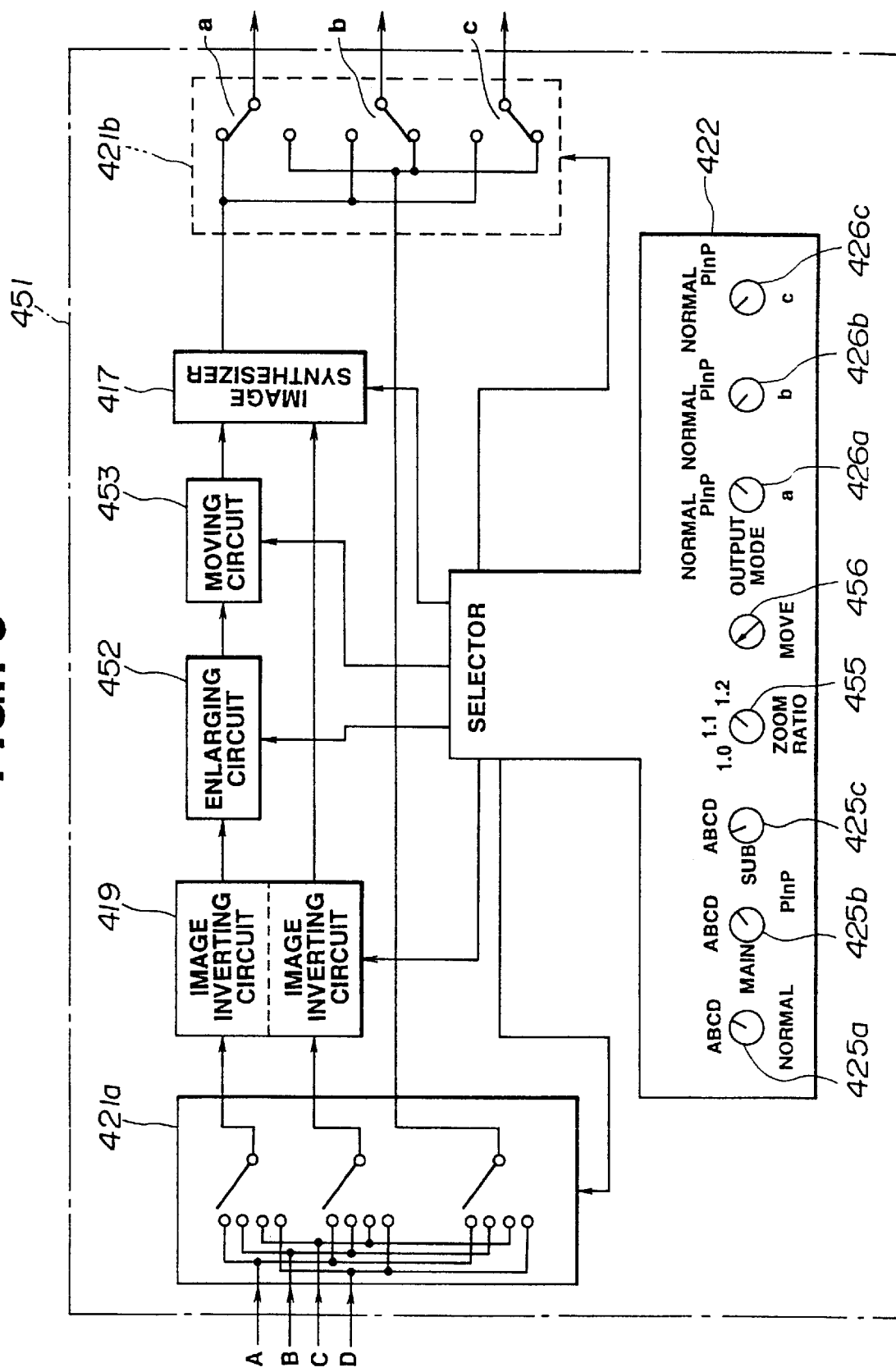
Figure 74A:
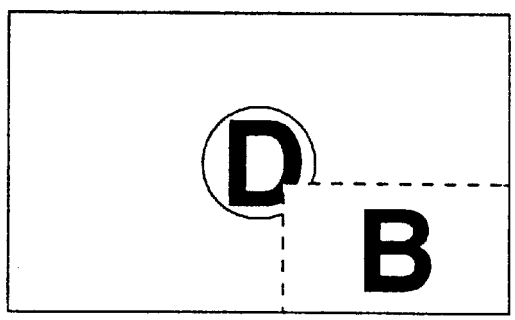
Figure 74B:
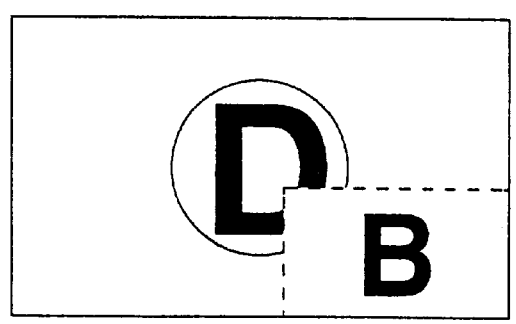
Figure 74C:
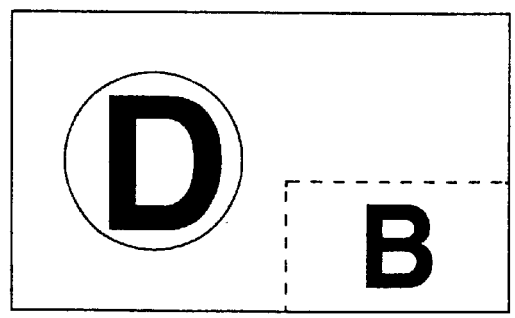
Figure 75:
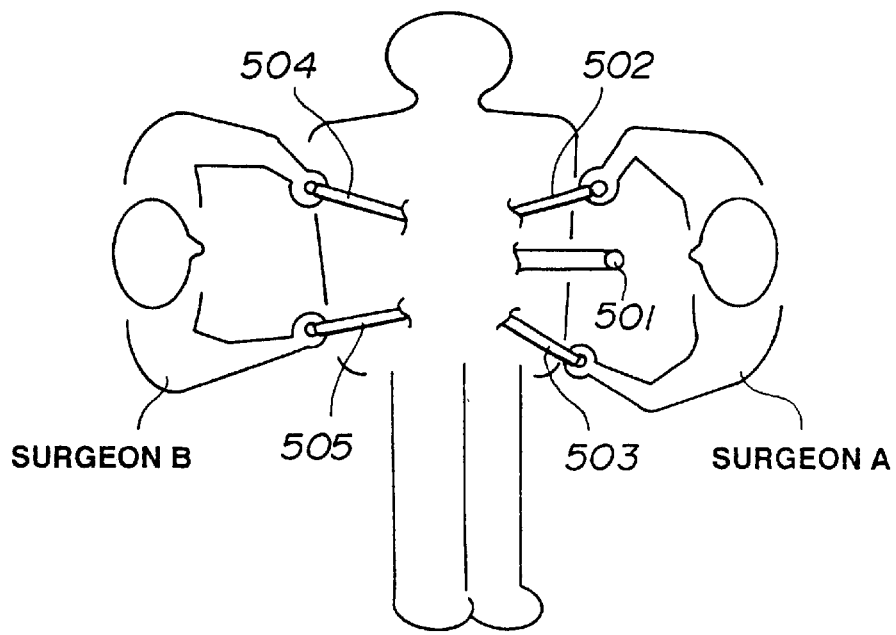
Figure 76:
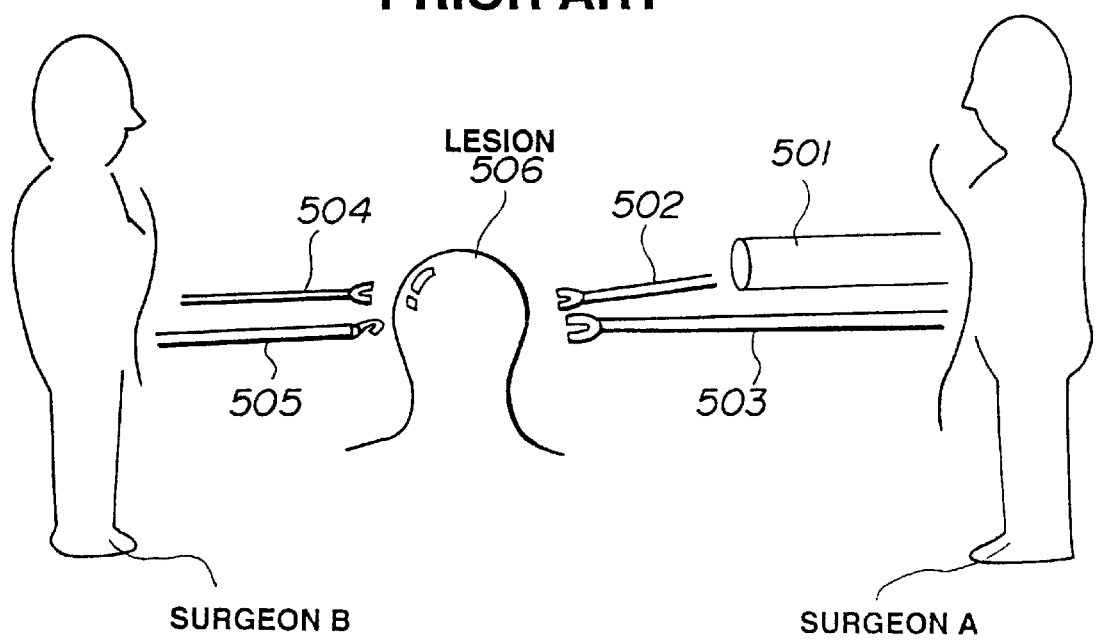
Figure 77:
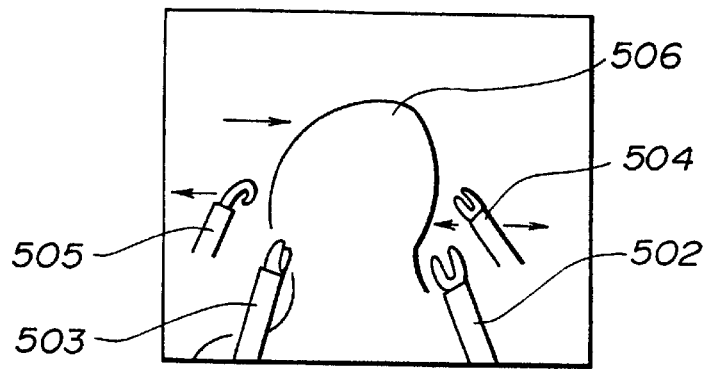
Figure 78:
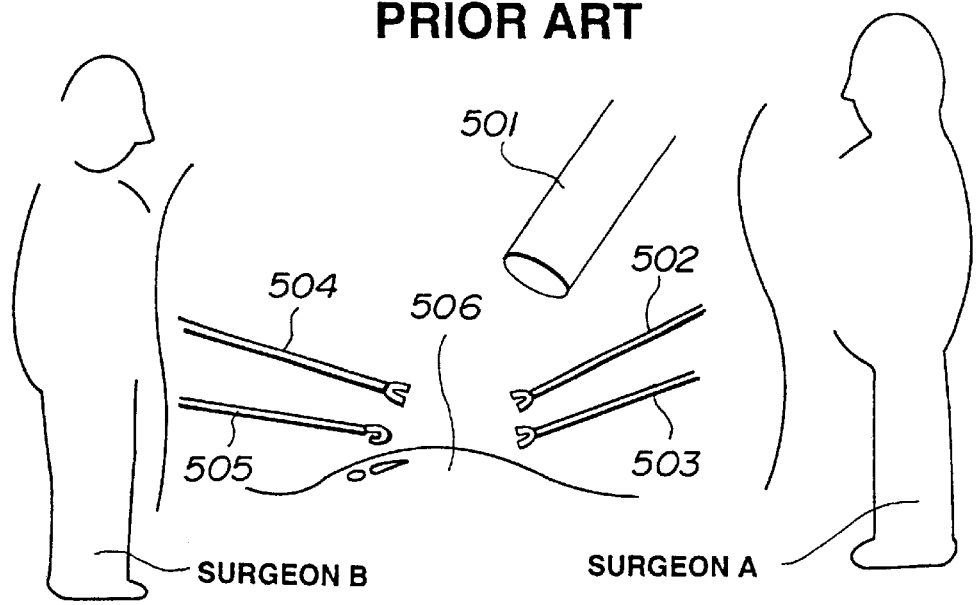
Figure 79:
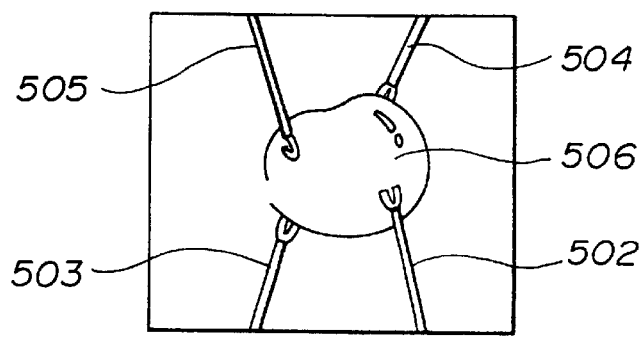

FIGS. 61 to 64F relate to the twenty-seventh embodiment of the present invention;

FIG. 61 shows a configuration of an endoscope system having an image synthesizing display unit of this embodiment;

FIG. 62 is a block diagram showing a configuration of the image synthesizing display unit shown in FIG. 61;

FIG. 63 shows a layout of the operation panel shown in FIG. 62;

FIG. 64A is the first explanatory diagram concerning the mode of operation of the image synthesizing display unit shown in FIG. 62;

FIG. 64B is the second explanatory diagram concerning the mode of operation of the image synthesizing display unit shown in FIG. 62;

FIG. 64C is the third explanatory diagram concerning the mode of operation of the image synthesizing display unit shown in FIG. 62;

FIG. 64D is the fourth explanatory diagram concerning the mode of operation of the image synthesizing display unit shown in FIG. 62;

FIG. 64E is the fifth explanatory diagram concerning the mode of operation of the image synthesizing display unit shown in FIG. 62;

FIG. 64F is the sixth explanatory diagram concerning the mode of operation of the image synthesizing display unit shown in FIG. 62;

FIGS. 65 to 67D relate to the twenty-eighth embodiment of the present invention;

FIG. 65 is a block diagram showing a configuration of an image synthesizing display unit;

FIG. 66 shows a layout of the operation panel shown in FIG. 65;

FIG. 67A is the first explanatory diagram concerning the mode of operation of the image synthesizing display unit shown in FIG. 65;

FIG. 67B is the second explanatory diagram concerning the mode of operation of the image synthesizing display unit shown in FIG. 65;

FIG. 67C is the third explanatory diagram concerning the mode of operation of the image synthesizing display unit shown in FIG. 65;

FIG. 67D is the fourth explanatory diagram concerning the mode of operation of the image synthesizing display unit shown in FIG. 65;

FIGS. 68 and 70F relate to the twenty-ninth embodiment of the present invention;

FIG. 68 is a block diagram showing a configuration of an image synthesizing display unit;

FIG. 69A shows a layout of the operation panel shown in FIG. 68;

FIG. 69B shows a layout of a variant of the operation panel shown in FIG. 68;

FIG. 70A is the first explanatory diagram concerning the mode of operation of the image synthesizing display unit shown in FIG. 68;

FIG. 70B is the second explanatory diagram concerning the mode of operation of the image synthesizing display unit shown in FIG. 68;

FIG. 70C is the third explanatory diagram concerning the mode of operation of the image synthesizing display unit shown in FIG. 68;

FIG. 70D is the fourth explanatory diagram concerning the mode of operation of the image synthesizing display unit shown in FIG. 68;

FIG. 70E is the fifth explanatory diagram concerning the mode of operation of the image synthesizing display unit shown in FIG. 68;

FIG. 70F is the sixth explanatory diagram concerning the mode of operation of the image synthesizing display unit shown in FIG. 68;

FIGS. 71 and 72 relate to the thirtieth embodiment of the present invention;

FIG. 71 is a block diagram showing a configuration of an image synthesizing display unit;

FIG. 72 shows a layout of the operation panel shown in FIG. 71;

FIGS. 73 and 74C relate to the thirty-first embodiment of the present invention;

FIG. 73 is a block diagram showing a configuration of an image processing apparatus;

FIG. 74A is the first explanatory diagram concerning the mode of operation of the image processing apparatus shown in FIG. 73;

FIG. 74B is the second explanatory diagram concerning the mode of operation of the image processing apparatus shown in FIG. 73;

FIG. 74C is the third explanatory diagram concerning the mode of operation of the image processing apparatus shown in FIG. 73;

FIGS. 75 to 79 relate to a prior art;

FIG. 75 is an explanatory diagram concerning an endoscope-aided surgical procedure;

FIG. 76 is an explanatory diagram concerning the first positional relationships of a lesion with an endoscope and a therapeutic appliance during the endoscope-aided surgical procedure shown in FIG. 75;

FIG. 77 is an explanatory diagram concerning an example of a display of an image produced under the first positional relationships shown in FIG. 76;

FIG. 78 is an explanatory diagram concerning the second positional relationships of a lesion with an endoscope and a therapeutic appliance during the endoscope-aided surgical procedure; and FIG. 79 is an explanatory diagram concerning an example of a display of an image produced under the second positional relationships shown in FIG. 78.

DETAILED DESCRIPTION OF THE PREFERRED EMBODIMENTS

Referring to the drawings, embodiments of the present invention will be described below.

To begin with, the first embodiment of the present invention will be described.

Figure 1:
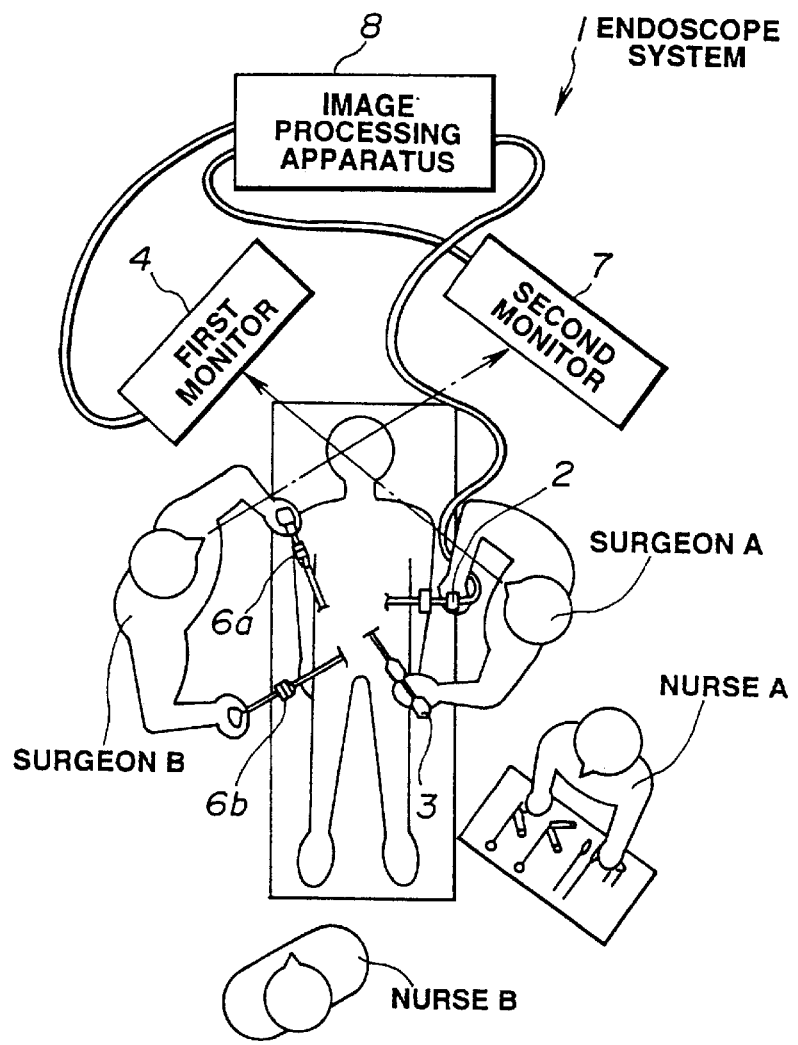
FIGS. 1 to 3 relate to the first embodiment of the present invention.

FIG. 1 shows an operation room, in which an endoscope-aided surgical procedure is under way, from above. Surgeons A and B who are assisted by nurses A and B have inserted therapeutic appliances and a rigid endoscope into a body cavity using trocars and cannulas having pierced the wall of the body cavity.

As shown in FIG. 1, the surgeon A holds an endoscope 2 with a TV camera (hereinafter, referred to merely as an endoscope) and a therapeutic appliance 3 such as forceps, which are included in an endoscope system 1, and carries out the surgical procedure while viewing a first monitor 4. The surgeon B holds therapeutic appliances 6a and 6b such as forceps and carries out the surgical procedure while viewing a second monitor 7.

A video signal sent from the TV camera of the endoscope 2 is fed to and processed by an image processing apparatus 8, and then displayed on each of the first and second monitors 4 and 7. As described previously, the first monitor 4 is viewed mainly by the surgeon A, while the second monitor 7 is viewed mainly by the surgeon B. A light source unit that is not shown is connected to the rigid endoscope.

The present invention may apply to a system configuration that includes an electronic endoscope having a solid-state imaging device attached to the tip of an insertional part thereof instead of the endoscope with a TV camera. In addition to the monitors 4 and 7, an image VTR, an optical disk drive, or any other recording means may be included.

Figure 2:
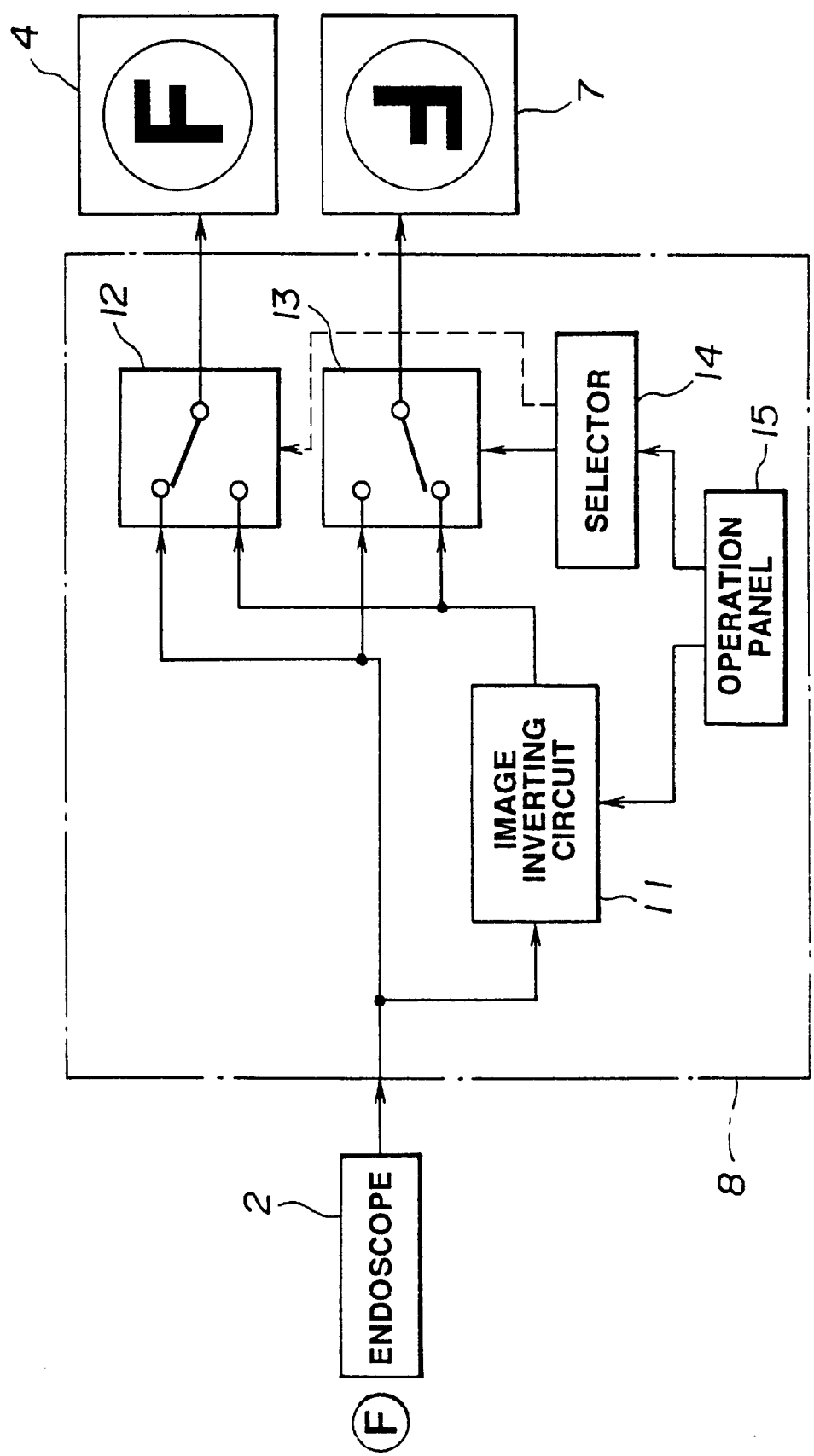
Figure 5A:
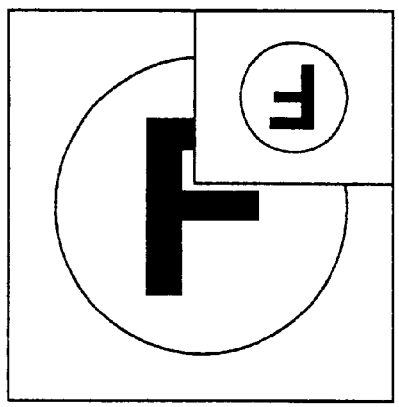
FIG. 5A is the first explanatory diagram schematically showing an image processed by the image processing apparatus shown in FIG. 4.
Figure 5D:
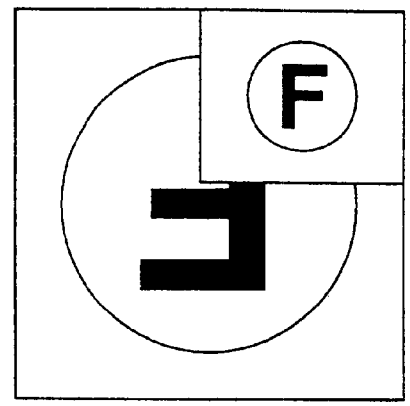
FIG. 5D is the fourth explanatory diagram schematically showing an image processed by the image processing apparatus shown in FIG. 4.
Figure 5B:
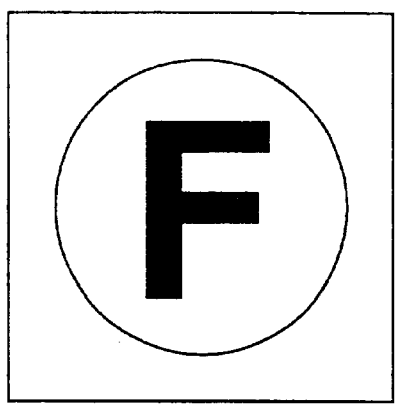
FIG. 5B is the second explanatory diagram schematically showing an image processed by the image processing apparatus shown in FIG. 4.
Figure 5E:
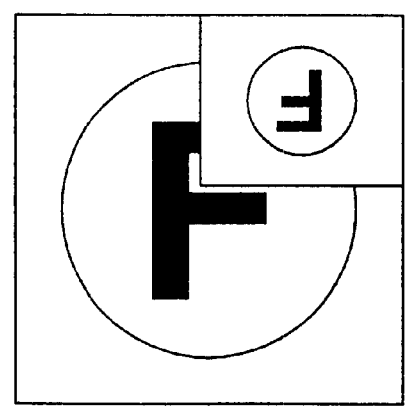
FIG. 5E is the fifth explanatory diagram schematically showing an image processed by the image processing apparatus shown in FIG. 4.
Figure 5C:
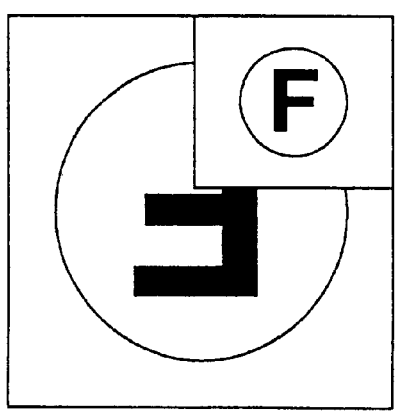
FIG. 5C is the third explanatory diagram schematically showing an image processed by the image processing apparatus shown in FIG. 4.
Figure 5F:
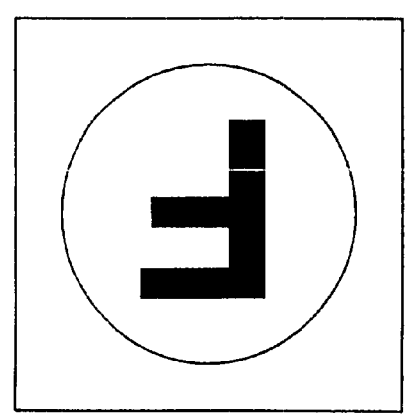

As shown in FIG. 2, the image processing apparatus 8 supplies a video signal sent from the endoscope 2 to each of an image inverting circuit 11 and selector switches 12 and 13. The image inverting circuit 11 inverts an image (laterally (to produce a mirror image), vertically, or vertically and laterally (180°)), and supplies a processed video signal to each of the selector switches 12 and 13. Each of the selector switches 12 and 13 selects a video signal to be supplied to each of the first and second monitors 4 and 7 serving as display means in response to a control signal sent from a selector 14.

In this specification, inversion is used as a generic term meaning any of lateral inversion (to produce a mirror image), vertical inversion, and vertical and lateral inversion (to produce a 180° turned image) which are performed by the image inverting circuit.

Figure 3:
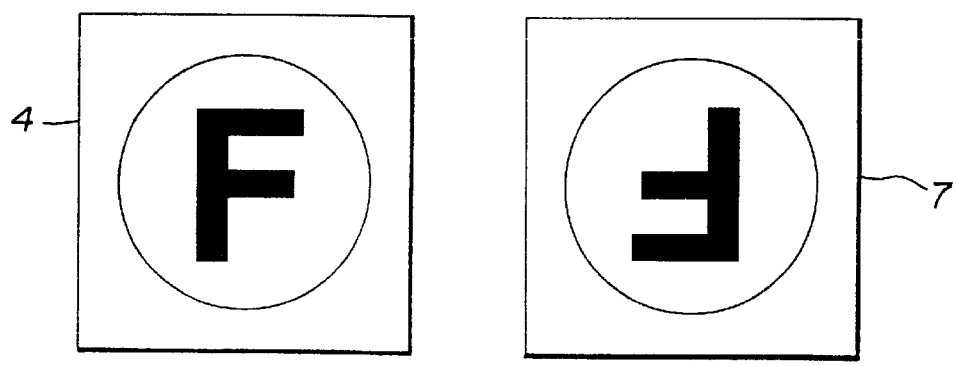

The contents of processing to be performed by the image inverting circuit 11 and a video signal to be selected by the selector 14 are designated using setting switches on the operation panel 15. As a result, images such as those shown in FIG. 3 are selectively displayed on each of the first monitor 4 and second monitor 7.

In the endoscope system 1 having the image processing apparatus 8 configured as mentioned above, as shown in FIG. 1, the surgeon A stands in the same direction as the endoscope 2 but the surgeon B is opposed to the endoscope 2. As shown in FIG. 3, when a raw image (erect image F) is displayed on the first monitor 4 and a vertically and laterally inverted image (inverted image made by turning the image F 180°), the surgeon B can manipulate the therapeutic appliances 6a and 6b without any sense of unnaturalness.

Image inversion can be specified arbitrarily at an operation panel 15. With the progress of surgery, the endoscope 2 may change the orientation so as to face the surgeon A. The displays on the first and second monitors 4 and 7 should therefore be exchanged for each other. Even in this case, the operation panel 15 is used to modify settings in the image processing apparatus so that the displays on the monitors are exchanged for each other. It is therefore unnecessary to replace the first monitor 2 with the second monitor 7 or change connections of output video signals. Thus, displays on monitors can be changed quickly according to the contents of the displays dependent on the orientation of the endoscope 2, though a surgical procedure is not be interrupted.

Since the surgeons A and B can use different monitors, the monitors can be installed at easy-to-see places or in easy-to-see orientations. This feature is advantageous from the viewpoint of improved operability.

Next, the second embodiment will be described.

The second embodiment is substantially identical to the first embodiment except the configuration of an image processing apparatus. The difference alone will be described. Identical components will be assigned the same reference numerals, of which no mention will be made.

As shown in FIG. 4, an image processing apparatus 8a in the second embodiment supplies a video signal sent from the endoscope 2 to each of the image inverting circuit 11, selector switches 12 and 13, and image synthesizers 16 and 17. The image inverting circuit 11, similarly to the one in the first embodiment, inverts an image and supplies a processed video signal to each of the selector switch 12 and image synthesizers 16 and 17.

Each of the image synthesizers 16 and 17 receives a video signal representing a raw image provided by the endoscope 2 and a video signal image-wise inverted by the image inverting circuit 11, selectively synthesizes the input video signals so as to produce a picture-in-picture image, and supplies a video signal representing the picture-in-picture image to each of the selector switches 12 and 13.

In this specification, a large image serving as a base of a picture-in-picture image shall be referred to as a main image, while a small image to be superposed on and synthesized with the main image shall be referred to as a sub image.

In response to a control signal sent from the selector 14, each of the selector switches 12 and 13 selects the video signal representing a raw image provided by the endoscope 2, the video signal sent from the image inverting circuit 11, or the video signal representing a picture-in-picture image sent from each of the image synthesizers 16 and 17, and supplies a selected video signal to the TV monitor 21. The contents of processing to be performed by the image inverting circuit 11, a main image and a sub image to be synthesized into a picture-in-picture image by the image synthesizer 22, and a video signal to be selected by the selector 14 are specified at the operation panel 15 as mentioned in conjunction with the first embodiment. On the first monitor 4 and second monitor 7, various display images as those shown, for example, in FIGS. 5A to 5F are displayed selectively. The other components are identical to those in the first embodiment.

In the endoscope having the thus configured image processing apparatus 8a, as shown in FIG. 1, the surgeon A stands in the same orientation as the endoscope 2, while the surgeon B faces the endoscope 2. When a first picture-in-picture image having a raw image (erect image) as a main image and a vertically and laterally inverted image (inverted image) as a sub image (FIG. 5A) is displayed on the first monitor 4 and a second picture-in-picture image (FIG. 5D) having a vertically and laterally inverted image (inverted image) as a main image and a raw image (erect image) as a sub image is displayed on the second monitor 7, the surgeon B can manipulate the therapeutic appliances 6a and 6b without any sense of unnaturalness.

In addition to the advantage of the first embodiment, the second embodiment has the advantage that since a main image appearing on one of the first and second monitors viewed by a partner is displayed as a sub-image on the other monitor 4 or 7, the surgeons A and B communicate with each other more easily.

Next, the third embodiment will be described.

The third embodiment is substantially identical to the first embodiment. Different components alone will be described. Identical components will bear the same reference numerals, of which no mention will be made.

In the first embodiment, an image processing apparatus inverts image-wise a video signal sent from the endoscope 2 and displays images on two monitors. In the third embodiment, an image processing apparatus is adapted for an endoscope system including a single monitor.

Figure 6:
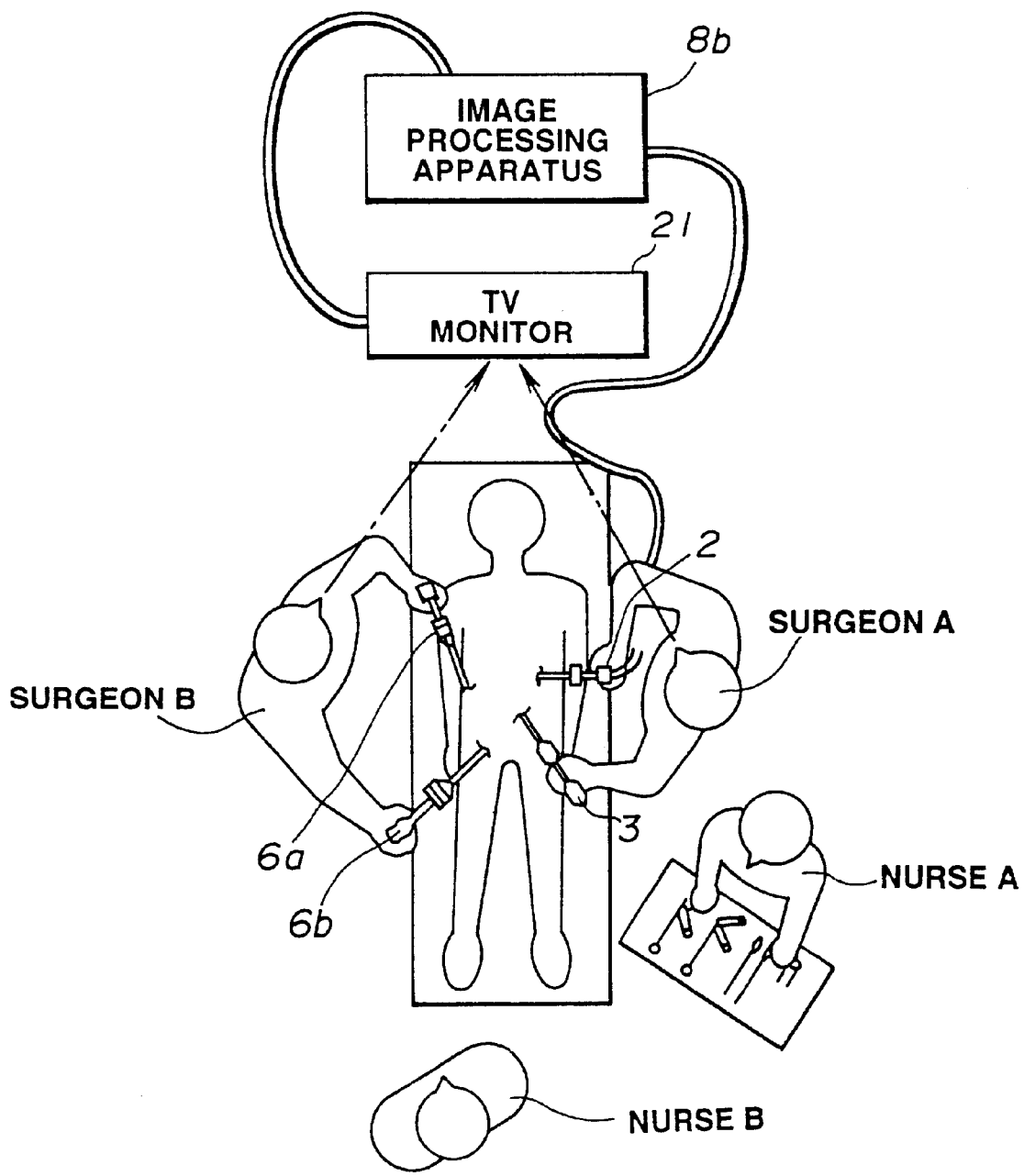

As shown in FIG. 6, a video signal sent from the endoscope 2 is fed to an image processing apparatus 8b of the third embodiment. A video signal processed by the image processing apparatus 8b is displayed on the TV monitor 21.

Figure 7A:
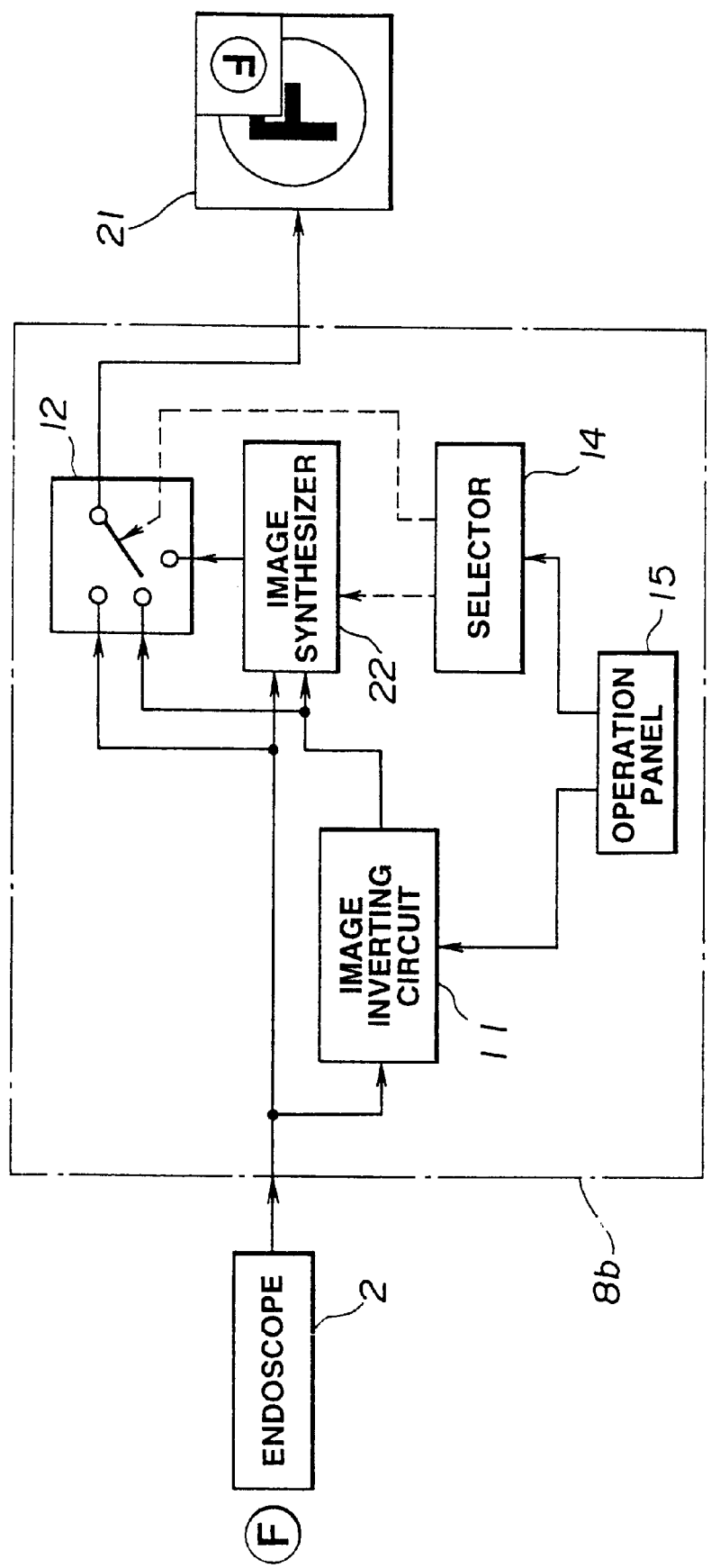
FIG. 7A shows a configuration of the image processing apparatus shown in FIG. 6.

The image processing apparatus 8b supplies, as shown in FIG. 7A, a video signal sent from the endoscope 2 to each of the image inverting circuit 11, selector switch 12, and image synthesizer 22. The image inverting circuit 11 inverts an image similarly to the one in the first embodiment, and supplies a processed video signal to each of the image synthesizer 22 and selector switch 12. The image synthesizer 22 receives a video signal representing a raw image from the endoscope 2 and an image-wise inverted video signal from the image inverting circuit 11, synthesizes the input video signals selectively so as to produce a picture-in-picture image, and supplies a video signal representing the picture-in-picture image to the selector switch 12.

In response to a control signal sent from the selector 14, the selector switch 12 selects the video signal representing a raw image provided by the endoscope 2, the video signal sent from the image inverting circuit 11, or the video signal representing a picture-in-picture image provided by the image synthesizer 22, and supplies a selected video signal to the TV monitor 21.

The contents of processing to be performed by the image inverting circuit 11, a main image and a sub image to be synthesized into a picture-in-picture image by the image synthesizing circuit 22, and a video signal to be selected by the selector 14 are, similarly to those in the first embodiment, designated using setting switches on the operation panel 15.

Figure 7B:
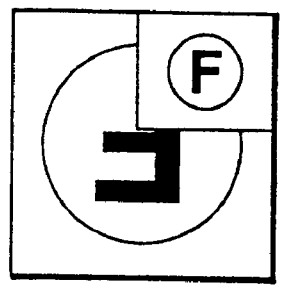
FIG. 7B is the first explanatory diagram showing an example of a display in the image processing apparatus shown in FIG. 7A.
Figure 7C:
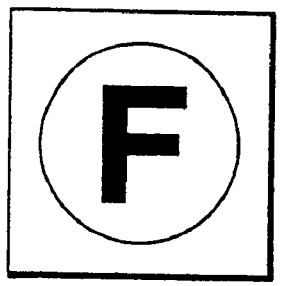
FIG. 7C is the second explanatory diagram showing an example of a display in the image processing apparatus shown in FIG. 7A.
Figure 7D:
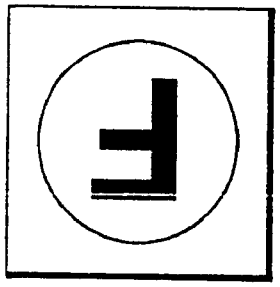
FIG. 7D is the third explanatory diagram showing an example of a display in the image processing apparatus shown in FIG. 7A.

As a result, various display images shown in FIGS. 7A and 7B (for example, an example of a display of FIG. 7A or examples of displays of FIGS. 7B to 7D) selectively appear on the TV monitor 21. The other components are identical to those in the first embodiment.

In the endoscope system having the thus configured image processing apparatus 8b, as shown in FIG. 6, the surgeon A acts as a main doctor and mainly manipulates a therapeutic appliance and the surgeon B acts as an assistant doctor and manipulates an auxiliary therapeutic appliance. In this situation, since the surgeon A stands in the same orientation as the endoscope 2, he/she can manipulate the therapeutic appliance without any problem while seeing a raw image (erect image or an image F in an example in FIG. 5C) produced by the endoscope 2 and displayed on the TV monitor 21. However, since the surgeon B acting as an assistant doctor is opposed to the endoscope 2, he/she finds the raw image provided by the endoscope 2 vertically and laterally or laterally inverse and has a sense of unnaturalness in manipulating the therapeutic appliance.

Figure 8:
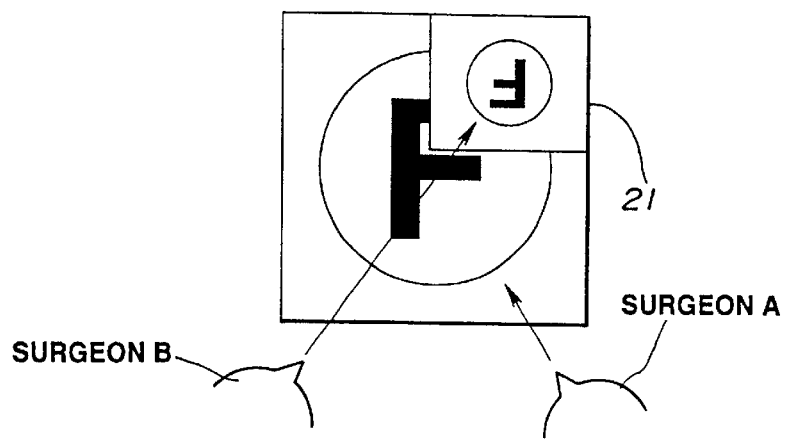

The operation panel 15 is then used to instruct the image synthesizer 22 to produce a picture-in-picture image having a raw image provided by the endoscope 2 as a main image and a vertically and laterally inverted image (inverted image made by turning the image F by 180°) as a sub image. The picture-in-picture image shown as an example of a display FIG. 7A is then displayed on the TV monitor 21 via the selector switch 12. Thus, as shown in FIG. 8, the surgeon A can manipulate the therapeutic appliance while seeing the main image and the surgeon can manipulate the therapeutic appliance while seeing the sub image.

As a result, similarly to the first embodiment, the surgeon B can manipulate the therapeutic appliance without any sense of unnaturalness and assist the surgeon A acting as a main doctor.

When the surgeon B opposed to the endoscope 2 acts as a main doctor and mainly manipulates a therapeutic appliance, the operation panel 15 is used to instruct the image synthesizer 22 to produce a picture-in-picture image having an image (inverted image made by turning F 180°) made by vertically and laterally inverting a raw image provided by the endoscope 2 as a main image and the raw image provided by the endoscope 2 as a sub image. The picture-in-picture image shown as an example of a display FIG. 7B is then displayed on the TV monitor 21 via the selector switch 12. Thus, the surgeon B can manipulate the therapeutic appliance without any sense of unnaturalness while seeing the inverted image displayed as the main image. The surgeon A can also manipulate the therapeutic appliance without any sense of unnaturalness while seeing the raw image displayed as the sub image.

The image synthesizer 22 for synthesizing images may be configured so that it controls writing or reading of an image memory (in this embodiment, the selector 14 controls it) so as to produce a synthetic image. In this case, the capability of the selector switch 12 is implemented in the image synthesizing circuit 22. This obviates the necessity of the selector switch 12 shown in FIG. 7A Even when the circuits and switches are installed at different places or increased in number, the same image as that provided by this embodiment can apparently be produced.

Next, the fourth embodiment will be described.

The fourth embodiment is substantially identical to the third embodiment. Different components alone will be described. Identical components will be assigned the same reference numerals, of which no mention will be made.

Figure 9:
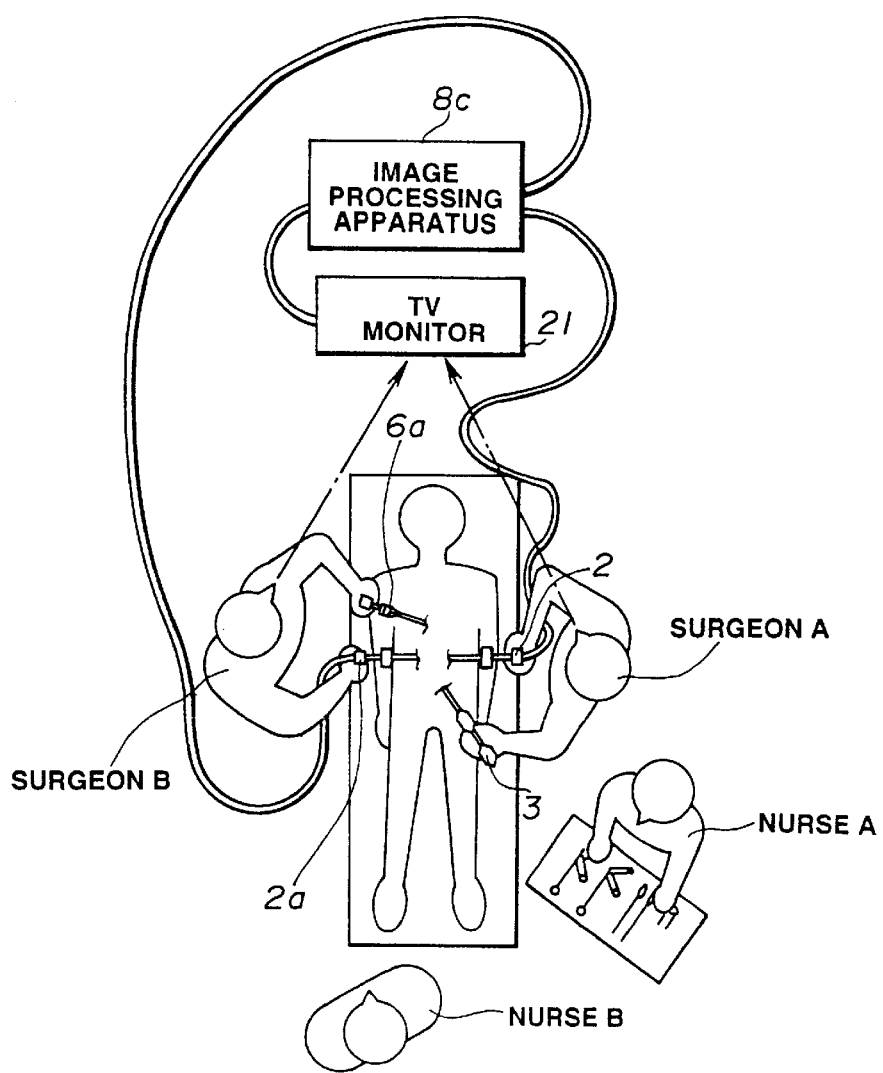

In an endoscope system of the fourth embodiment, as shown in FIG. 9, unlike the one of the third embodiment, the surgeon B uses a second endoscope 2a instead of the therapeutic appliance 6b. The second endoscope 2a images the back of a lesion to be imaged by the endoscope 2 manipulated by the surgeon A. The surgeons A and B carry out a surgical procedure while concurrently manipulating the endoscopes 2 and 2a. An image processing apparatus 8c of the fourth embodiment therefore receives video signals from the two endoscopes 2 and 2a, processes the signals, and supplies processed signals to the TV monitor 21.

As shown in FIG. 10, the image processing apparatus 8c of the fourth embodiment supplies the video signals sent from the endoscopes 2 and 2a to each of the image inverting circuits 11a and 11b, selector switch 12, and image synthesizer 22. Each of the image inverting circuits 11a and 11b inverts, similarly to those in the first embodiments, an image and supplies a processed video signal to each of the image synthesizer 22 and selector switch 12. The image synthesizer 22 receives video signals representing raw images from the endoscopes 2 and 2a and image-wise inverted video signals from the image inverting circuits 11a and 11b, selectively synthesizes the input video signals so as to produce a picture-in-picture image, and supplies a video signal representing the picture-in-picture image to the selector switch 12.

In response to a control signal sent from the selector 14, the selector switch 12 selects the video signals sent from the endoscopes 2 and 2a, the video signals sent from the image inverting circuits 11a and 11b, or the video signal representing a picture-in-picture image sent from the image synthesizer 22, and then supplies a selected video signal to the TV monitor 21.

The contents of processing to be performed by the image inverting circuits 11a and 11b, a main image and a sub image to be synthesized into a picture-in-picture image by the image synthesizer 22, and a video signal to be selected by the selector 14 are, similarly to those in the first embodiment, designated using setting switches on the operation panel 15.

As a result, as shown in an example of a display on the TV monitor 21 in FIG. 10, a picture-in-picture image having a raw image provided by the endoscope 2 handled by the surgeon A as a main image and an image (inverted image) made by vertically and laterally inverting the raw image provided by the endoscope 2a handled by the surgeon B as a sub image is displayed. The other components are identical to those in the third embodiment.

In FIG. 9, for example, when the surgeon A mainly manipulates a therapeutic appliance, a picture-in-picture image having an image provided by the endoscope 2 as a main image and an image provided by the endoscope 2a as a sub image is displayed on the TV monitor 21. When an image J provided by the endoscope 2a opposed to the surgeon A is displayed as it is, the surgeon A finds the image J vertically and laterally inverse and has difficulty in interpreting image information of the back of a lesion. This results in deteriorated operability.

Figure 11A:
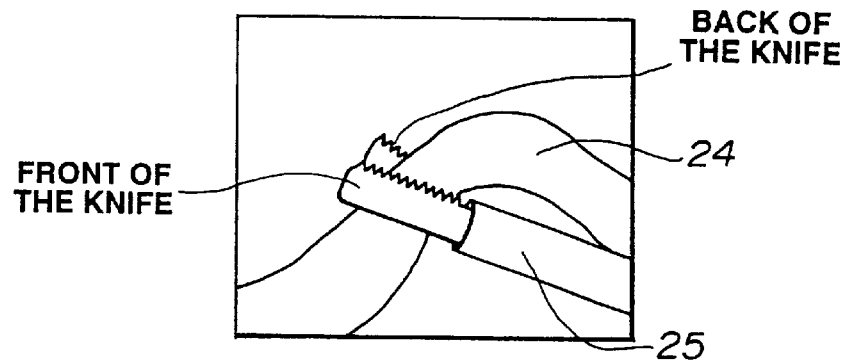
FIGS. 11A is the first explanatory diagram showing images of the front and back of a lesion provided by the two endoscopes shown in FIG. 9.
Figure 11B:
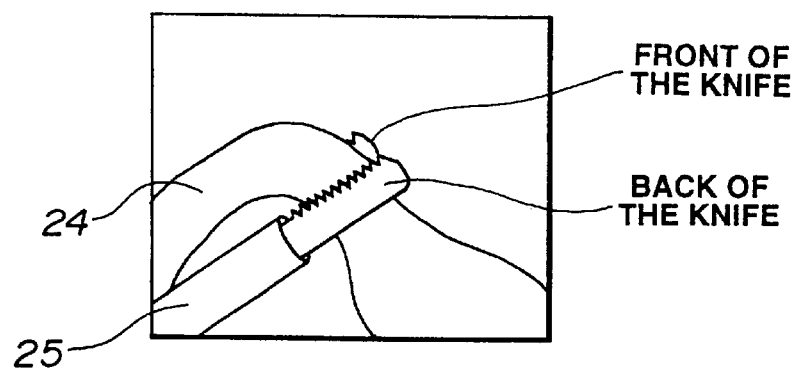
FIG. 11B is the second explanatory diagram showing images of the front and back of a lesion provided by the two endoscopes shown in FIG. 9.
Figure 11C:
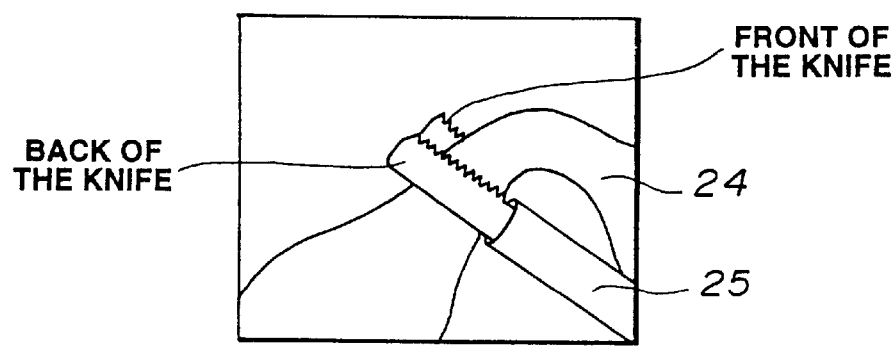
FIG. 11C is the third explanatory diagram showing images of the front and back of a lesion provided by the two endoscopes shown in FIG. 9.

For cutting the intestine 24 that is a lesion using a knife 25 that is a therapeutic appliance, the endoscope 2 is used to obtain an image shown in FIG. 11A and the endoscope 2a is used to obtain an image shown in FIG. 11B that renders the back of the knife 25 shown in FIG. 11A as a front view. When the image provided by the endoscope 2 is displayed as a main image and the image provided by the endoscope 2a is displayed as a sub image as it is, the surgeon A observes, as apparent from FIGS. 11A and 11B, the main image and sub image which are mutually vertically and laterally inverse. The image inverting circuit 11b is then used to produce a mirror image shown in FIG. 11C by laterally inverting the image provided by the endoscope 2a. The mirror image is displayed as a sub image.

In this embodiment, the operation panel 15 is used to instruct the image synthesizer 22 to produce a picture-in-picture image whose sub image is a mirror image made by laterally inverting the image provided by the endoscope 2a or an inverted image made by vertically and laterally inverting the image provided by the endoscope 2a. The picture-in-picture image is then displayed on the TV monitor 21.

The surgeon A can therefore observe an image J rendering the back of a lesion, which is invisible in an image F provided by the endoscope 2, as a sub image and manipulate a therapeutic appliance without any sense of unnaturalness.

When the surgeon B mainly manipulates a therapeutic appliance, a picture-in-picture image having the image J provided by the endoscope 2a as a main image and a mirror image made by laterally inverting the image F provided by the endoscope 2 or an inverted image made by vertically and laterally inverting the image F as a sub image is displayed on the TV monitor 21. The surgeon B can manipulate the therapeutic appliance without any sense of unnaturalness while observing the front and back of a lesion at a time.

Figure 12A:
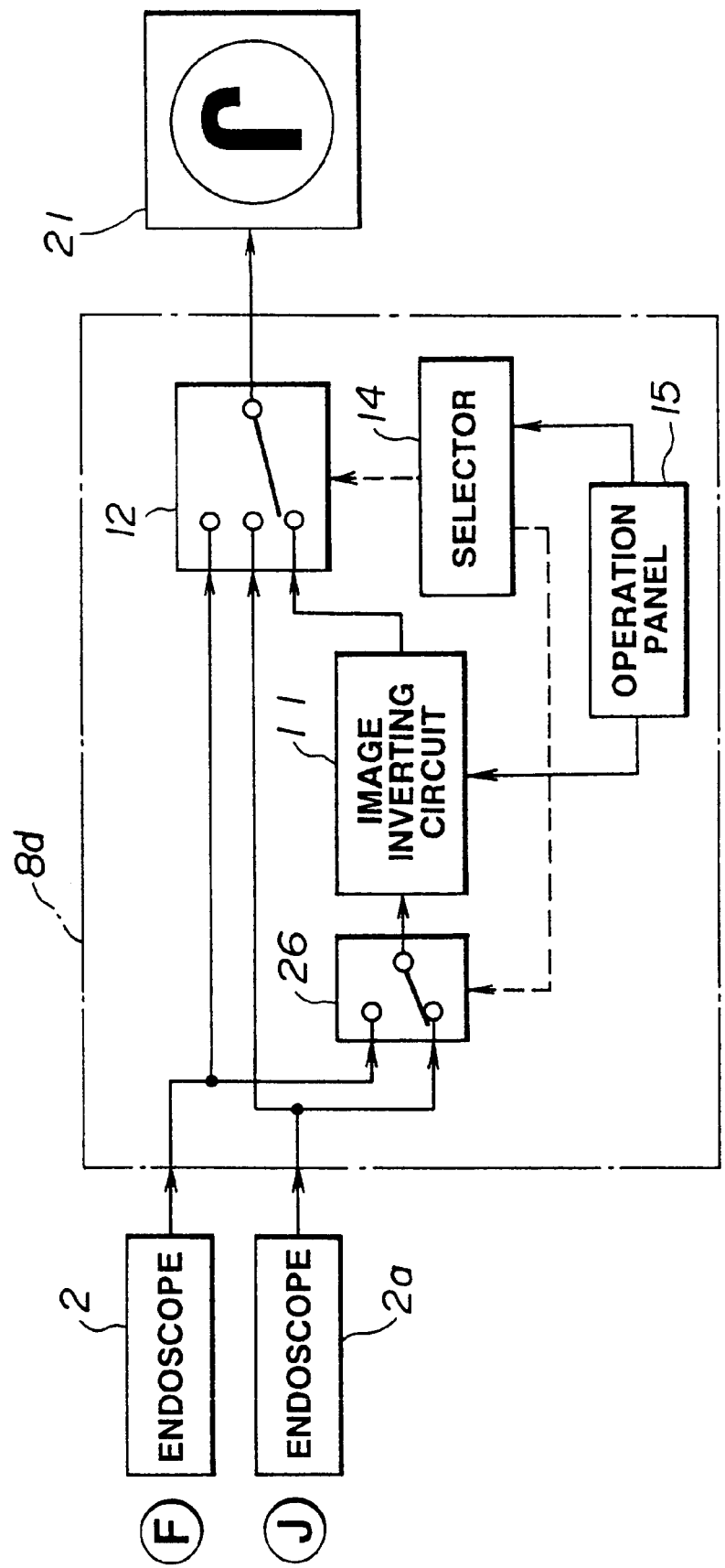
FIG. 12A shows a configuration of a variant of the image processing apparatus shown in FIG. 9.
Figure 12B:
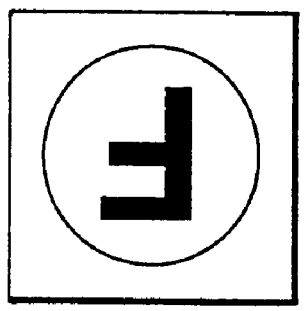
FIG. 12B is the first diagram showing an example of a display in the image processing apparatus shown in FIG. 12A.
Figure 12E:
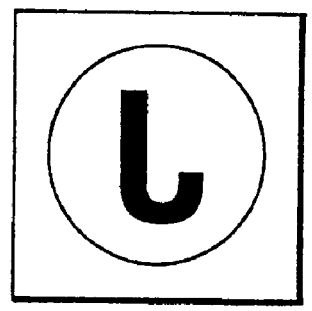
FIG. 12E is the fourth diagram showing an example of a display in the image processing apparatus shown in FIG. 12A.
Figure 12C:
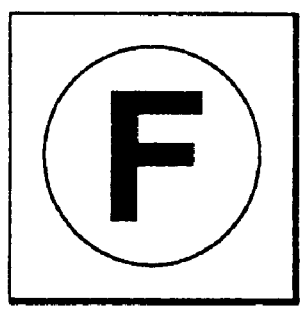
FIG. 12C is the second diagram showing an example of a display in the image processing apparatus shown in FIG. 12A.
Figure 12F:
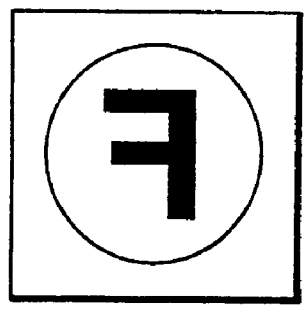
Figure 12D:
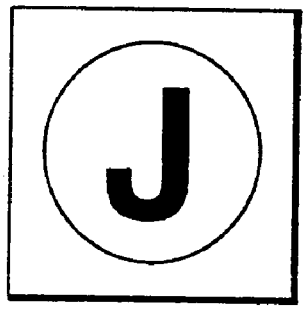
FIG. 12D is the third diagram showing an example of a display in the image processing apparatus shown in FIG. 12A.

In this embodiment, an image processing apparatus may have the circuitry shown in FIG. 12A. An image processing apparatus 8d presented as a variant supplies video signals sent from the endoscopes 2 and 2a to each of the image inverting circuit 11 and selector switch 12. Either of the video signals sent from the endoscopes 2 and 2a is fed to the image inverting circuit 11 by means of a switch 26. The image inverting circuit 11 inverts, similarly to the foregoing one, an image and supplies a processed video signal to the selector switch 12.

In response to a control signal sent from the selector 14, the selector switch 12 selects a video signal representing a raw image provided by the endoscope 2a or a video signal sent from the image inverting circuit 11 and supplies a selected video signal to the TV monitor 21.

The contents of processing to be performed by the image inverting circuit 11 and a video signal to be selected by the selector 14 are, similarly to those in the foregoing embodiment, designated using setting switched on the operation panel 15.

When the surgeon A mainly manipulates a therapeutic appliance, an image provided by the endoscope 2 is displayed on the TV monitor 21. When the back of a lesion is to be treated, if an image J provided by the endoscope 2a opposed to the surgeon A is displayed as it is, the surgeon A finds the image vertically and laterally inverse. This results in markedly deteriorated operability. In the configuration of the variant, the operation panel 15 is used to instruct the image inverting circuit 11b to display a mirror image made by laterally inverting an image provided by the endoscope 2a or an inverted image made by vertically and laterally inverting the image on the TV monitor 21.

The surgeon A can observe the image J rendering the back of the lesion, which is invisible in the image F provided by the endoscope 2, and can manipulate the therapeutic appliance without having any sense of unnaturalness.

When the surgeon B mainly manipulates the therapeutic appliance, if the back of a lesion is to be treated, a mirror image made by laterally inverting the image F provided by the endoscope 2 or an inverted image made by vertically and laterally inverting the image F is displayed on the TV monitor 21. The surgeon B can manipulate the therapeutic appliance without any sense of unnaturalness while observing the back of the lesion. The image shown in FIG. 12A is a mere example of a display. Needless to say, the images shown in FIGS. 12B to 12F can be selectively displayed on the monitor 21 using the selector switch 12 and switch 26.

Next, the fifth embodiment will be described.

The fifth embodiment is substantially identical to the first embodiment. Different components alone will be described. Identical components will be assigned the same reference numerals, of which no mention will be made.

Figure 13:
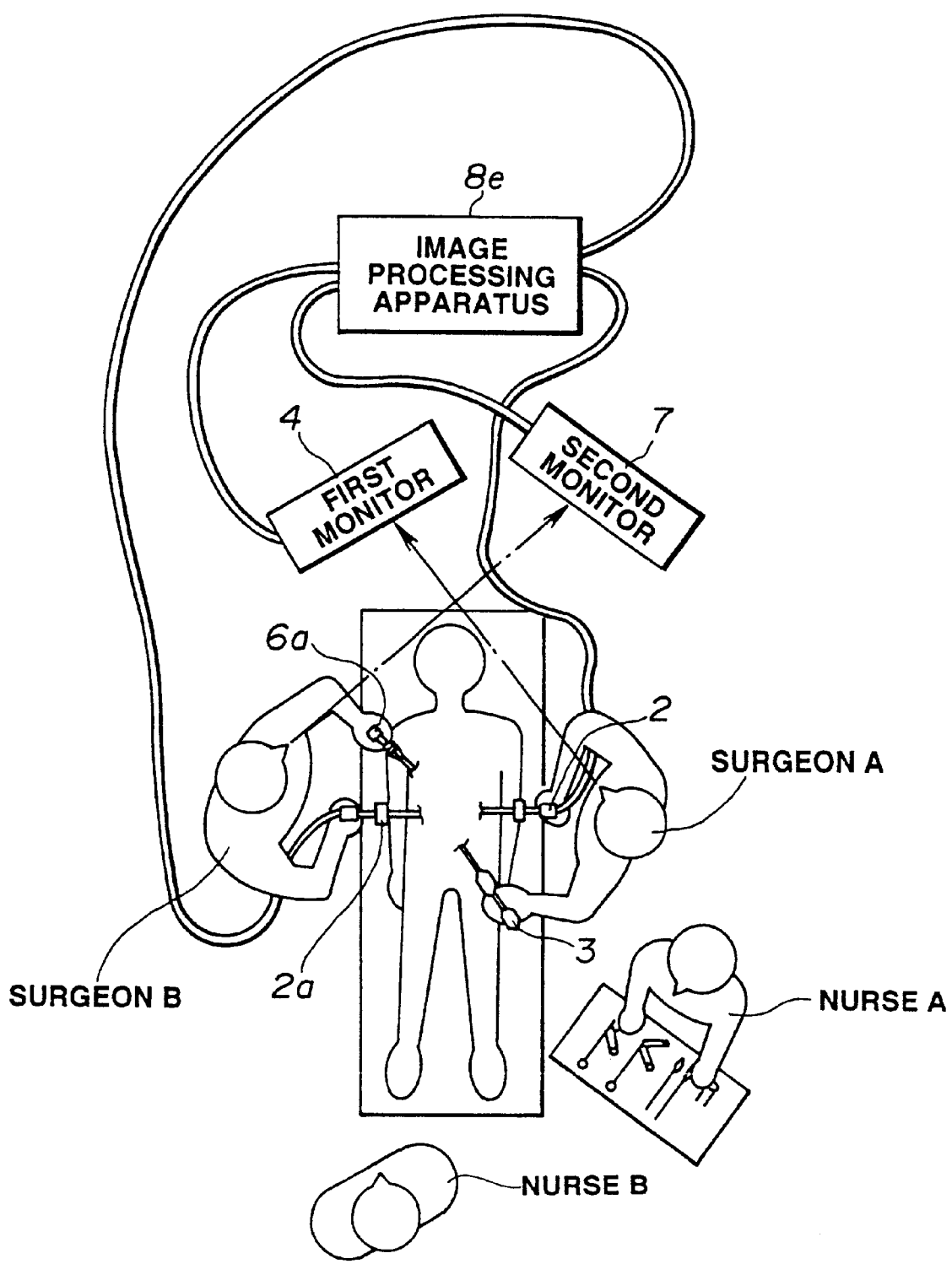

According to the fifth embodiment, as shown in FIG. 13, unlike the first embodiment, the surgeon B uses the second endoscope 2a of an endoscope system instead of the therapeutic appliance 6b and images the back of a lesion. The surgeons A and B proceed with a surgical procedure while manipulating the endoscopes 2 and 2a concurrently. An image processing apparatus 8e of the fifth embodiment receives video signals from the two endoscopes 2 and 2a, processes the signals, and supplies processed signals to the first and second monitors 4 and 7.

As shown in FIG. 14, the image processing apparatus 8e of the fifth embodiment supplies the video signals sent from the endoscopes 2 and 2a to image inverting circuits 11a and 11b and the selector switches 12 and 13. Each of the image inverting circuits 11a and 11b inverts an image, similarly to the one in the first embodiment, and supplies a processed video signal to each of the selector switches 12 and 13.

In response to a control signal sent from the selector 14, each of the selector switches 12 and 13 selects a video signal representing a raw image provided by each of the endoscopes 2 and 2a or a video signal sent from each of the image inverting circuits 11a and 11b, and supplies a selected signal to each of the first and second monitors 4 and 7.

The contents of processing to be performed by the image inverting circuits 11a and 11b, and a video signal to be selected by the selector 14 are, similarly to those in the first embodiment, designated using setting switches on the operation panel 15.

As a result, as seen from examples of displays of the first and second monitors 4 and 7, a laterally-inverted image (mirror image) of a raw image originating from the endoscope 2a manipulated by the surgeon B is displayed on the first monitor 4, and a laterally-inverted image (mirror image) of a raw image originating from the endoscope 2 manipulated by the surgeon A is displayed on the second monitor 7. The other components are identical to those in the first embodiment.

When the surgeon A mainly manipulates a therapeutic appliance, the image inverting circuit 11b displays a mirror image made by laterally inverting an image provided by the endoscope 2a or an inverted image made by vertically and laterally inverting the image on the first monitor 4, and the image inverting circuit 11a displays a mirror image made by laterally inverting an image provided by the endoscope 2 or an inverted image made by vertically and laterally inverting the image on the second monitor 7. The surgeon A can observe an image J rendering the back of a lesion, which is invisible in an image F provided by the endoscope 2, and manipulate a therapeutic appliance without having any sense of unnaturalness. The same applies to the surgeon B.

Next, the sixth embodiment will be described.

The sixth embodiment is substantially identical to the fifth embodiment except the configuration of an image processing apparatus. Different components alone will be described. Identical components will be assigned the same reference numerals, of which no mention will be made.

Figure 15A:
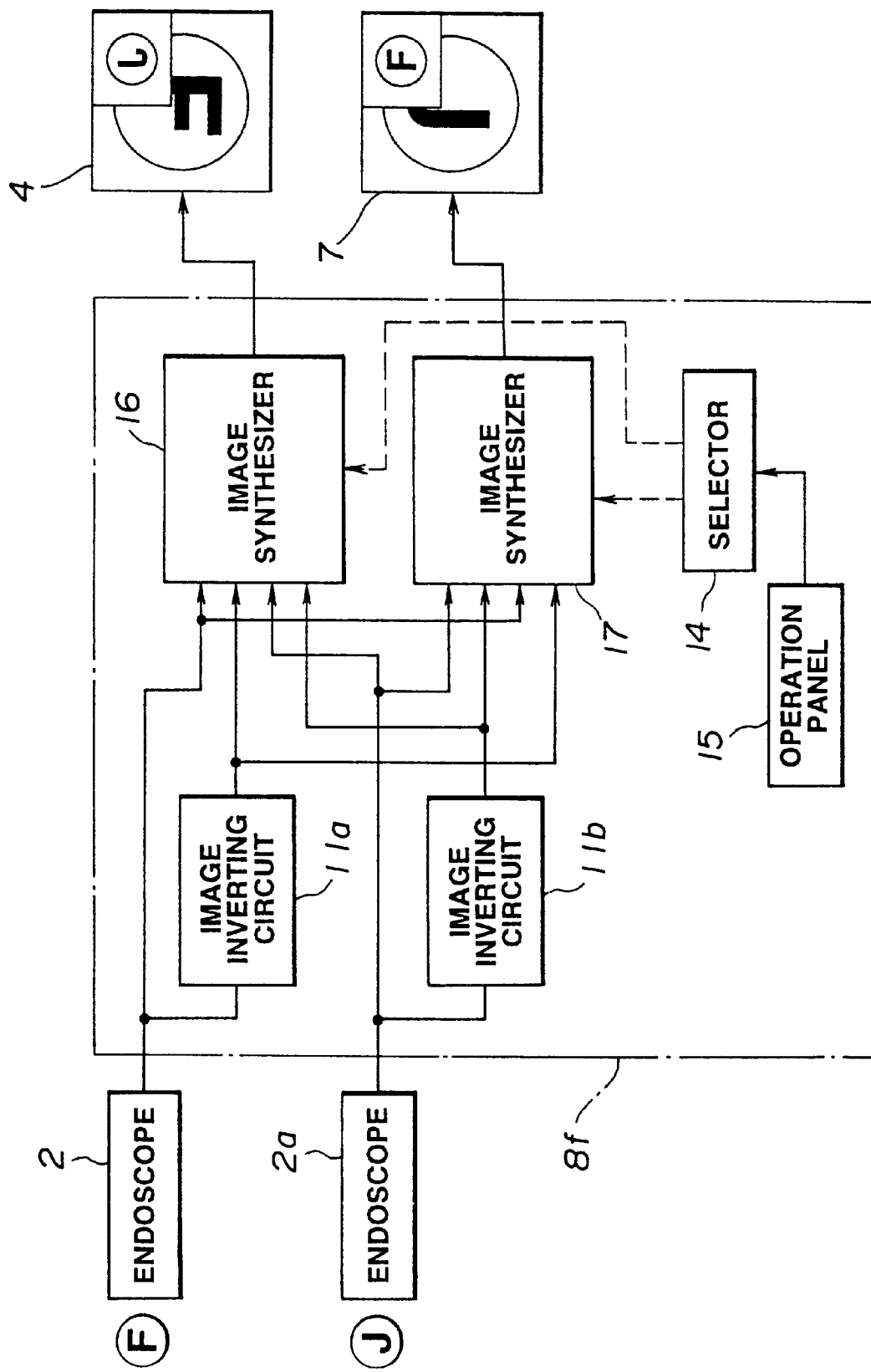
FIGS. 15A to 15C relate to the sixth embodiment of the present invention.

As shown in FIG. 15A, an image processing apparatus 8f of the sixth embodiment supplies video signals sent from the endoscopes 2 and 2a to each of the image inverting circuits 11a and 11b and the image synthesizers 16 and 17. Each of the image inverting circuits 11a and 11b inverts an image and supplies a processed video signal to each of the image synthesizers 16 and 17.

Each of the image synthesizers 16 and 17 receives a video signal representing a raw image from each of the endoscopes 2 and 2a and a image-wise inverted video signal from each of the image inverting circuits 11a and 11b. In response to a control signal sent from the selector 14, each of the image synthesizers 16 and 17 synthesizes input video signals selectively so as to produce a picture-in-picture image, and supplies a video signal representing the picture-in-picture image to each of the first and second monitors 4 and 7. A video signal to be selected by the selector 14 is, similarly to the one in the first embodiment, designated using setting switches on the operation panel 15.

Figure 15B:
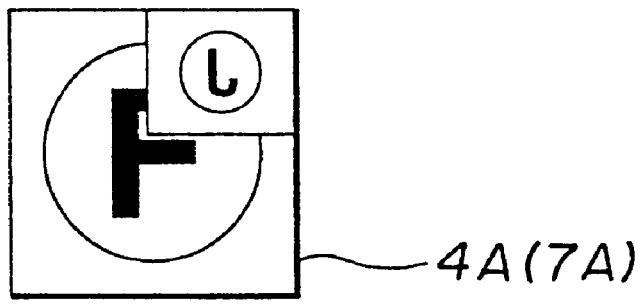
Figure 15C:
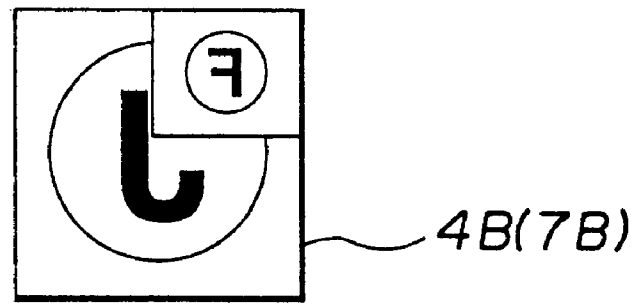

As a result, various display images (for example, an example of a display of FIG. 15A or images 4A (7A) and 4B (7B) shown in FIGS. 15B and 15C) are selectively displayed on the first monitor 4 and second monitor 7. The other components are identical to those in the fifth embodiment.

In addition to the advantage of the fifth embodiment, this embodiment has the advantage that since the surgeons A and B can observe picture-in-picture images on different monitors, they can install the monitors at easy-to-see places in easy-to-see orientations. Furthermore, since images used as main images by partners can be displayed as sub-images on the first and second monitors 4 and 7, the surgeons A and B can communicate with each other more effortlessly.

Next, the seventh embodiment will be described.

The seventh embodiment is substantially identical to the fifth embodiment. Different components alone will be described. Identical components will be assigned the same reference numerals, of which no mention will be made.

As described in conjunction with the fifth embodiment, an endoscope-aided surgical procedure has been widely adopted, wherein two endoscopes are employed concurrently in order to carry out the procedure while viewing the front and back of a lesion at a time. Incidentally, for example, an observational ultrasound system may be used to visualize a tomographic image of a body cavity in parallel with an endoscopic image. This embodiment can be adapted for this kind of application.

Figure 16:
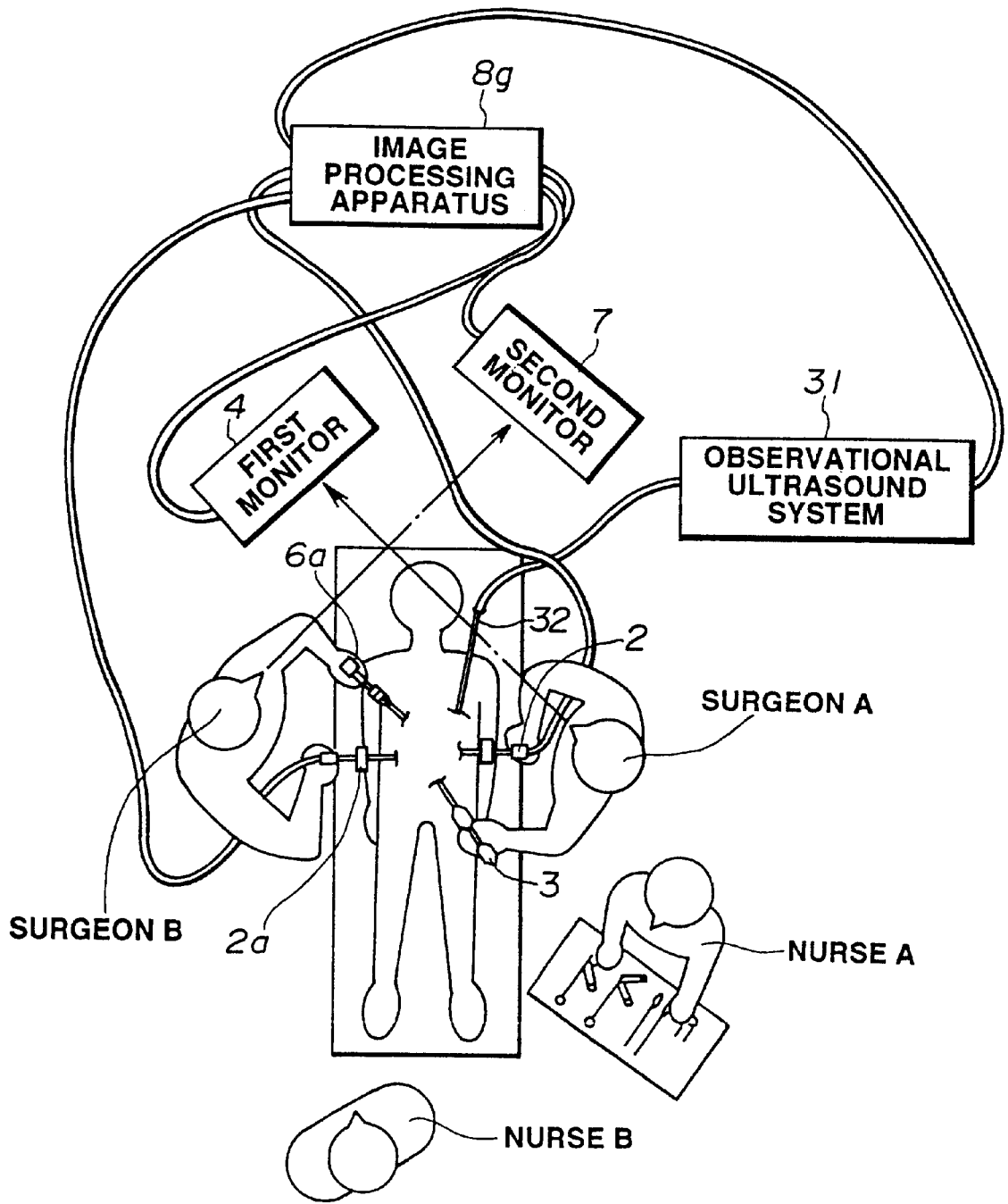
FIGS. 16 and 17 relate to the seventh embodiment of the present invention.

As shown in FIG. 16, the seventh embodiment is connected to an observational ultrasound system 31 and an ultrasound probe 32 is inserted into a body cavity. An ultrasonic image provided by the observational ultrasound system 31 is supplied to an image processing apparatus 8g. The image processing apparatus 8g processes video signals sent from the endoscopes 2 and 2a and the observational ultrasound system 31 alike.

Figure 17:
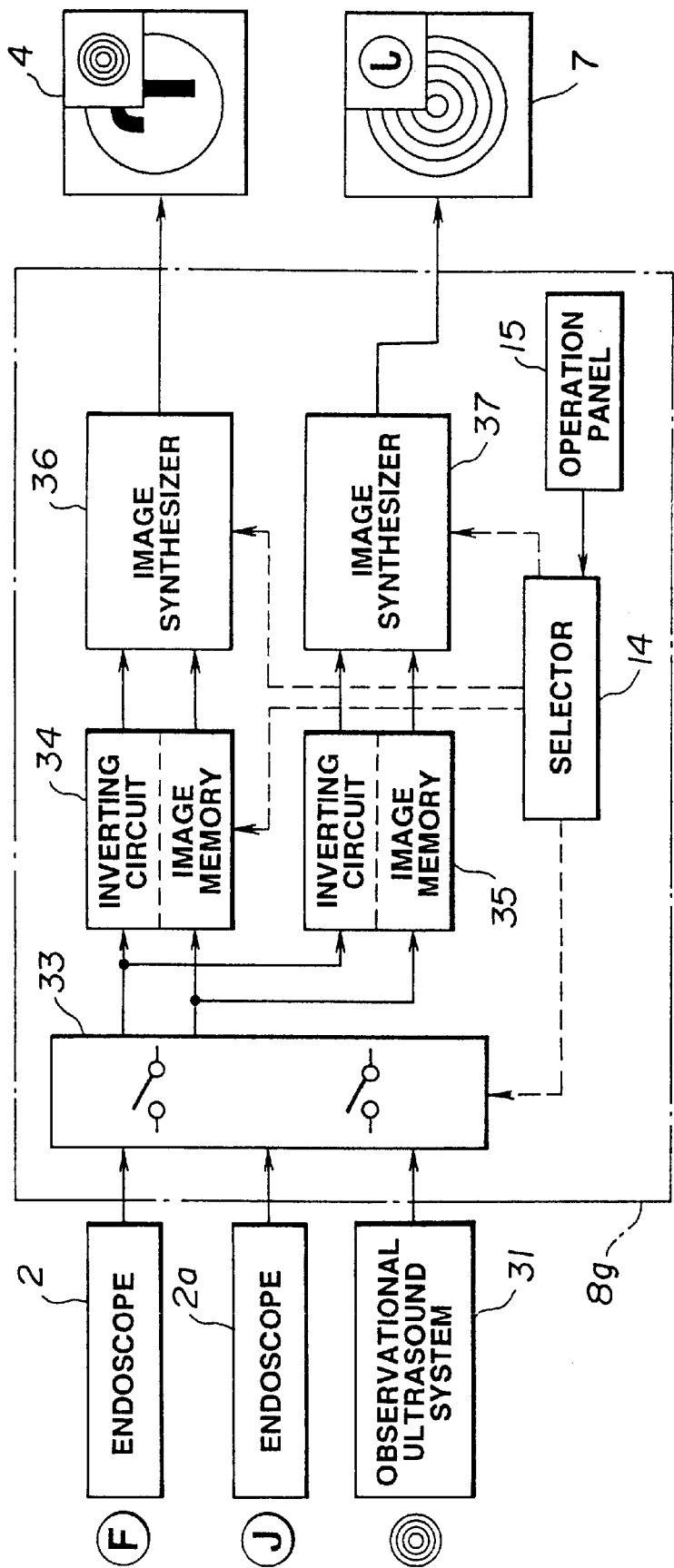

As shown in FIG. 17, the image processing apparatus 8g uses a selector switch 33 to select two video signals from among those sent from the endoscopes 2 and 2a and the observational ultrasound system 31 in response to a control signal sent from the selector 14. The selected two video signals are supplied to each of the image inverting circuits 34 and 35 that consists of an image memory and an inverting circuit. Each of the image inverting circuits 34 and 35 inverts one of the video signals, which are selected by the selector switch 33 in response to a control signal sent from the selector 14, and supplies the processed video signal and unprocessed video signal. The image inverting circuits 34 and 35 invert mutually different images. Each of the image synthesizers 36 and 37 receives the processed and unprocessed video signals from each of the image inverting circuits 34 and 35, selectively synthesizes input video signals in response to a control signal sent from the selector 14 so as to produce a picture-in-picture image, and supplies a video signal representing the picture-in-picture image to each of the first and second monitors 4 and 7. A video signal to be selected by the selector 14 is, similarly to the one in the first embodiment, designated using setting switches on the operation panel 15.

As a result, various display images are selectively displayed on the first and second monitors 4 and 7. The other components are identical to those in the fifth embodiment.

In addition to the advantage of the fifth embodiment, his embodiment has the advantage that an endoscopic image and an ultrasonic image can be seen on the same monitor. This results in improved operability and treatment efficiency. Incidentally, an observational ultrasound system usually includes a dedicated monitor so that an ultrasonic image is displayed on the dedicated monitor. A monitor for an endoscope and a monitor for an observational ultrasound system can hardly be installed side by side in an operation room because of the limited space of the room and the unique shape and usage of the observational ultrasound system. Surgeons have therefore had to view a plurality of monitors spaced apart.

Three input images are available. Merely by changing the setting of the image processing apparatus 8g, two images used as main images and sub-images appearing on the first and second monitors 4 and 7 can be selected from among the three input images. When the surgeon A mainly manipulates a therapeutic appliance, an inverted image made by vertically and laterally inverting an image provided by the endoscope 2a is displayed as a sub image on the first monitor 4. The sub image can be changed from the inverted image into an image provided by the observational ultrasound system instantaneously when needed. Moreover, the display screen can be returned to an original screen. Furthermore, an ultrasonic image can be displayed as a main image with ease. This results in improved operability.

Next, the eighth embodiment will be described.

Figure 18:
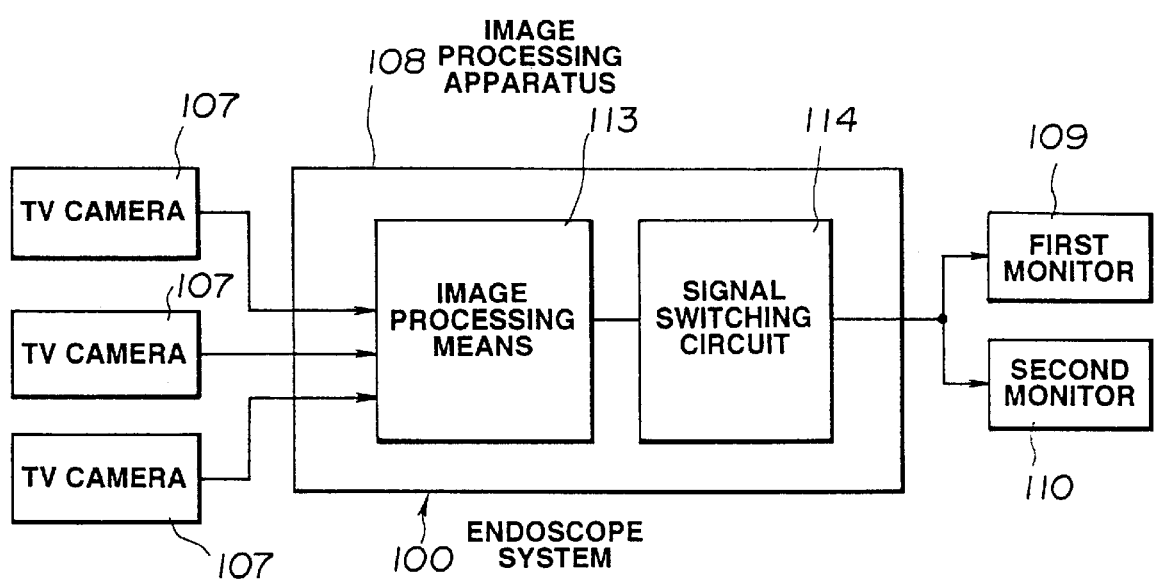

An endoscope system 100 shown in FIG. 18 comprises a plurality of TV cameras 107 (three TV cameras in FIG. 18), an image processing apparatus 108 for processing a plurality of signals picked up by the plurality of TV cameras 107 and selectively outputting processed signals, and a first monitor 109 and second monitor 110 for receiving outputs of the image processing apparatus 108 and displaying endoscopic images. The image processing apparatus 108 includes an image processing means 113 for performing various kinds of processing including synthesis and inversion which are necessary for displaying signals sent from the plurality of TV cameras 107 on the first monitor 109 and second monitor 110, and a signal switching means 114 for supplying the plurality of signals processed by the image processing means 113 selectively to the first monitor 109 and second monitor 110. The TV cameras 107 can be externally mounted on a plurality of eyepiece units of endoscopes. Hereinafter, an endoscope with a TV camera shall be referred to as merely an endoscope.

Note that an electronic endoscope having a solid-state device incorporated at the tip of an insertional part thereof may be employed instead of an endoscope with a TV camera. The present invention is not limited to the field of endoscopy. In addition to the monitors 109 and 110, a recording means such as an image VTR or an optical disk drive may be installed.

Figure 19:
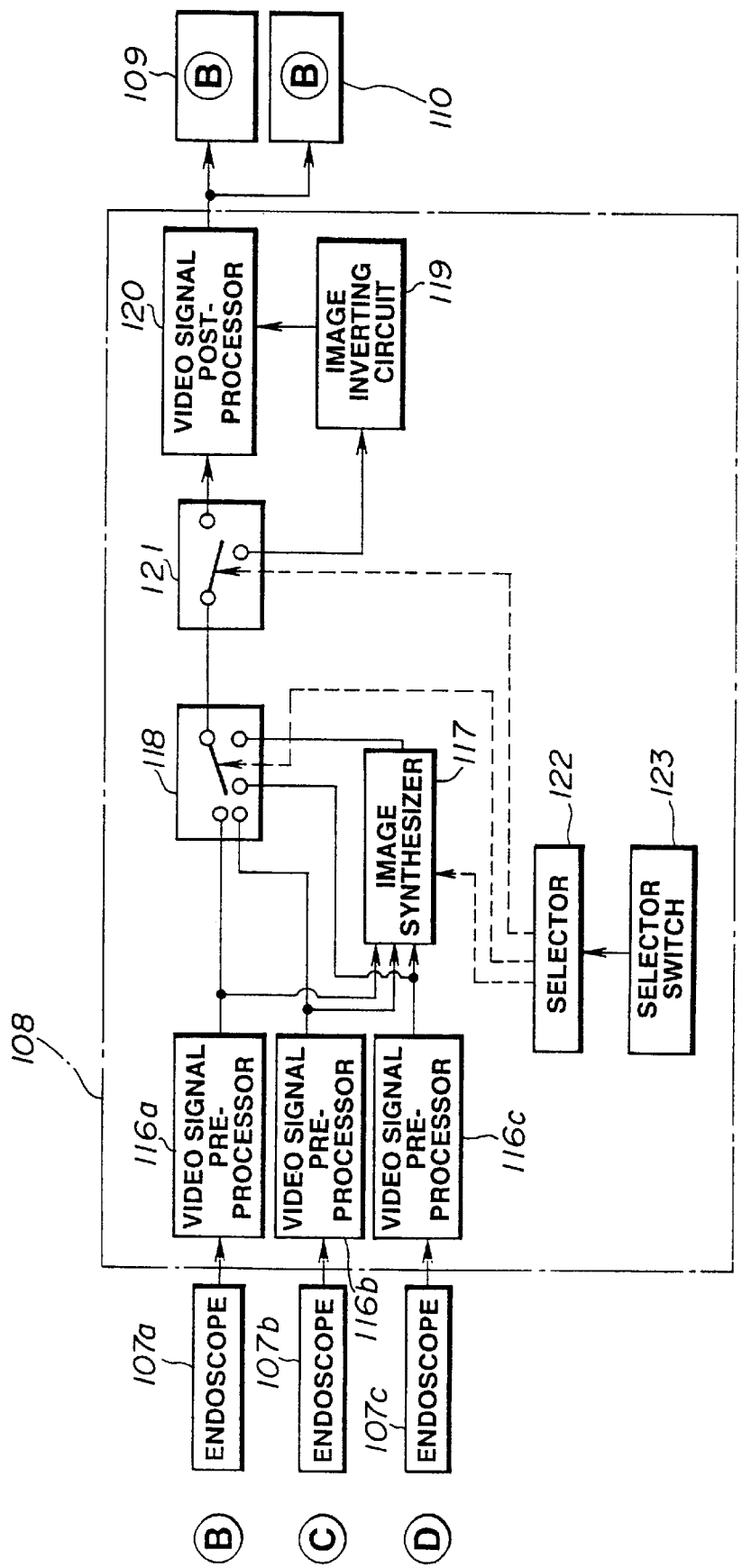

FIG. 19 shows an example of the image processing apparatus 108. In this embodiment, endoscopes 107a, 107b, and 107c visualize subjects B, C, and D in FIG. 19, perform photoelectric transform, and supply video signals. The endoscopes 107a, 107b, and 107c are connected to the image processing apparatus 108.

The image processing apparatus 108 includes video signal pre-processors 116a, 116b, and 116c for performing digital conversion or the like on video signals sent from the endoscopes 107a, 107b, and 107c, an image synthesizer 117 for selectively synthesizing video signals sent from the endoscopes 107a, 107b, and 107c, and a first signal switching circuit 118 for selectively supplying the video signals sent from the endoscopes 107a, 107b, and 107c.

The image processing system 108 includes an image inverting circuit 119 for image-wise inverting the video signals, a video signal post-processor 120 for performing conversion or the like so as to produce standard video signals compatible with the first monitor 109 and second monitor 110, a second signal switching circuit 121 for supplying an output of the first signal switching circuit 118 selectively to the image inverting circuit 119 and video signal post-processor 120, a selector 122 for controlling the image synthesizer 117, and the first and second signal switching circuits 118 and 121, and a selector switch 123 for giving an instruction of switching to the selector 122.

This embodiment will be described on the assumption that the image inverting circuit 119 produces a laterally-inverted image.

Figure 20:
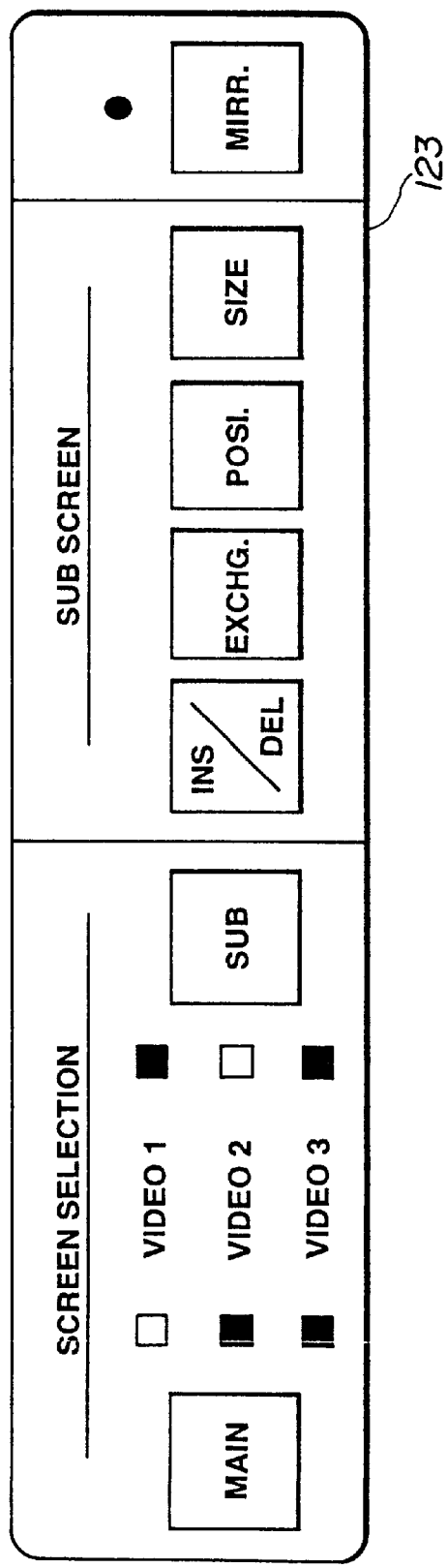

FIG. 20 shows an example of the selector switch 123. The selector switch 123 has a Screen Selection block for selecting video signals to be synthesized from among a plurality of video signals. The Screen Selection block includes a main selection switch (hereinafter, a Main switch) for selecting a main image for a synthetic image and a sub-selection switch (hereinafter, a Sub switch) for selecting a sub image for the synthetic image. Every time the Main switch is pressed, any of Videos 1 to 3 corresponding to input video signals, or in other words, any of the outputs of the endoscopes 107a to 107c is selected. A currently selected input signal is indicated with a lighting lamp adjacent to any of Videos 1 to 3. The same applies to a video signal representing a sub image. Note that Videos 1 to 3 correspond to inputs 1 to 3.

A Sub Screen block of the selector switch 123 is used to actuate various functions involving a sub image. Ins/Del denotes a switch for determining whether or not to synthesize a sub image with a main image. "Ins" means that images are to be synthesized.

Mirr denotes a switch for instructing that an image should be inverted laterally (to produce a mirror image) and displayed. In this embodiment, the switch instructs the second signal switching circuit 121 to switch signals.

Next, the modes of operation of this embodiment will be described using FIGS. 19, 20, and 21.

To begin with, a video signal fed to an input terminal shall be supplied as it is. When input 1 is selected using the Main switch in the selector switch 123, a video signal sent from the endoscope 107a is converted into a digital form by the video signal pre-processor 116a, fed to the first signal switching circuit 118, converted into an analog form by the video signal post-processor 120, and then supplied to each of the first monitor 109 and second monitor 110. In this case, a raw image that is the same as an input image, or in other words, an non-inverted image is displayed on each of the first monitor 109 and second monitor 110.

The same applies to input 2 or 3. By pressing the Main switch in the selector switch 123, an image identical to an input image is supplied to each of the first monitor 109 and second monitor 110. The Main switch may be installed for each video signal and designed to be turned on or off.

Next, image synthesis will be described.

Figure 21B:
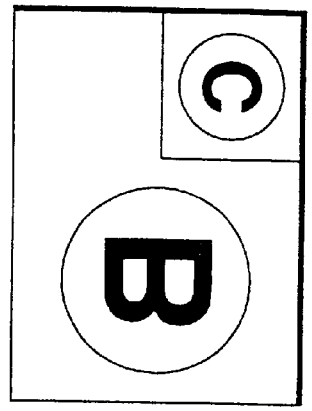
Figure 21A:
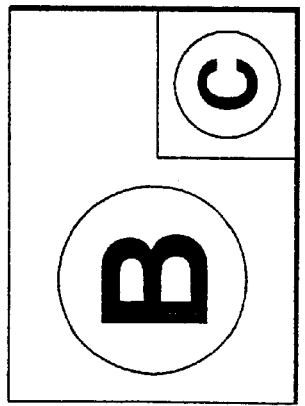
FIG. 21A is the first explanatory diagram showing a display screen on a monitor.

After the Ins/Del switch in the selector switch 123 is pressed, the Sub switch is pressed and then the Main switch is pressed. The image synthesizer 117 synthesizes inputs 1 and 2 image-wise. A synthetic signal is then fed to the first signal switching circuit 118, converted into an analog form by the video signal post-processor 120, and then supplied to each of the monitors 109 and 110. On each of the monitors 109 and 110, as shown in FIG. 21A, input 1 appears as a main image and input 2 appears as a sub image. For inverting the monitor screen laterally, the Mirr switch in the selector switch 123 is pressed. The second signal switching circuit 121 is then switched over to the image inverting circuit 119. The synthetic video signal is then inverted image-wise laterally by the image inverting circuit 119, converted into an analog form by the video signal post-processor 120, and supplied to each of the monitors 109 and 110. In this case, as shown in FIG. 21B, both the main and sub images appear inverted laterally on each of the monitors.

In this embodiment, conversion can be achieved readily by performing electrical processing without any mechanical technique. Furthermore, when a surgical procedure, examination, or any other procedure is conducted under endoscopic observation, a plurality of surgeons can see images whose view directions are consistent. Moreover, a surgeon can display and check images originating from endoscopes manipulated by other surgeon.

Owing to the forgoing configuration, during, for example, a surgical procedure, since a laterally-inverted image appears on an assistant monitor, an assistant can manipulate a therapeutic appliance or the like as instructed by a main doctor without having any sense of unnaturalness.

Next, the ninth embodiment will be described.

Figure 22:
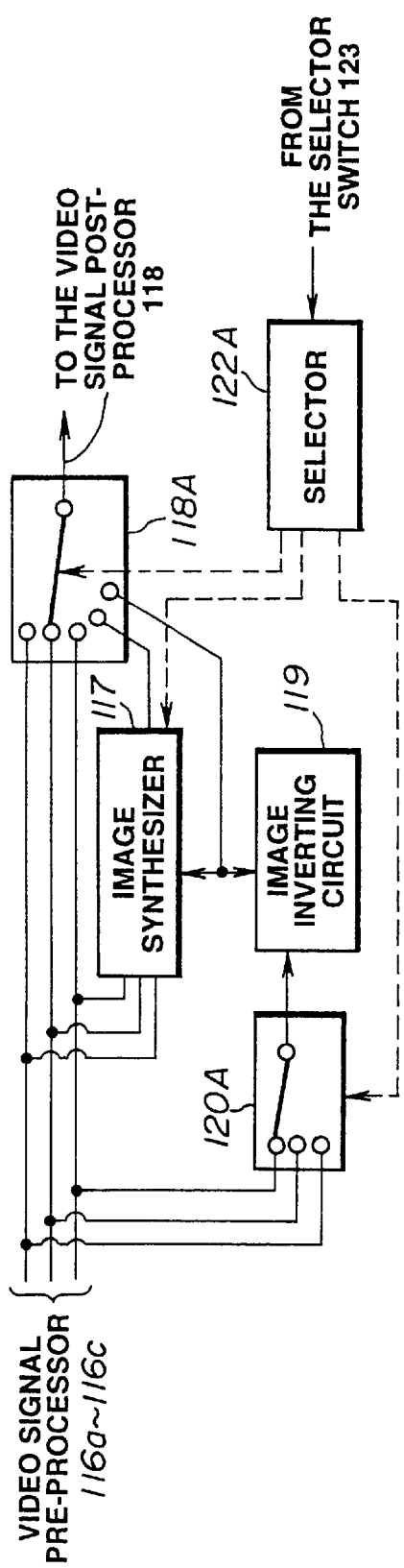
FIGS. 22 and 23B relate to the ninth embodiment of the present invention.

An image processing apparatus of this embodiment is configured so that images can be inverted selectively and independently and then synthesized. As shown in FIG. 22, the apparatus of this embodiment includes a selector 122A in place of the selector 122 in the eighth embodiment. Other components identical to those of the eighth embodiment will be assigned the same reference numerals. No mention will be made of the components as well as the modes of operation identical to those of the eighth embodiment. The difference alone will be described.

As shown in FIG. 22, outputs of the video signal pre-processors 116a to 116c are fed to each of the first signal switching circuit 118A, a second signal switching circuit 120A, and the image synthesizer 117. An output selected by the second signal switching circuit 120A is fed to each of the image synthesizer 117 and first signal switching circuit 118A via the image inverting circuit 119. The first signal switching circuit 118A selectively supplies any of raw images of inputs 1 to 3, a synthetic image or synthetic inverted image, and an inverted image.

Figure 23A:
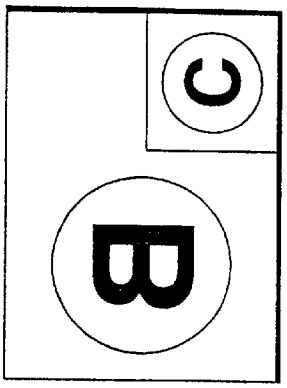
FIG. 23A is the first explanatory diagram showing an example of a display on a monitor provided by the image processing apparatus shown in FIG. 22.
Figure 23B:
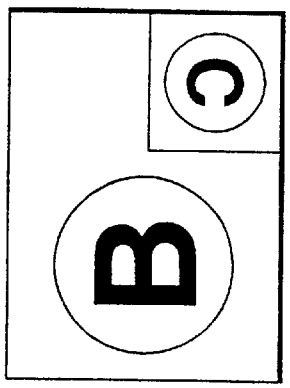

When a synthetic image is selected by pressing the Ins switch in the selector switch 123, as shown in FIG. 23A, a raw image of input 1 selected by the Main switch is displayed as a main image and a vertically and laterally inverted image (inverted image) of input 2 selected by the Sub switch is displayed as a sub image. By pressing the Mirr switch, as, for example, in FIG. 23B, a vertically and laterally inverted image (inverted image) of input 1 is displayed as a main image and a raw image of input 2 is displayed as a sub image.

In the foregoing configuration, an inverted image may be used as a main image and a raw image may be used as a sub image. Similarly to FIG. 21, only an inverted image can be displayed.

The image inverting circuit 119 may be installed for each input signal.

In this embodiment, part of a synthetic image; that is, a sub image can be inverted and displayed independently of a main image. For example, when this embodiment is adapted for an endoscope-aided surgical procedure, a surgeon standing on the opposite side of a rigid endoscope can carry out the procedure without any sense of unnaturalness while viewing a TV monitor in front of the surgeon. An image originating from the rigid endoscope the surgeon manipulates is displayed as it is, while an image originating from a rigid endoscope manipulated by other surgeon opposed to the surgeon can be inverted and displayed. When surgeons are opposed to each other, the surgeons can check a plurality of images whose view directions are consistent. This is unthinkable when the whole of a synthetic image is inverted.

Next, the tenth embodiment will be described.

Figure 24:
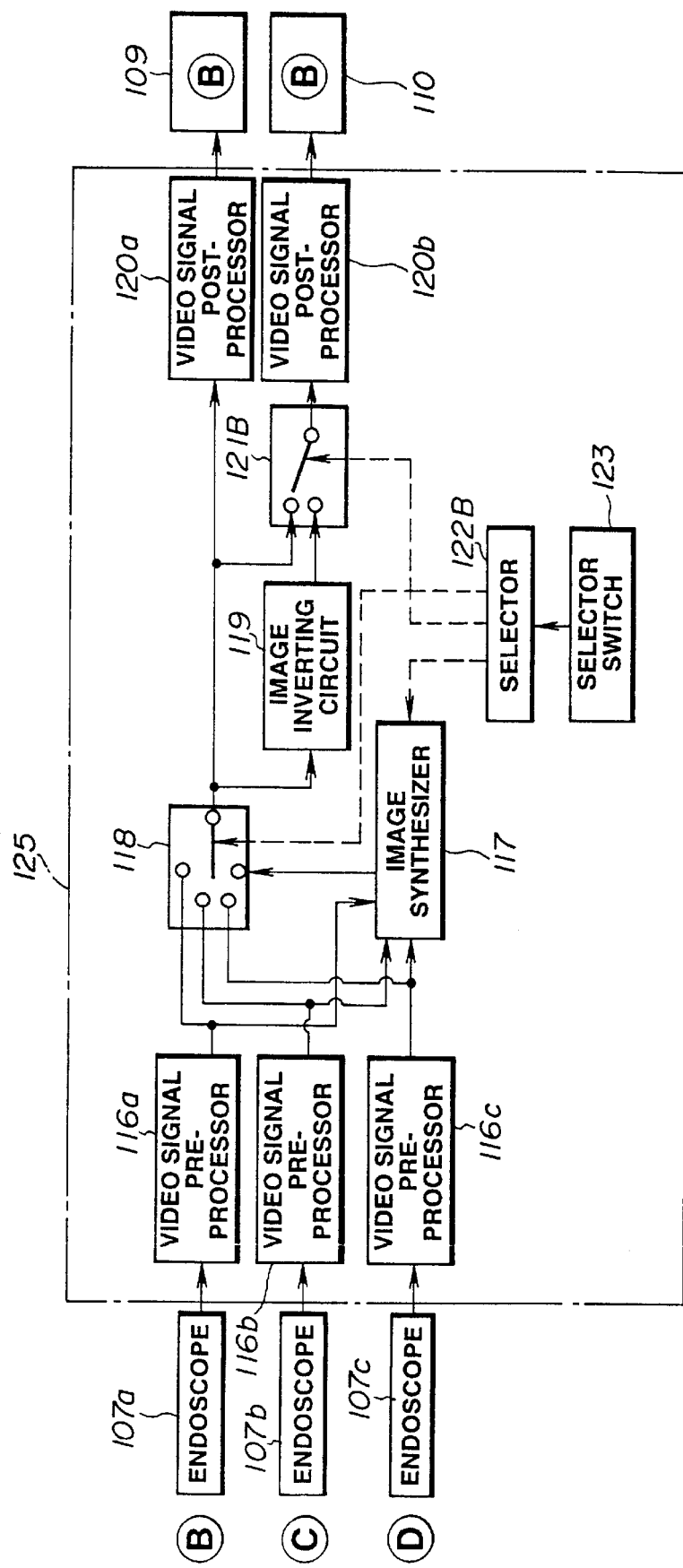

An image processing apparatus 125 of the tenth embodiment shown in FIG. 24 is configured so that only an image on the second monitor 110 is inverted. The image inverting circuit 119 receives an output selected by the first signal switching circuit 118 and supplies it to the second signal switching circuit 121B. The second signal switching circuit 121B selectively supplies an output selected by the first signal switching circuit 118 and an output inverted by the image inverting circuit 119 to the second monitor 10 via the image signal post-processor 20B.

The first monitor 109 displays an output selected by the first signal switching circuit 118 via the video signal post-processor 120a. The image processing apparatus of this embodiment includes a second signal switching circuit 121B and a selector 122B instead of the second signal switching circuit 121 and selector 122 in the eighth embodiment.

Other components identical to those of the eighth embodiment will be assigned the same reference numerals. No mention will be made of the components and the modes of operation identical to those of the eighth embodiment.

To begin with, the foregoing configuration will be described on the assumption that a video signal fed to an input terminal is supplied as it is. When input 1 is selected by pressing the Main switch in the selector switch 123, a video signal sent from the endoscope 107a is converted into a digital form by the video signal pre-processor 116a, fed to the first signal switching circuit 118, converted into an analog form signal by the video signal post-processor 120a, and supplied as a first monitor output signal to the first monitor 109.

The video signal is fed to the first signal switching circuit 118, and inverted image-wise laterally (to produce a mirror image) by the image inverting circuit 119. When the second signal switching circuit 121B is switched over to the image inverting circuit 119, the inverted video signal is converted into an analog form by the video signal post-processor 120b dedicated to the second monitor, and supplied to the second monitor 110. In this case, a raw image is displayed on the first monitor 109, while a laterally-inverted image is displayed on the second monitor 110. The same applies to inputs 2 and 3. By pressing the Main switch in the selector switch 123, a raw image and a laterally-inverted image is supplied to the first monitor 109 and second monitor 110 respectively.

Next, image synthesis will be described.

After the Ins/Del switch in the selector switch 123 is pressed, the Sub switch is pressed and then the Main switch is pressed. Inputs 1 and 2 are synthesized image-wise by the image synthesizer 117. When the first signal switching circuit 118 is switched over to the image synthesizer 117, the synthetic video signal is converted into an analog form by the video signal post-processor 120a and then supplied to the first monitor 109. In this case, an image shown in FIG. 25C is displayed on the monitor 109. FIG. 25C is a synthetic raw image made up of inputs 1 and 2. At this time, as shown in FIG. 25D, an image having an inverted sub image is displayed on the second monitor 110.

In the above circumstances, for laterally inverting the image on the second monitor 110, the Mirror switch in the selector switch 123 is pressed. The second signal switching circuit 121B is then switched over to the image inverting circuit 119, whereby the synthetic video signal is converted into an analog form by the video signal post-processor 120*b*, and supplied to the second monitor 110. In this case, the second monitor 110 shows an image as shown in FIG. 25F. That is to say, a synthetic inverted image made up of inputs 1 and 2 is displayed. At this time, as shown in FIG. 25E, an image identical to the one shown in FIG. 25C is displayed on the first monitor 109.

FIG. 25A shows a raw image of input 1 appearing on the first monitor 109. FIG. 25B shows an inverted image of input 1 appearing on the second monitor 110. At this time, non-synthesis is selected using the Ins/Del switch in the selector switch 23.

This embodiment is configured so that synthesis, inversion, or non-inversion can be specified for the second monitor 110 independently of the first monitor. Unlike the eighth embodiment, a whole monitor screen will not be inverted. In other words, images suitable for monitor observers or positions of surgeons can be displayed on the monitors. The other components and the modes of operation and advantages are identical to those of the eighth embodiment, of which description will be omitted.

Next, the eleventh embodiment will be described.

Figure 26A:
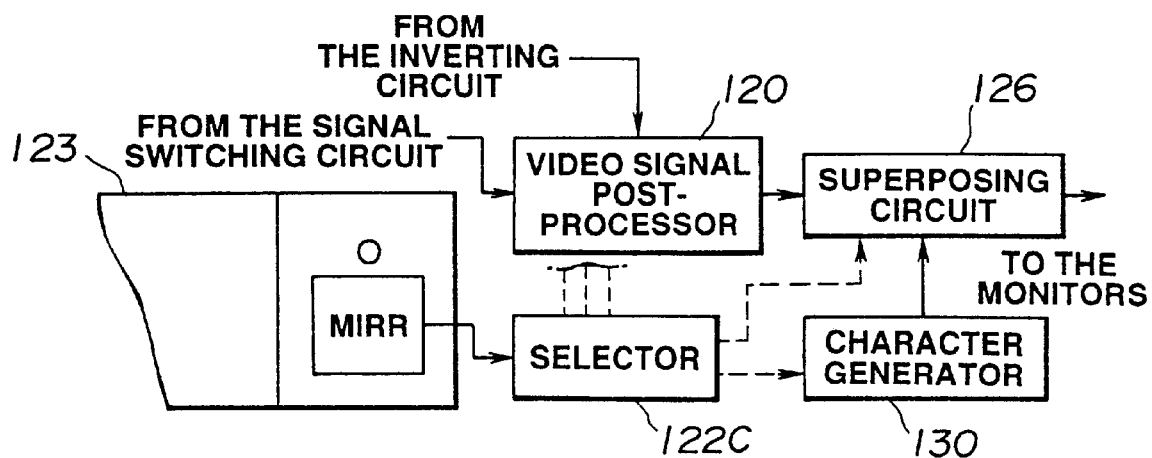
FIGS. 26A and 26B relate to the eleventh embodiment of the present invention.

An image processing apparatus of the eleventh embodiment shown in FIG. 26A has a component for superposing characters in addition to the components of the eighth embodiment. This image processing apparatus includes a superposing circuit 126 for superposing characters generated by a character generator 130 on an output signal of the video signal post-processor 120. The character generator 130 and superposing circuit 126 generate and superpose predetermined characters in response to an instruction sent from a selector 122C substituting for the selector 122. The components and modes of operation identical to those of the eighth embodiment will not be described. Differences alone will be described.

Figure 26B:
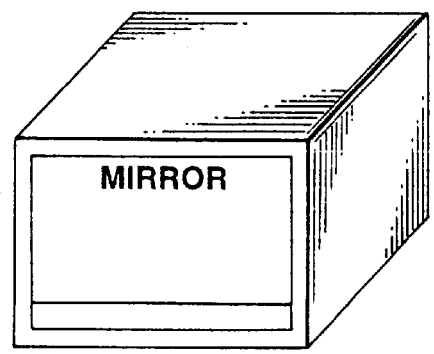

In the foregoing configuration, when the Mirr switch in the selector switch 123 shown in FIG. 26A is pressed, a symbol or characters meaning a laterally-inverted image are superposed on a laterally-inverted image on a monitor. For example, as shown in FIG. 26B, characters "MIRROR" are displayed. Alternatively, an area may be defined and changed in color.

In this embodiment, the superposing circuit is installed in a stage succeeding the image inverting circuit. It can therefore be avoided that characters are inverted on a monitor and become illegible. When the superposing circuit is installed in a stage preceding the image inverting circuit, inverted characters should be generated.

The other components and modes of operation identical to those of the eighth embodiment will not be described.

FIG. 27A is an explanatory diagram showing an image displayed on a monitor in accordance with the first variant of the eleventh embodiment.

This variant has substantially the same components as the eleventh embodiment. The modes of operation alone are different from those of the eleventh embodiment. No mention will be made of the identical components.

In this variant, characters to be generated are changed in size with the passage of time. Immediately after a symbol or characters meaning a laterally-inverted image are displayed on a monitor on which a laterally-inverted image appears, the symbol or characters are large in size as shown in FIG. 27A. When a given period of time has elapsed, as shown in FIG. 27B, the symbol or characters get smaller. This is intended to minimize a vignetted portion of an endoscopic image. Alternatively, the symbol or characters may be deleted when a given period of time has elapsed.

Figure 29A:
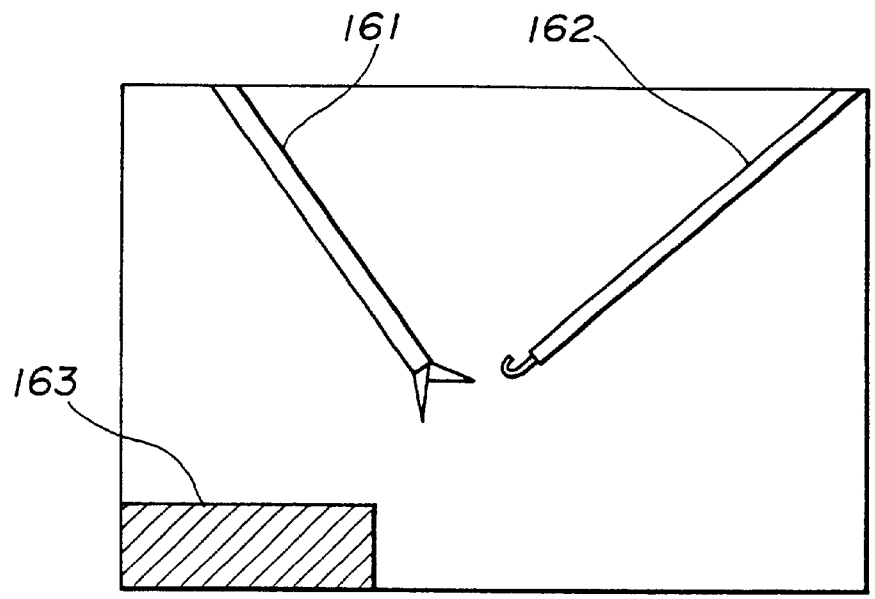
FIGS. 29A and 29B are explanatory diagrams showing display screens on monitors provided by the image processing apparatus shown in FIG. 28.
Figure 29B:
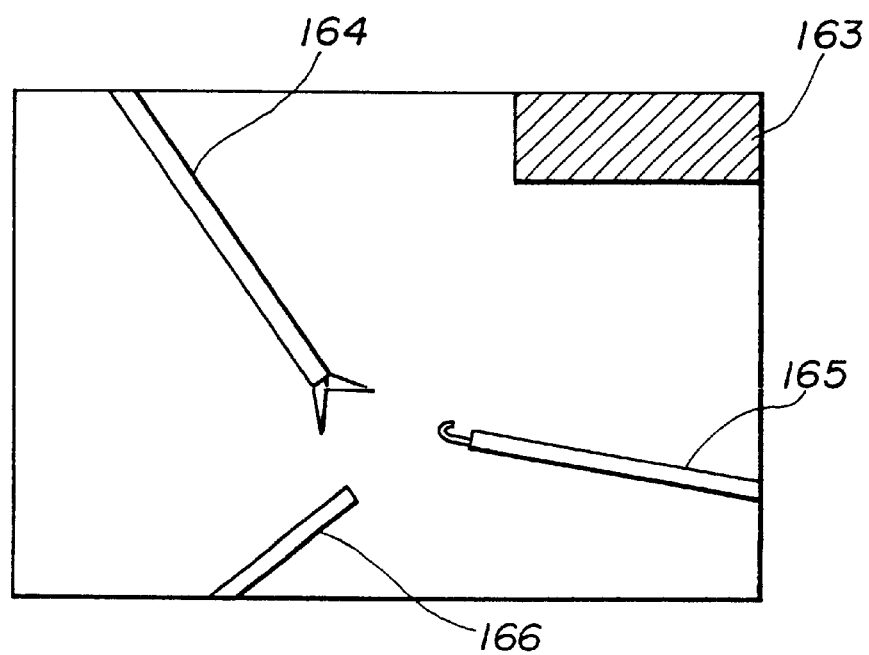

FIGS. 28 to 29B relate to the second variant of the eleventh embodiment. FIG. 28 shows a configuration of an image processing apparatus. FIG. 29A is the first explanatory diagram showing an image displayed on a monitor by the image processing apparatus shown in FIG. 28. FIG. 29B is the second explanatory diagram showing an image displayed on a monitor by the image processing apparatus shown in FIG. 28.

In an image processing apparatus 153, an endoscope 151 is inserted into a body cavity in order to image a region of view and to treat a lesion using a therapeutic appliance, an endoscopic image provided by the endoscope 151 is picked up by a TV camera 152 mounted on an eyepiece unit, and a picked-up image is processed and synthesized with a character image. As shown in FIG. 28, the image processing apparatus 153 comprises an image synthesizer 155 for synthesizing an endoscopic image with a character image provided by a character generator 154, and a position detector 156 for transmitting an endoscopic image to the image synthesizer 155 and detecting a position of a therapeutic appliance in the endoscopic image. A synthetic image is displayed on a monitor 157.

FIGS. 29A and 29B show examples of displays made by synthesizing character images on endoscopic images and displayed on the monitor 157. As shown in FIG. 29A, when therapeutic appliances 161 and 162 appear extending from above to the center of the monitor 157, the position detector 156 detects the positions of the therapeutic appliances 161 and 162. The image synthesizer 155 positions a character image indicated as a hatched area at the left lower corner of the monitor 157 and synthesizes it with an endoscopic image. When therapeutic appliances 164, 165, and 166 appear as shown in FIG. 29B, the image synthesizer 155 positions a character image 163 at the right upper corner of the monitor 157 and synthesizes it with the endoscopic image. Position detection executed by the position detector 156 is achieved by sampling linear portions of therapeutic appliances (161, 162, 164, 165, and 166) through image processing. Another technique of position detection is such that colors of therapeutic appliances (in an image of a body cavity, colors of therapeutic appliances are outstandingly different from those of others) are recognized through image processing or temperatures of therapeutic appliances are recognized using a temperature sensor.

The positions of therapeutic appliances in an endoscopic image are thus detected, whereby a character image can be displayed at a position at which the character image does not overlap the endoscopic image rendering the therapeutic appliances. Consequently, an optimal endoscopic image can be offered to a surgeon all the time.

Next, the twelfth embodiment will be described.

Figure 30:
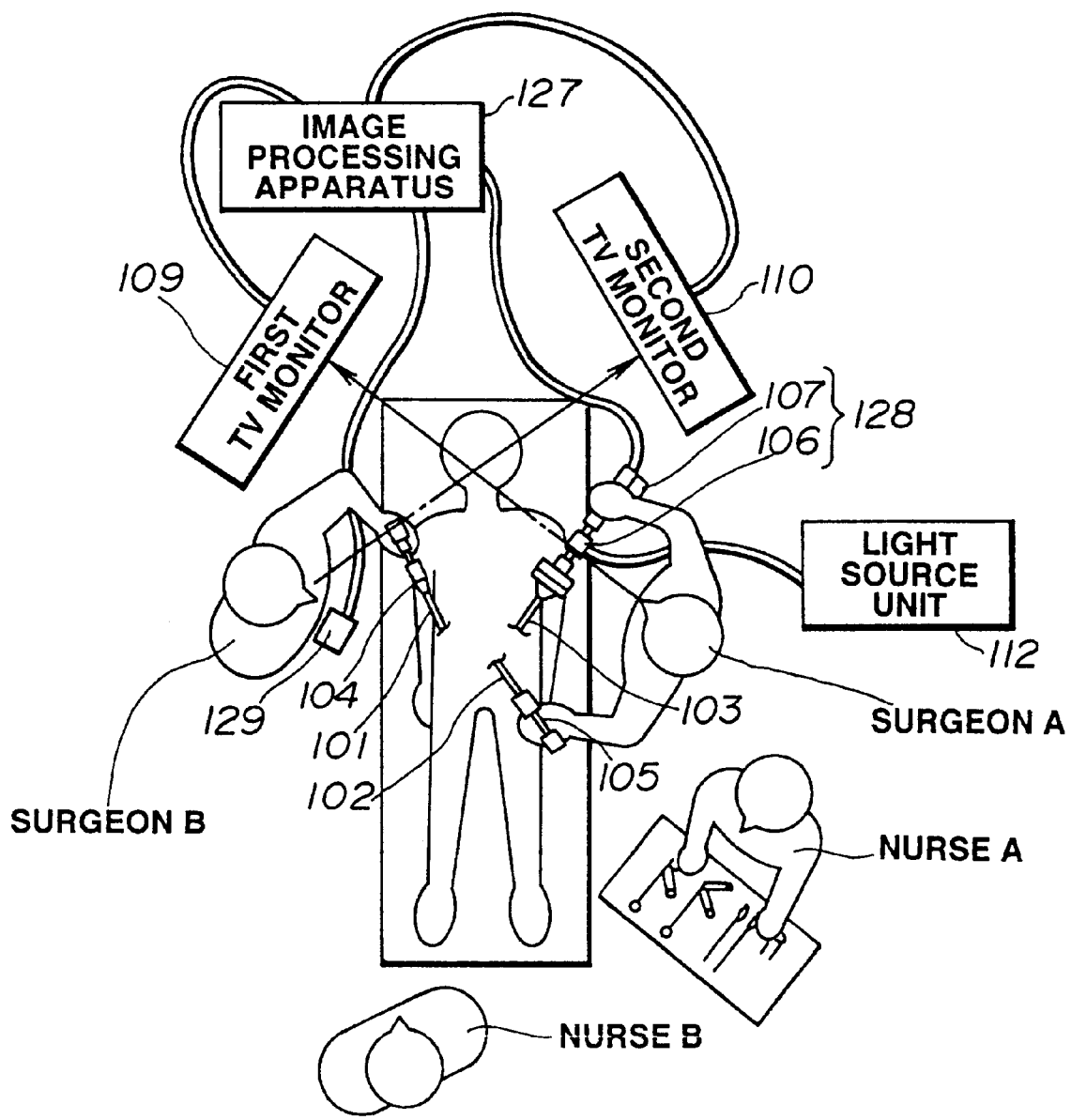
FIG. 30 shows an overall configuration of an image processing apparatus in accordance with the eleventh embodiment of the present invention.

FIG. 30 shows an operation room, in which a surgical procedure is in progress under endoscopic observation, from above. In the twelfth embodiment, surgeons A and B have inserted therapeutic appliances 104 and 105 and a rigid endoscope 106 into a body cavity using trocars and cannulas 101, 102, and 103 having pierced the wall of the body cavity. A video signal sent from a TV camera 107 mounted on an endoscope 106, which will be referred to as an endoscope 128 with a TV camera, is fed to an image processing apparatus 127 and then displayed on each of first and second monitors 109 and 110. The first monitor 109 is viewed mainly by the surgeon A, while the second monitor 110 is viewed mainly by the surgeon B.

The surgeon A holds the endoscope 128 with a TV camera and the therapeutic appliance 105, and carries out a surgical procedure while viewing the first monitor 109. The surgeon B holds the therapeutic appliance 104 and carries out the procedure while viewing the second monitor 110.

The endoscope 106 is connected to a light source unit 112 via a light guide cable 111 and thus supplied illumination light. An image provided by the endoscope 106 is sent to the image processing apparatus 127. A video signal processed by the image processing apparatus 127 is sent to each of the first monitor 109 and second monitor 110 and then visualized.

Assume that the image processing apparatus 127 operates similarly to the one shown in FIG. 24. A foot switch 129 functioning similarly to the Mirr switch in the selector switch 123 is installed at the foot of the surgeon B. The Mirr foot switch 129 is turned on or off, thus enabling or disabling lateral inversion for the second monitor 110. The Mirr switch 129 may be installed in the therapeutic appliance 104, and, if necessary, may also be installed in the endoscope 128 with a TV camera.

In the foregoing configuration, when an image provided by the endoscope 128 with a TV camera is visualized as it is, the surgeon B viewing the second monitor 110 finds the image laterally inverse to an actual scene. The image processing apparatus 127 is therefore used to display a mirror image by laterally inverting the image on the second monitor 110. However, depending on the position of the second monitor 110 or surgeon B, it is unnecessary to display a mirror image (laterally-inverted image) on the second monitor 110. The Mirr foot switch 129 is therefore helpful in specifying lateral inversion or non-inversion for the image processing apparatus 127.

In this embodiment, a mirror image is displayed on the second monitor 110 so that the surgeon B will not have a laterally-inverted view during a surgical procedure and can turn on or off generation of a mirror image using a foot (hand). A raw image (erect image) can be switched to an inverted image (mirror image) or vice versa for the second monitor 110 readily. A surgeon need not move to the image processing apparatus 127 but can observe a mirror image whenever he/she needs it.

Next, the thirteenth embodiment will be described. The thirteenth embodiment is substantially identical to the twelfth embodiment. Different components alone will be described.

Figure 31:
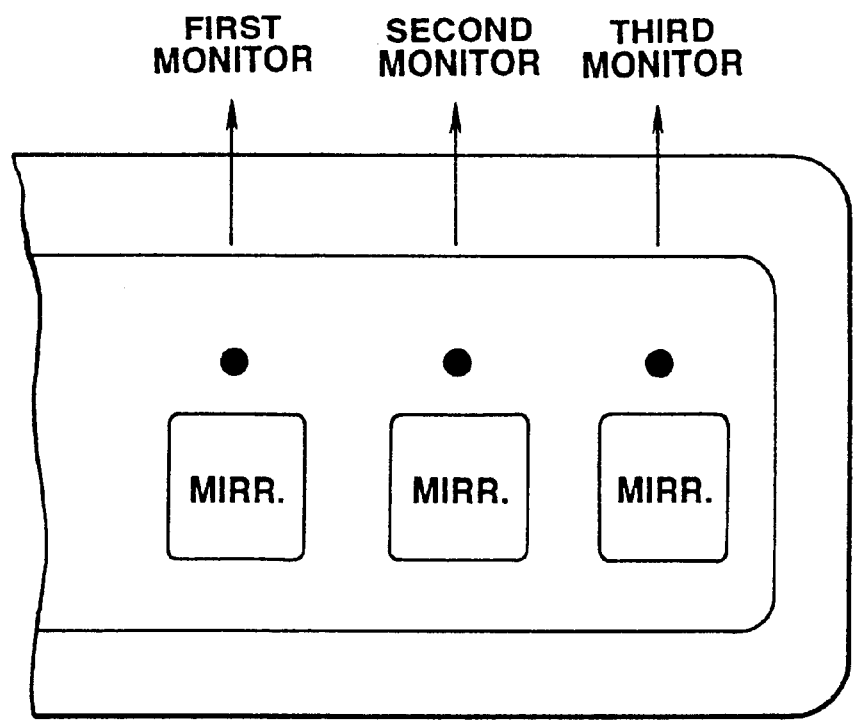
FIG. 31 is an explanatory diagram concerning a layout of a selector switch in accordance with the thirteenth embodiment of the present invention.

An image processing apparatus of the thirteenth embodiment includes a plurality of monitors (the number of monitors is, for example, three similarly to the one in the twelfth embodiment). As seen from FIG. 31 showing an operation panel of the image processing apparatus, even when a plurality of monitors are included, an erect image or a mirror image can be specified independently for each of the monitors. The image processing apparatus has, for example, the configuration shown in FIG. 24 from which the second signal switching circuit 120B is excluded. The image inverting circuit 119 is installed for each input. The outputs of the image inverting circuits and a synthetic output are switched by a first signal switching circuit.

The configuration of this embodiment is adaptable for an endoscope system including two monitors; such as, the one described in conjunction with the eighth embodiment.

Owing to the foregoing configuration, even when the positions of the surgeons A and B and monitors are different from those in FIG. 30, the surgeons will not have laterally-inverted views during a surgical procedure. Moreover, since an erect image can be switched to a mirror image or vice versa independently for each of the monitors, a mirror image can be displayed whenever needed.

For example, for an endoscope system having three or more monitors, an image processing apparatus is designed to include a multiplexer in place of the second signal switching circuit 121B shown in FIG. 24 and to supply an output of the multiplexer selectively to three video signal post-processors that supply signals to three monitors respectively. The switching of the multiplexer is achieved according to an instruction sent from any of three Mirr switches shown in FIG. 31. Note that the number of monitors is not limited to three but may be four or more.

Owing to the foregoing configuration, even when the positions of the surgeons A and B or monitors are different from those shown in FIG. 30, a surgeon will not have a laterally-inverted view during a surgical procedure. Furthermore, since an erect image or a mirror image can be specified independently for each of monitors, the monitors can be set optimally in compliance with the situation in the field.

Next, the fourteenth embodiment will be described.

Figure 32:
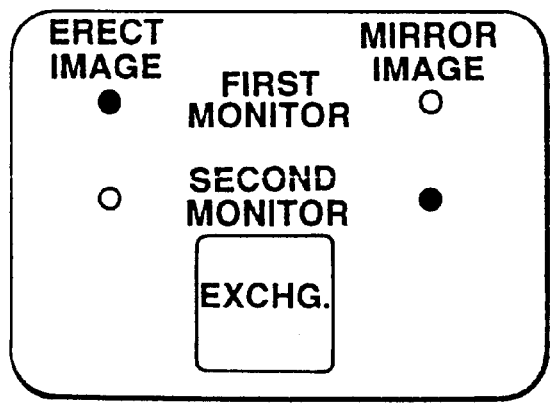
FIG. 32 shows a layout of a selector switch in accordance with the fourteenth embodiment of the present invention.

The configuration of the fourteenth embodiment is substantially identical to that of the twelfth embodiment. Surgeons and monitors shall be stationed as shown in FIG. 30. When the first monitor 109 displays an erect image and the second monitor 110 displays a mirror image, the surgeon B but not A shall hold the endoscope 128 with a TV camera. In this situation, both the surgeons A and B have laterally-inverted views. This embodiment includes, as shown in FIG. 32, a switch for exchanging an erect image for a mirror image for each of the first monitor 109 and second monitor 110. The other components identical to those of the twelfth embodiment will be assigned the same reference numerals. No mention will be made of the components as well as the modes of operation identical to those of the twelfth embodiment.

This embodiment can eliminate a nuisance of switching an erect image to a mirror image or vice versa for each of the first monitor 109 and second monitor 110.

A variant of the fourteenth embodiment relates to a system configuration including three or more monitors. The image processing apparatus 127 has an Exchange switch for switching an erect image to a mirror image or vice versa for a selected monitor alone.

This configuration enables elimination of a nuisance of switching a normal image to a mirror image or vice versa for each monitor.

Next, the fifteenth embodiment will be described.

Figure 33A:
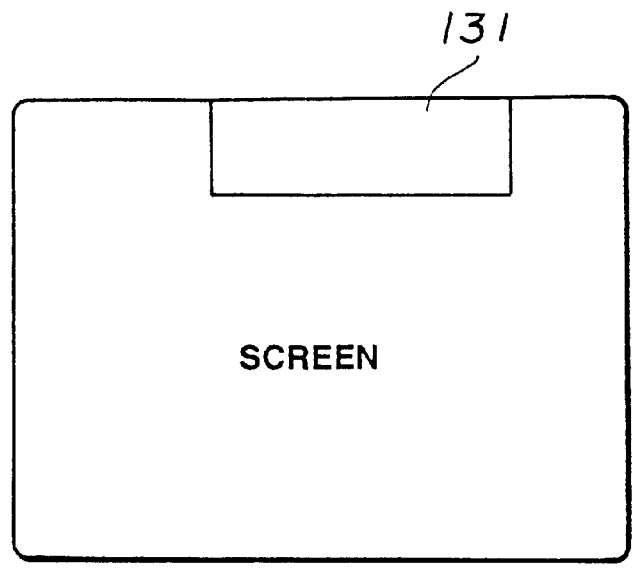
FIGS. 33A and 33B relate to the fifteenth embodiment of the present invention.
Figure 33B:
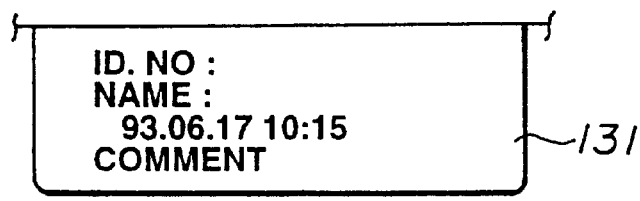

A configuration of the fifteenth embodiment is substantially identical to the one of the twelfth embodiment. A character input unit that is not shown is connected to the image processing apparatus 127. Each of the first monitor 109 and second monitor 110 has a screen shown in FIG. 33A in which character data 131 that is patient data shown in FIG. 33B is superposed on an image.

When a mirror image is produced by processing the screen on the second monitor 110, the character data 131 in the screen is also inverted. This embodiment is therefore provided with a function of deleting character data only from a mirror image. For example, an area of a screen to which character data is allocated is re-inverted.

In this configuration, when a mirror image is produced, the character data 131 will not be inverted and therefore not become illegible. When the mirror image is changed to an erect image, the character data 131 becomes legible. Alternatively, an inverting circuit may be installed in a succeeding stage, similarly to the one in the eleventh embodiment, for the purpose of superposition of character data.

A variant of this embodiment may have such a function that when a mirror image is produced, does not invert an area of a screen to which character data 131 is allocated. Alternatively, superposed character data may be supplied selectively to a monitor and a VTR (for example, when character data is patient data, it may be supplied only to the VTR but not to the monitor. When character data indicates a state of an image, it may be supplied only to the monitor but not to the VTR).

Next, the sixteenth embodiment will be described.

Figure 34:
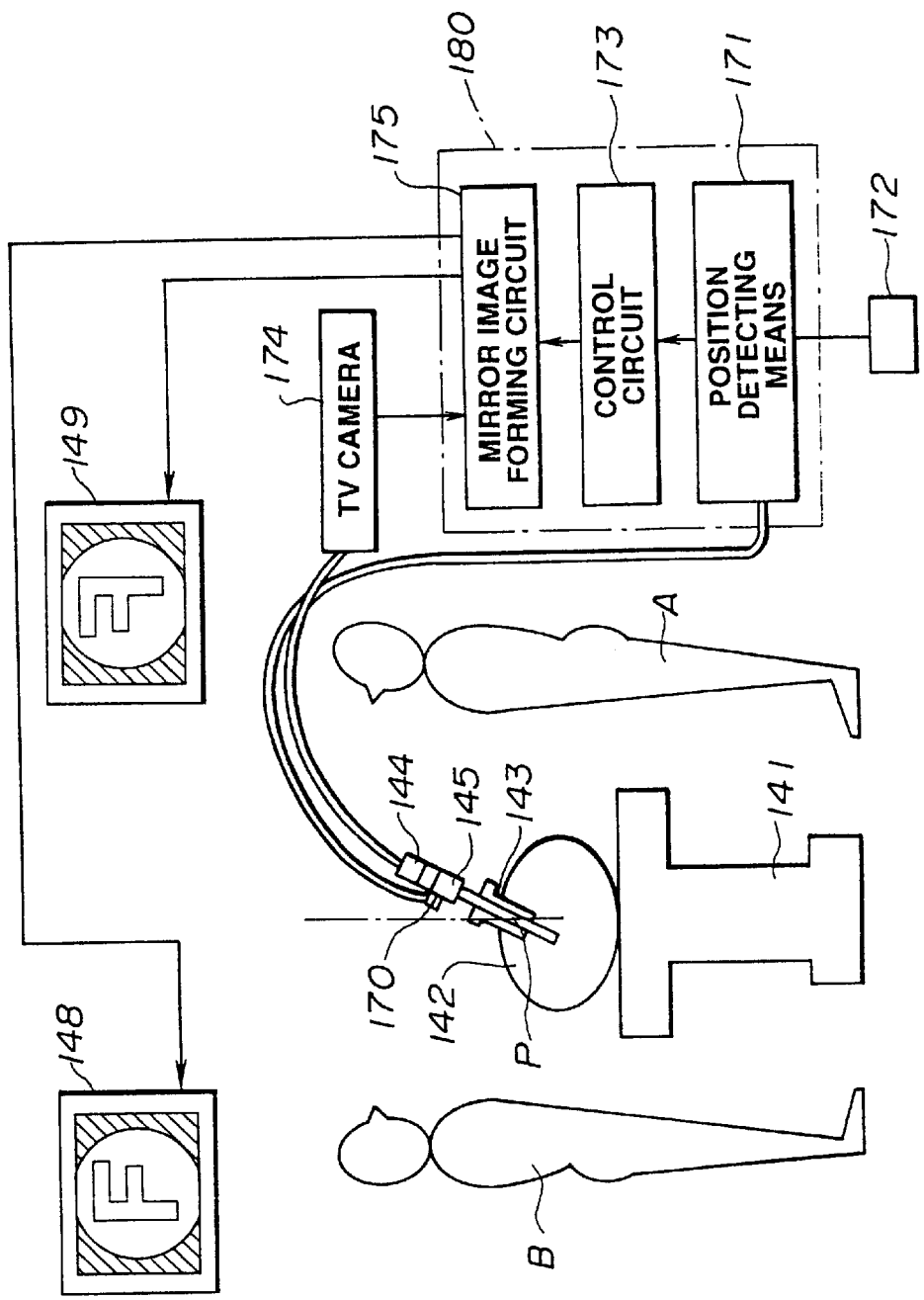
FIG. 34 shows an overall configuration of an endoscope system in accordance with the sixteenth embodiment of the present invention.

In the sixteenth embodiment, as shown in FIG. 34, an endoscope 145 to which a TV camera head 144 is connected is inserted to the abdominal cavity of a patient 142 lying on an operation table 141 using a trocar and cannula 143. Surgeons A and B standing with the operation table 141 between them manipulate forceps or the like, which are not shown, inserted to the abdominal cavity for treatment while viewing a first monitor 148 and a second monitor 149 respectively which are opposed to each other.

A position sensor 170 is mounted on the endoscope 145 or TV camera head 144. Position information provided by the position sensor 170 is detected as information indicating a position three-dimensionally relative to a receiver 172 by a position detecting means 171. The position detecting means is based on, for example, three orthogonal magnetic fields.

Position information provided by the position sensor 170 is fed to a control circuit 173. A video signal sent from a TV camera controller 174 for processing a signal sent from the TV camera head 144 is fed to a mirror image forming circuit 175 constituting an image processing apparatus 180 of this embodiment. The mirror image forming circuit 175 has two video output terminals that are connected to a first monitor 148 and a second monitor 149 respectively. The control circuit 173 checks position information detected by the position sensor 170 and provided by the position detecting means 171 and determines which of two video outputs of the mirror image forming circuit 175 should be selected as a mirror image. The mirror image forming circuit 175, control circuit 173, and position detecting means 171 may be incorporated in the TV camera controller 174 or made stand-alone.

In this embodiment, the endoscope 145 is tilted toward the surgeon A at a point of insertion P at which the endoscope is inserted to the abdominal cavity. In this case, even when the first monitor 148 viewed by the surgeon A visualizes a normal endoscopic image, there is no problem. However, since the surgeon B stands on the opposite side of the surgeon A, when the second monitor 149 viewed by the surgeon B visualizes the normal image, the surgeon B finds it laterally inverse and has difficulty in manipulating forceps. The mirror image forming circuit 175 is therefore used to visualize a mirror image on the second monitor 149 alone. However, when the endoscope 145 is tilted toward the surgeon B, the situation is quite the contrary. A mirror image must be displayed on the first monitor 148 viewed by the surgeon A and a normal image must be displayed on the second monitor 149 viewed by the surgeon B. The position detecting means 171 is therefore designed to detect the tilt of the endoscope 145 all the time. Depending on the tilt, the control circuit 173 selects either of two outputs of the mirror image forming circuit 175 and thus determines which of a normal image and a mirror image should be supplied. In whichever orientation the endoscope 145 is placed, both the surgeons And B can manipulate forceps without any sense of unnaturalness and carry out a surgical procedure smoothly.

Next, the seventeenth embodiment will be described.

The seventeenth embodiment is substantially identical to the sixteenth embodiment. Different components alone will be described. Identical components will be assigned the same reference numerals, of which no mention will be made.

Figure 35:
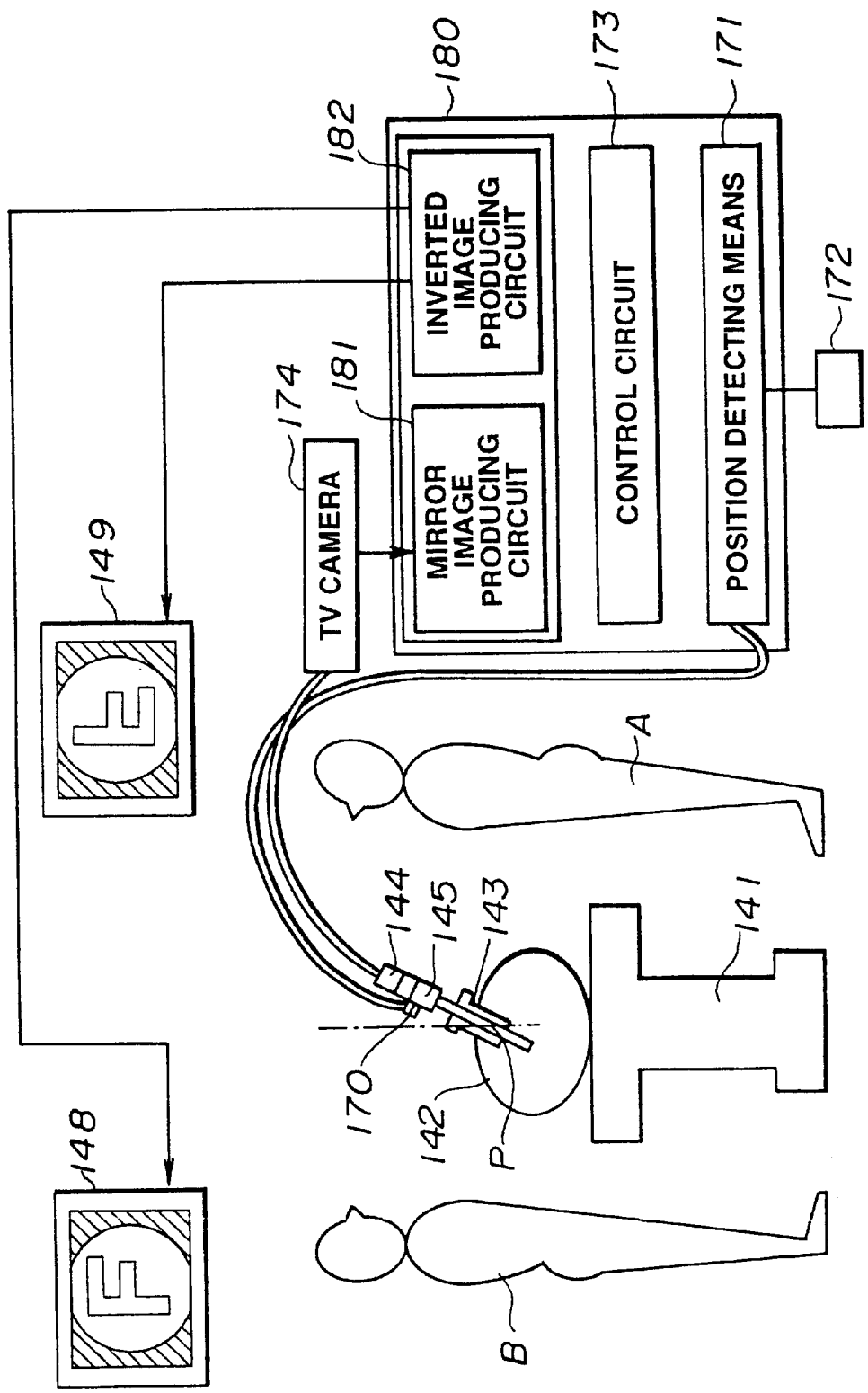
FIGS. 35 and 36 relate to the seventeenth embodiment of the present invention.

As shown in FIG. 35, an image processing apparatus 180 of this embodiment comprises a mirror image producing circuit 181 for producing a mirror image by laterally inverting a raw image provided by an endoscope 145 and an inverted image producing circuit 182 for producing an inverted image by vertically and laterally inverting the raw image provided by the endoscope 145. The other components are identical to those of the sixteenth embodiment.

As described in conjunction with a prior art, it is determined on the basis of a positional relationship between an endoscope and a lesion which of a mirror image or an inverted image is preferred as an image to be seen by a surgeon opposed to the endoscope. The image processing apparatus of this embodiment enables automatic selection of a mirror image or an inverted image.

As shown in FIG. 35, the control circuit 173 determines on the basis of information provided by the position detecting means 171 whether a mirror image or an inverted image should be fed to the monitor 149.

In FIG. 35, the endoscope 145 lies perpendicularly to a lesion. The top of an image seen by the surgeon A corresponds to the bottom of an image seen by the surgeon B. Based on the information provided by the position detecting means 171, the control circuit 173 controls the inverted image producing circuit 182 and supplies an inverted image to the monitor 149.

Figure 36:
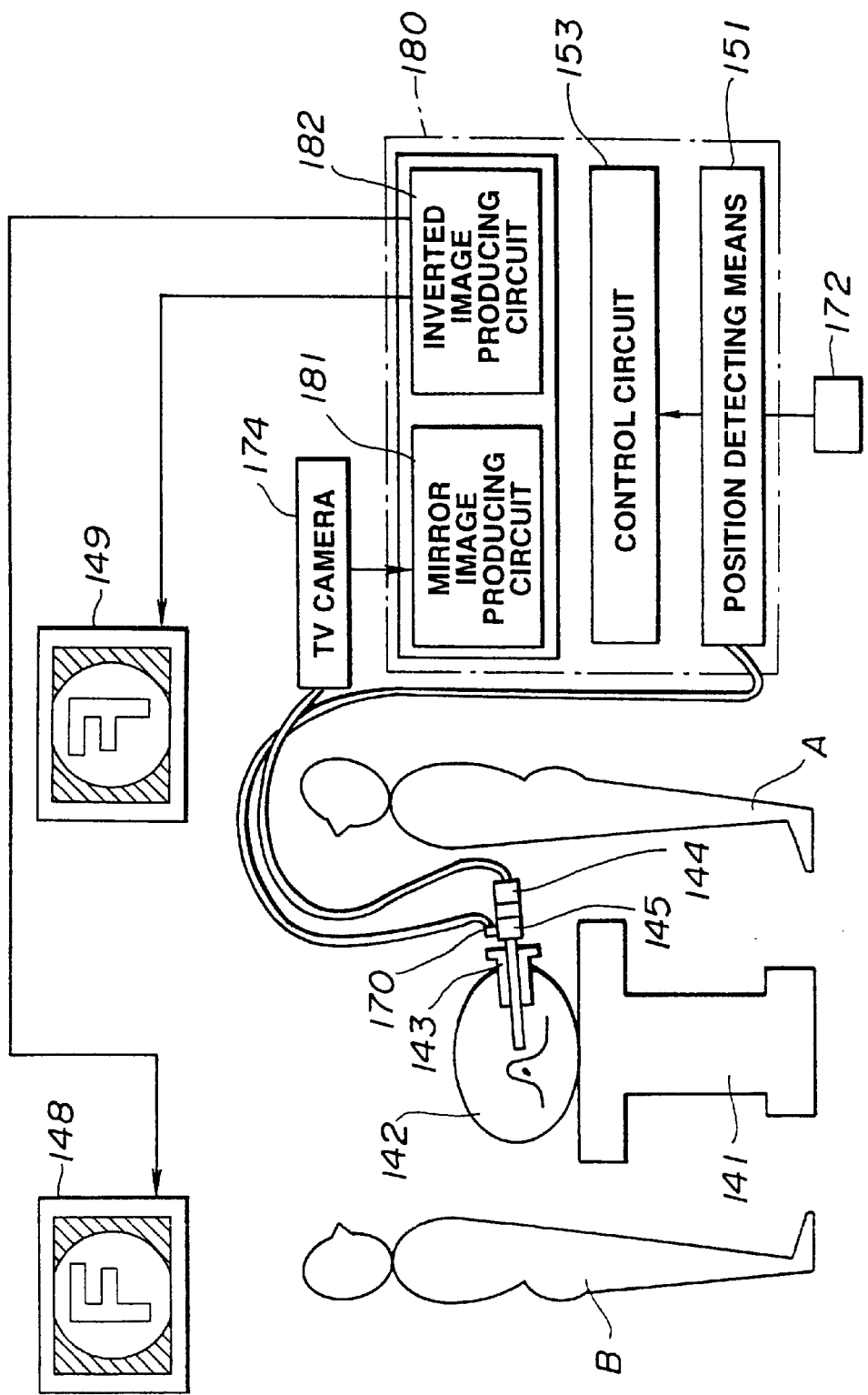

On the contrary, as shown in FIG. 36, when the endoscope 145 is horizontally oriented from the surgeon A toward a lesion, the vertical direction of an image seen by the surgeon A is the same as that of an image seen by the surgeon B. However, the lateral direction of the image seen by the surgeon A is reverse to that of the image seen by the surgeon B. Based on the information provided by the position detecting means 171, the control circuit 173 controls the mirror image producing circuit 181 so as to supply a mirror image to the monitor 149.

The image processing apparatus 180 of this embodiment controls the mirror image producing circuit 181 and inverted image producing circuit 182 according to information supplied from the position detecting means 171. Either a mirror image or an inverted image can therefore be selected automatically. As a result, the surgeons can concentrate on the surgical procedure and manipulate therapeutic appliances without having any sense of unnaturalness.

Next, the eighteenth embodiment will be described.

The eighteenth embodiment is substantially identical to the seventeenth embodiment. Different components alone will be described. Identical components will be assigned the same reference numerals, of which no mention will be made.

Figure 37:
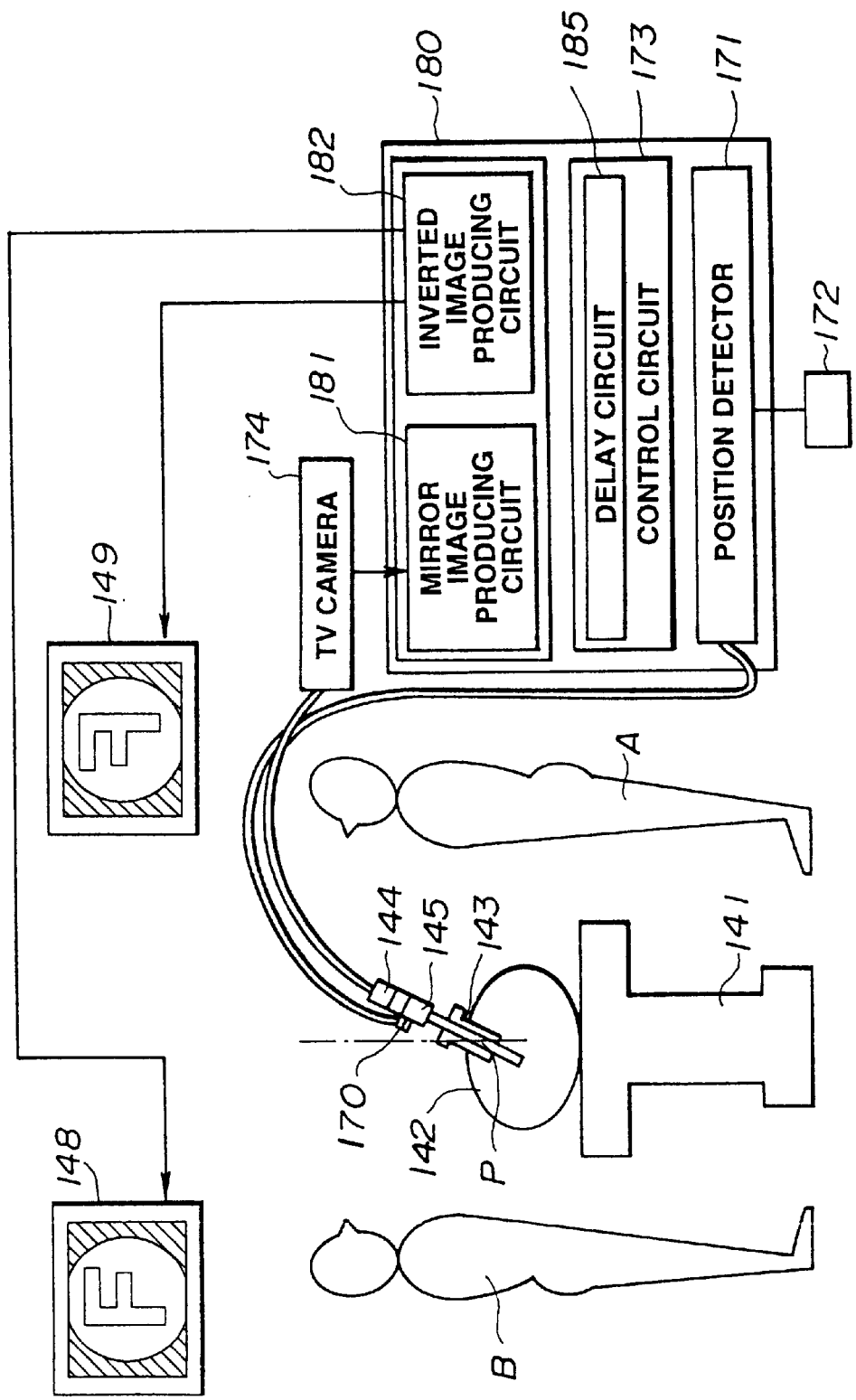

As shown in FIG. 37, this embodiment includes the same components as those of the seventeenth embodiment and has a delay circuit 185 incorporated in a control circuit 173.

When a detected signal (an angle of the endoscope 145 or an amount of reflected light) does not reach a border line, which indicates a predetermined reference angle of the endoscope 145 to be detected by the position detecting means 171 or a predetermined reference amount of reflected light to be detected thereby, for a certain period of time, the delay circuit 185 switches a mirror image to an inverted image or vice versa. The delay circuit helps prevent a mirror image or an inverted from being switched to an inverted image or a mirror image unintentionally frequently at a certain point.

Figure 38:
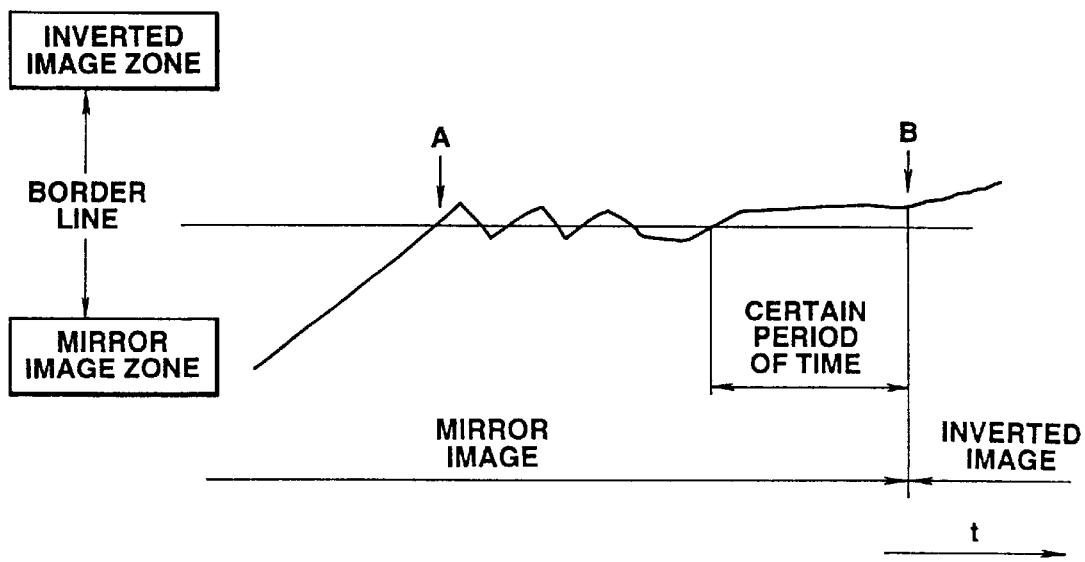

The operation of the delay circuit 185 will be detailed in conjunction with FIG. 38. In FIG. 38, the axis of abscissas represents a time interval and the axis of ordinates represents an angle of the endoscope 145 or an amount of reflected light which is used an index for selecting an inverted image or a mirror image. When the angle of the endoscope 145 is adopted as the index, a border line in FIG. 38 indicates, for example, 30°. FIG. 38 demonstrates that the endoscope 145 is moved from a mirror image zone (the endoscope is placed substantially horizontally) into an inverted image zone (the endoscope is place substantially perpendicularly). In this example, when the endoscope is moved from the mirror image zone to point A in FIG. 38, a mirror image is not changed to an inverted image at point A but is changed to an inverted image at point B after the border line has been overpassed for a certain period of time.

Using the delay circuit 185 in this embodiment, it is prevented that a mirror image or an inverted image is switched to an inverted image or a mirror image unintentionally frequently.

In the above example, it is checked if a change in signal level continues for a certain period of time. Based on the result of check, a mirror image or an inverted image is selected. Alternatively, a hysteresis of a detected signal may be specified in the control circuit 173, thus preventing a mirror image or an inverted image from being switched to an inverted image or a mirror image unintentionally frequently.

Figure 39A:
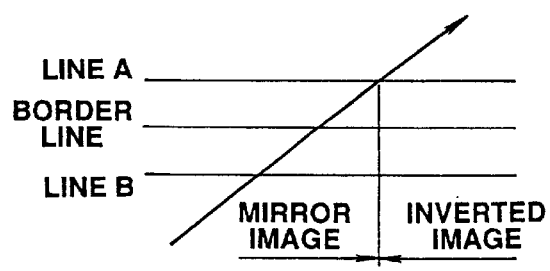
FIG. 39A is the first explanatory diagram concerning the operation of a variant of the delay circuit shown in FIG. 37.
Figure 39B:
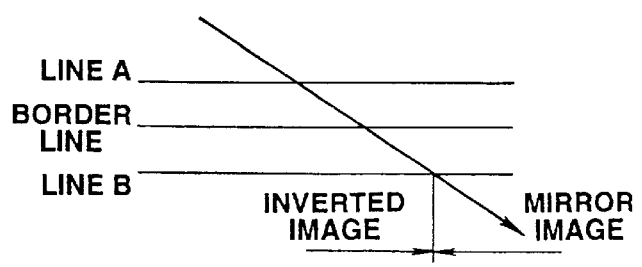

In this case, lines A and B that lie in the inverted image and mirror image zones beyond the border line are specified in the control circuit 173. As shown in FIG. 39A, a change from a mirror image to an inverted image is achieved at a crossing with line A. As shown in FIG. 39B, a change from an inverted image to a mirror image is achieved at a crossing with line B. This can also prevent a mirror image or an inverted image from being switched to an inverted image or a mirror image unintentionally frequently.

Next, the nineteenth embodiment will be described.

The nineteenth embodiment is substantially identical to the seventeenth embodiment. Different components alone will be described. Identical components will be assigned the same reference numerals, of which no mention will be made.

Figure 40:
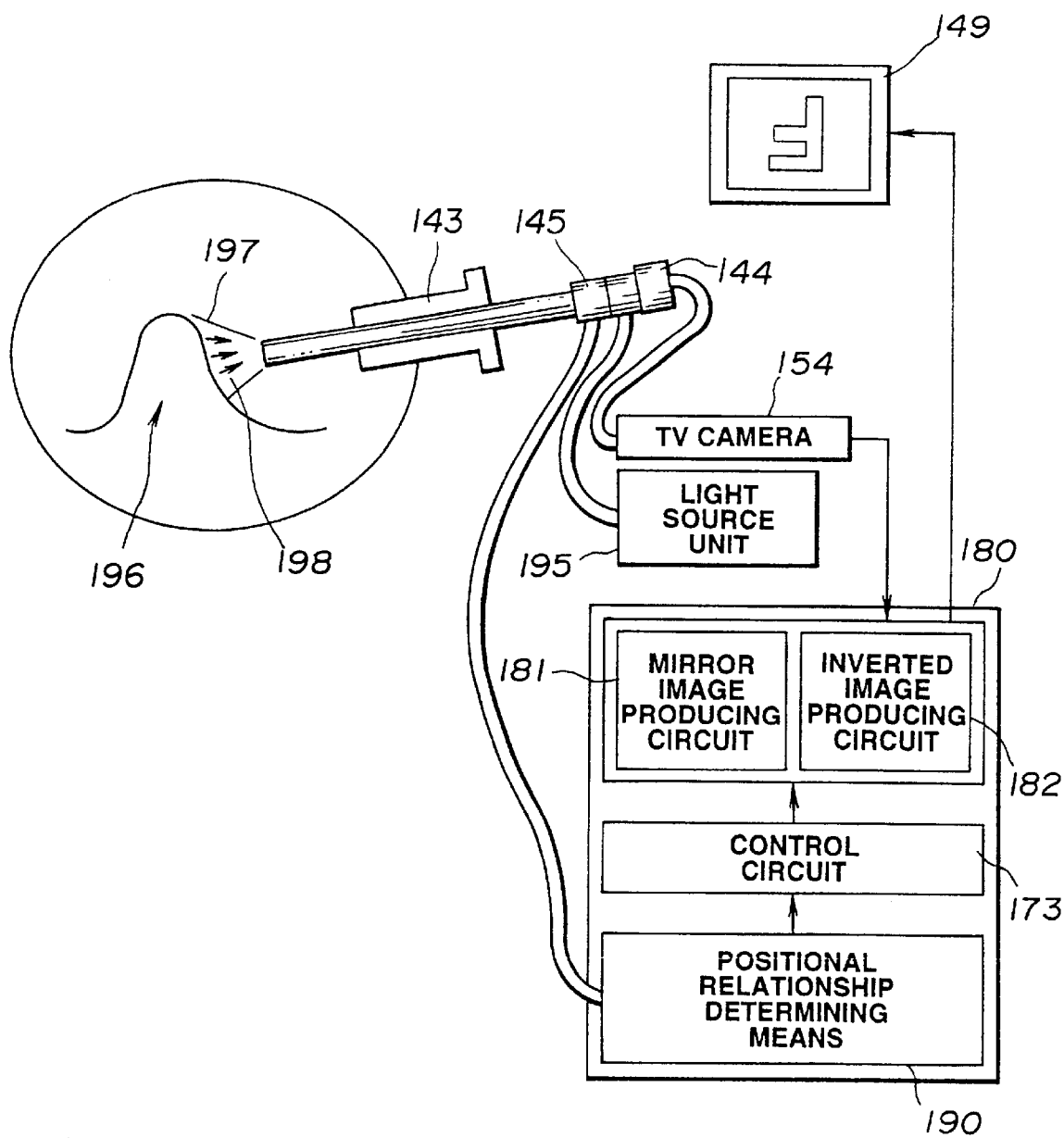
FIGS. 40 and 41 relate to the nineteenth embodiment of the present invention.

As shown in FIG. 40, the nineteenth embodiment includes a positional relationship determining means 190 instead of the position sensor 170, position detecting means 171, and receiver 173 included in the seventeenth embodiment.

Figure 41:
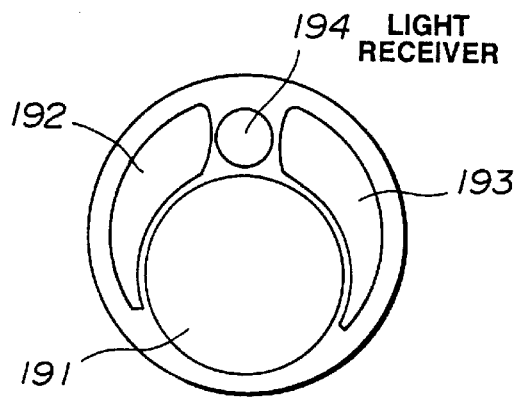

The distal part of the endoscope 145 is, as shown in FIG. 41, composed of an objective lens 191 for receiving a view of a lesion, illuminators 192 and 193 for irradiating illumination light to a lesion (region of view), and a light receiver 194 for receiving returned light of illumination light irradiated by the illuminators 192 and 193 and outputting an amount of light to the determining means 190.

In this embodiment, as shown in FIG. 40, light supplied from the light source unit 195 is transmitted to the illuminators 192 and 193 via light guides that are not shown, and irradiated as illumination light 197 to the lesion 196 (region of view) by the illuminators 192 and 193. Light 198 reflected from the lesion 196 is transmitted to the endoscope 145 via the objective lens 191. A view is thus transmitted to an eyepiece unit and picked up by the TV camera head 144. On the other hand, the reflected light 198 also enters the light receiver 194. The amount of the reflected light 198 is thus detected. The detected information of the amount of light is output to the positional relationship determining means 190.

Based on the information of the amount of light detected by the light receiver 194, the positional relationship determining means 190 determines whether the lesion 196 is swelling perpendicularly to the endoscope 145. Depending on the result of determination, the positional relationship determining means 190 controls the control circuit 173 so as to determine whether a mirror image be supplied to the monitor 149. The positional relationship determining means 190 determines a positional relationship between a lesion and an endoscope by comparing an amount of reflected light with a predetermined value. For example, if the amount of reflected light 198 is larger than the predetermined value, it is determined that the lesion 196 is, as shown in FIG. 40, swelling perpendicularly to the endoscope 145.

This embodiment employs the illumination light 197 supplied from the light source unit 195. Alternatively, a laser or any other light emitter may be mounted in the distal part of the endoscope 145. Returned light may then be measured. In this case, the adoption of a laser will enable high-precision recognition of a positional relationship.

When the position detecting means 171 in the seventeenth embodiment is used in combination with the positional relationship determining means 190 in this embodiment, a mirror image can be switched to an inverted image or vice versa with higher precision.

Needless to say, the eighteenth embodiment can be implemented in this embodiment with ease.

Next, the twentieth embodiment will be described.

Figure 42:
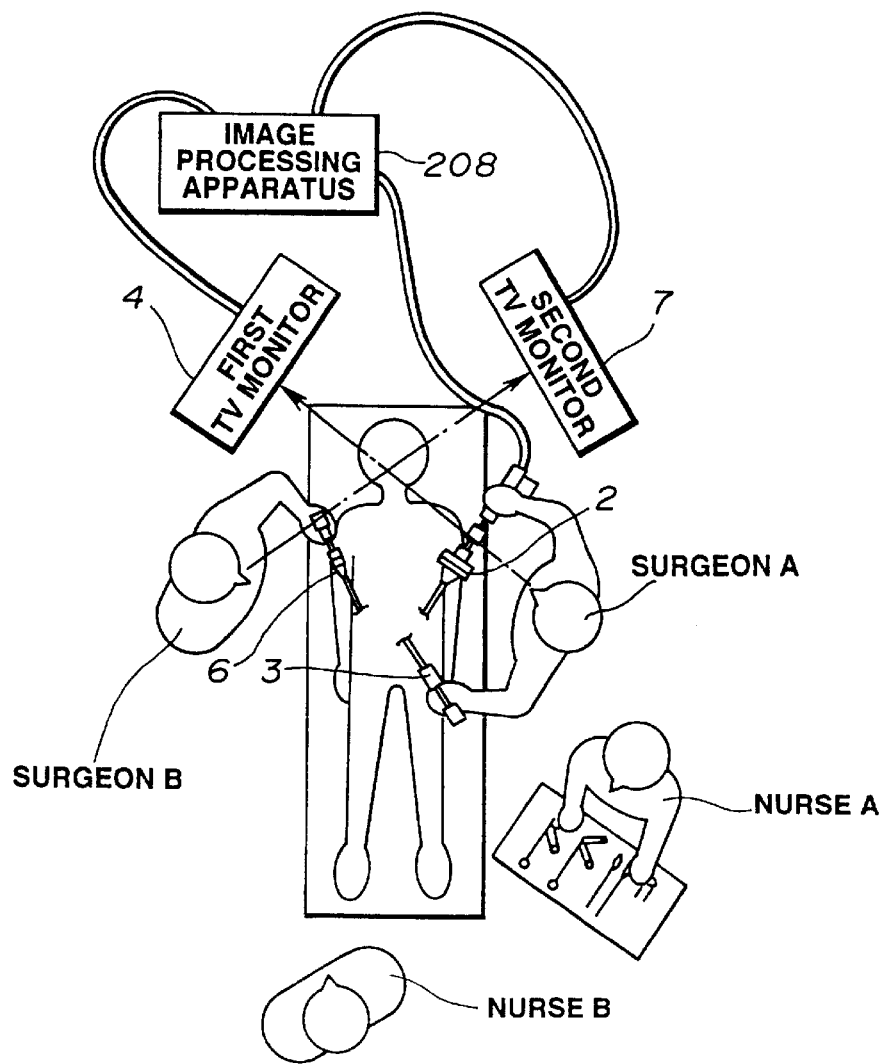
FIGS. 42 to 46 relate to the twentieth embodiment of the present invention.

FIG. 42 shows an operation room, in which a surgical procedure is in progress under endoscopic observation, from above. Surgeons A and B have inserted therapeutic appliances and a rigid endoscope into a body cavity using trocars and cannulas having pierced the wall of the body cavity. The surgeon A holds an endoscope 2 with a TV camera (which will be referred to as an endoscope 2 for brevity's sake) and a therapeutic appliance 3 and proceeds with the surgical procedure while viewing a first monitor 4. The surgeon B holds a therapeutic appliance 6 and proceeds with the surgical procedure while viewing a second monitor 7.

A video signal sent from the TV camera of the endoscope 2 is fed to and processed by an image processing apparatus 208, and then displayed on each of the first and second monitors 4 and 7. As described previously, the first monitor 4 is viewed mainly by the surgeon A, while the second monitor 7 is viewed mainly by the surgeon B.

The present invention may apply to a system configuration in which an electronic endoscope having a solid-state imaging device at the tip of an insertional part thereof is included in place of an endoscope with a TV camera. Moreover, the first and second monitors 4 and 7 may be replaced with image VTRs, optical disk drives, or any other recording means.

Figure 43:
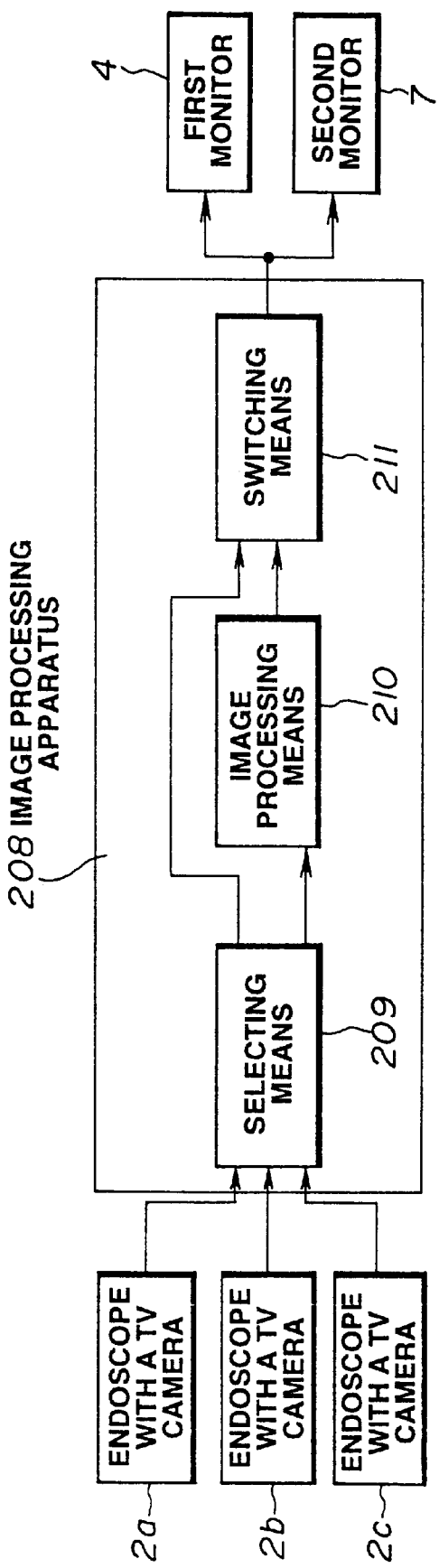

FIG. 43 is a block diagram showing an endoscope system that includes a plurality of endoscopes 2 shown in FIG. 42. The endoscope system shown in FIG. 43 comprises a plurality of (three in this example) endoscopes 2 (2a, 2b, and 2c), the first monitor 4 and the second monitor 7, and the image processing apparatus 208 for visualizing video signals sent from the endoscopes on the first monitor 4 and second monitor 7.

As shown in FIG. 43, the image processing apparatus 208 includes a selecting means 209 for selecting any of video signals sent from the endoscopes 2a, 2b, and 2c, an image processing means 210 for image-wise processing a video signal selected by the selecting means 209, and a switching means 211 for selectively supplying a video signal sent from an endoscope and selected by the selecting means 209 and an output of the image processing means 210 to each of the first and second monitors 4 and 7.

For helping surgeons carry out a surgical procedure smoothly, the image processing apparatus 208 selectively supplies a vertically and laterally inverted image (inverted image) and a raw image, which are represented by a video signal selected from among a plurality of video signals, to each of the monitors.

Figure 44:
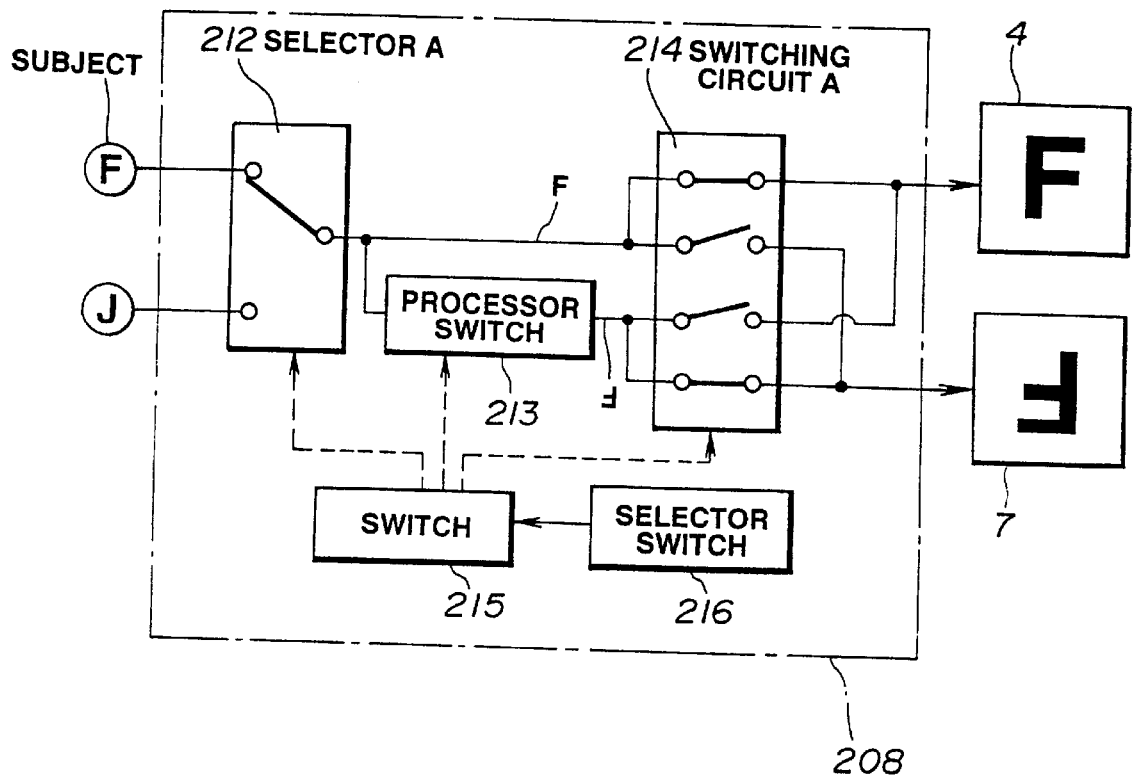
Figure 45:
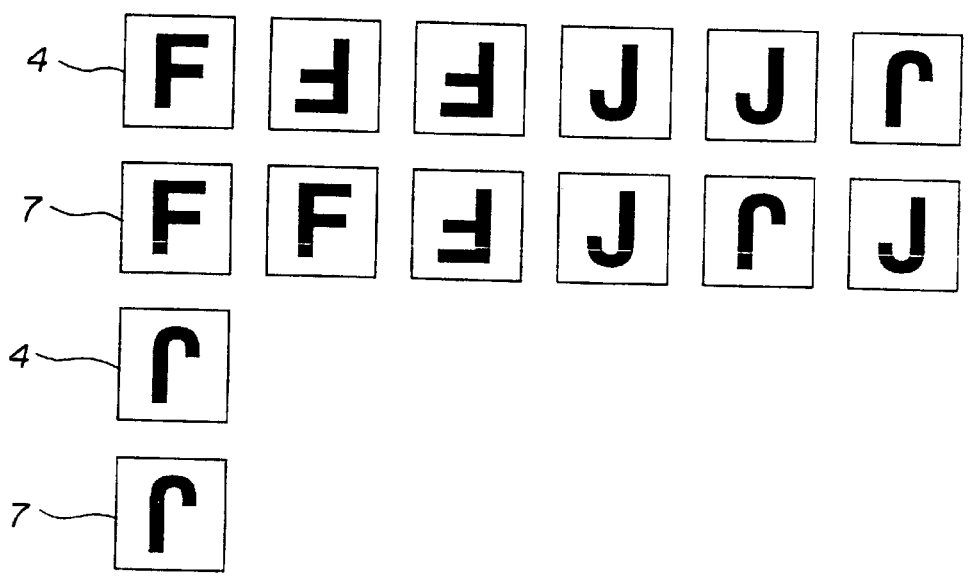

FIG. 44 shows an example of circuitry of the image processing apparatus 208. FIG. 45 shows a variety of combinations of displays on the first and second monitors.

The image processing apparatus 208 shown in FIG. 44 includes a selector A 212 serving as a selecting means for selecting a video signal representing a subject and originating from the endoscope 2, a processor 213 serving as an image processing means for performing given image processing on a selected video signal, a switching circuit A 214 serving as a switching means for switching signals to be supplied to the monitors 4 and 7, a switch 215 for controlling the selector A 212, processor 213, and switching circuit A 214, and a selector switch 216 for outputting a switching instruction to the switch 215. The switching circuit A 214 selectively supplies either of a video output (raw signal) of the endoscope 2 or an output of the processor 213 to each of the first monitor 4 and second monitor 7, and selectively displays images shown in FIG. 45 on the first and second monitors 4 and 7. "F" and "J" in FIG. 45 are schematic representations of a subject imaged by the endoscope 2. The configuration shown in FIG. 44 applies to a system configuration including two endoscopes.

Figure 46:
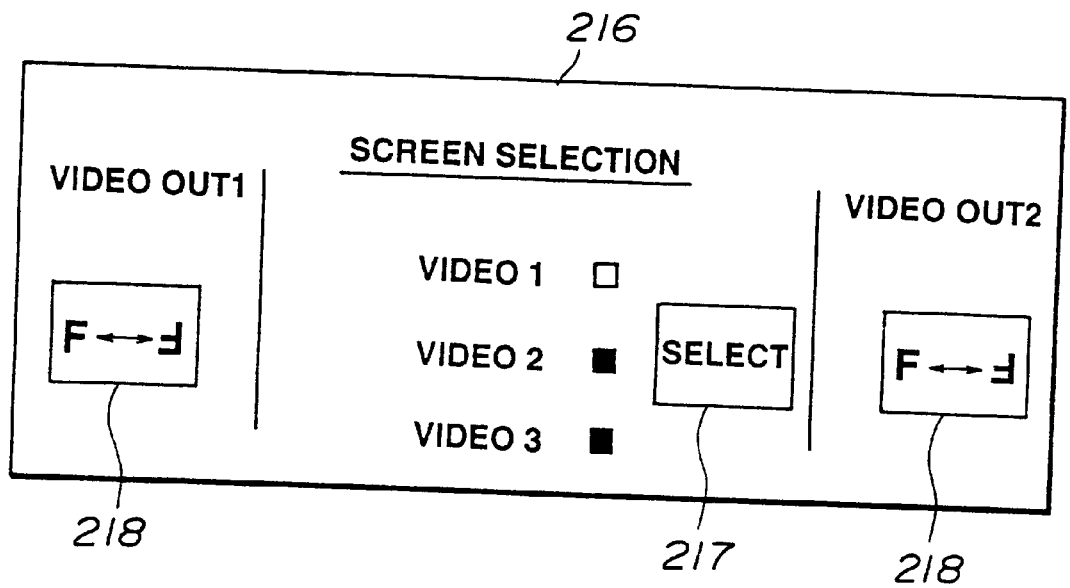

FIG. 46 is an enlarged view of the surface of the selector switch 216. The selector switch 216 includes a Select switch 217 for use in selecting a video signal and two inverted image switches 218 for use in inverting an image. Videos 1 to 3 correspond to video signals sent from the endoscopes 2a to 2c any of which is selected by the selector switch 216. A white square in FIG. 46 means that a lamp lights and the associated video signal is selected by the selector A 212 and displayed. A black square in FIG. 46 means that a lamp is put out. Videos 2 and 3 are not selected. Video Out 1 and Video Out 2 correspond to outputs to be supplied to the monitors 4 and 7 respectively.

The operation of the image processing apparatus will be described with reference to the drawings.

In FIG. 42, the surgeon A carries out a surgical procedure while viewing the first monitor 4, and the surgeon B carries out the surgical procedure while viewing the second monitor 7. The surgeon B is opposed to the endoscope 2. Therefore, when a raw image provided by the endoscope 2 is displayed on the second monitor 7 as it is, the surgeon B finds it vertically and laterally inverse. The image processing apparatus 208 is therefore used to visualize an inverted image by vertically and laterally inverting an image to be displayed on the second monitor 7. Entries made at the selector switch 216 for the above operation as well as the operation of the image processing apparatus 208 will be described below.

For displaying a raw image of a subject F on the first monitor 4 as shown in FIG. 44, the Select switch 217 in the selector switch 216 is used to select any of Videos 1 to 3 representing an F image. The selector switch 216 then transmits a selection instruction signal to the switch 215. In response to the selection instruction signal sent from the switch 215, the selector A 212 selects the video signal representing the F image. The switching circuit A 214 is then switched over to the first monitor 4 so that the video signal is supplied to the first monitor 4.

For displaying an inverted image of F on the second monitor 7, similarly to the above case, a video signal representing F and being selected by the selector 212 is supplied as a processed video signal representing an inverted image by means of the processor 213. Therefore, the inverted image switch 218 in Video Out 2 in the selector switch 216 is pressed. With the instruction entered by pressing the switch, a control signal is sent from the switch 215 to the switching circuit A 214. The switching circuit A 214 is switched over to the second monitor 7 so that the video signal processed by the processor 213 is supplied to the second monitor 7. Alternatively, the switches in the selector switch 216 may be used to display an inverted image of F on the first monitor 4 and a raw image of F on the second monitor 7. The above operation is still effected even when any of Videos 1 to 3 is selected in order to visualize a subject J.

In this embodiment, an inverted image is displayed on the second monitor 7. The surgeon B will therefore not have proceeds a vertically and laterally inverted view during a surgical procedure, and can therefore proceed with the procedure smoothly. An inverted image can be displayed on either of the first monitor 4 and second monitor 7. A change in orientation of the endoscope 2 or a change in position of a surgeon can be dealt with readily.

Next, the twenty-first embodiment will be described.

An image processing apparatus of this embodiment is substantially identical to that of the twentieth embodiment. An outstanding difference from the twentieth embodiment lies in a means for processing a video signal so that an image represented by the video signal is turned by any angle. The other components and modes of operation shown in FIGS. 42 to 44 are substantially identical to those of the twentieth embodiment. The difference alone will be described below.

Figure 47:
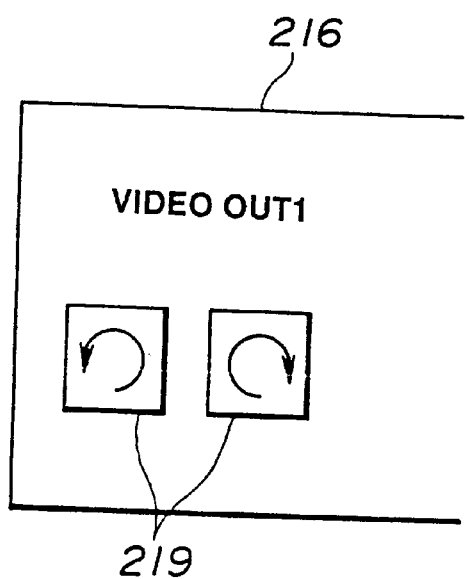
FIG. 47 is an enlarged view of a selector switch relating to the twenty-first embodiment of the present invention.

In the image processing apparatus of this embodiment, as shown in FIG. 47, two turn switches 219 are added to each of the two inverted image switches 218 of Video Out 1 and Video Out 2 in the selector switch 216 in the twentieth embodiment. FIG. 47 shows only one of the turn switches. As shown in FIG. 47, the turn switch 219 instructs a turn of an image to the left or right. Under the control of the switch 215, the processor 213 turns an image provided by the endoscope 2 in response to the turn instruction.

In the foregoing configuration, when the endoscope 2 turns in FIG. 42, the F image on each of the first monitor 4 and second monitor 7 tilts and becomes hard for the surgeons to see. In particular, when an endoscope giving an oblique view is employed, the endoscope may be turned. Therefore, when an image on a monitor is inclined from the upright position, it hinders smooth proceeding of a surgical procedure. In this case, any of the turn switches 219 in the selector switch 216 is pressed in order to send a control signal instructing a turn of a video signal from the switch 215 to the processor 213. For example, when either of the turn switches 219 of Video Out 1 is pressed, the control signal causes the processor 213 to turn an image by a given quantity or for a period of time during which the switch is on. The turned image is then supplied to the first monitor 4 via the switching circuit A 214. Thus, a tilt of an endoscopic image is corrected by turning the endoscopic image by any angle.

In this embodiment, when the endoscope 2 such as an endoscope giving an oblique view is turned, an image to be displayed on a monitor is turned. Thus, a surgeon can orient an endoscopic image correctly and carry out a surgical procedure smoothly.

Next, the twenty-second embodiment will be described.

An image processing apparatus of the twenty-second embodiment synthesizes two or more video signals selected from among a plurality of input video signals, produces an inverted image from at least one of the selected video signals, and selectively displays a synthetic image or an inverted image, which is a processed image, and a raw image.

Components of this embodiment identical to those of the twentieth embodiment will be assigned the same reference numerals. No mention will be made of the components as well as the modes of operation identical to those of the twentieth embodiment.

Figure 48:
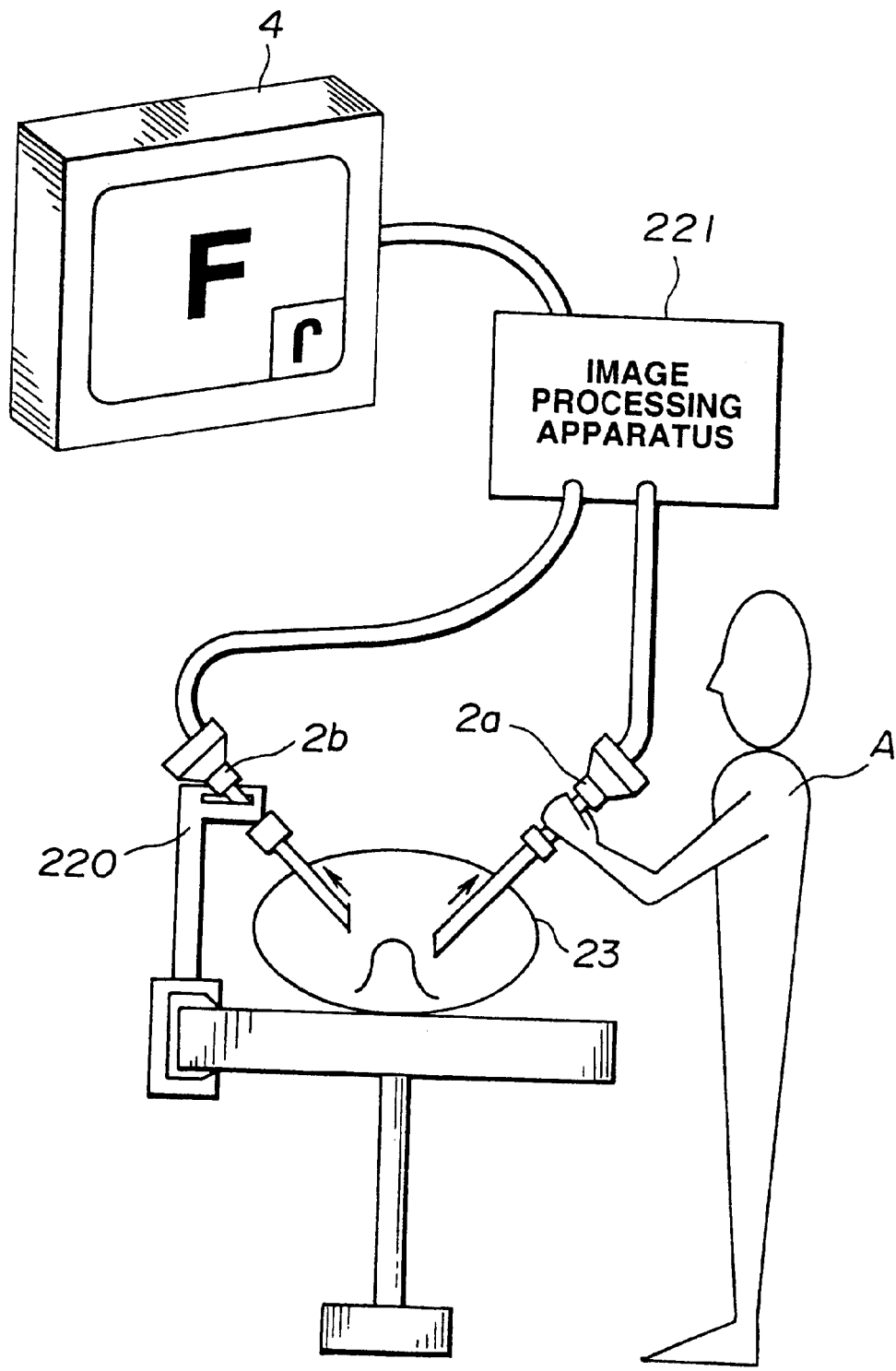

FIG. 48 shows the twenty-second embodiment.

An endoscope 2a is held by a surgeon A, while an endoscope 2b opposed to the surgeon A is supported by an endoscope support 220. Images provided by the endoscope 2a and endoscope 2b are sent to an image processing apparatus 221. The image processing apparatus 221 transmits an image, which has been subjected to given processing or selected according to an instruction issued by a selector switch that will be described later, to the first monitor 4. Reference numeral 223 denotes a subject.

Figure 49:
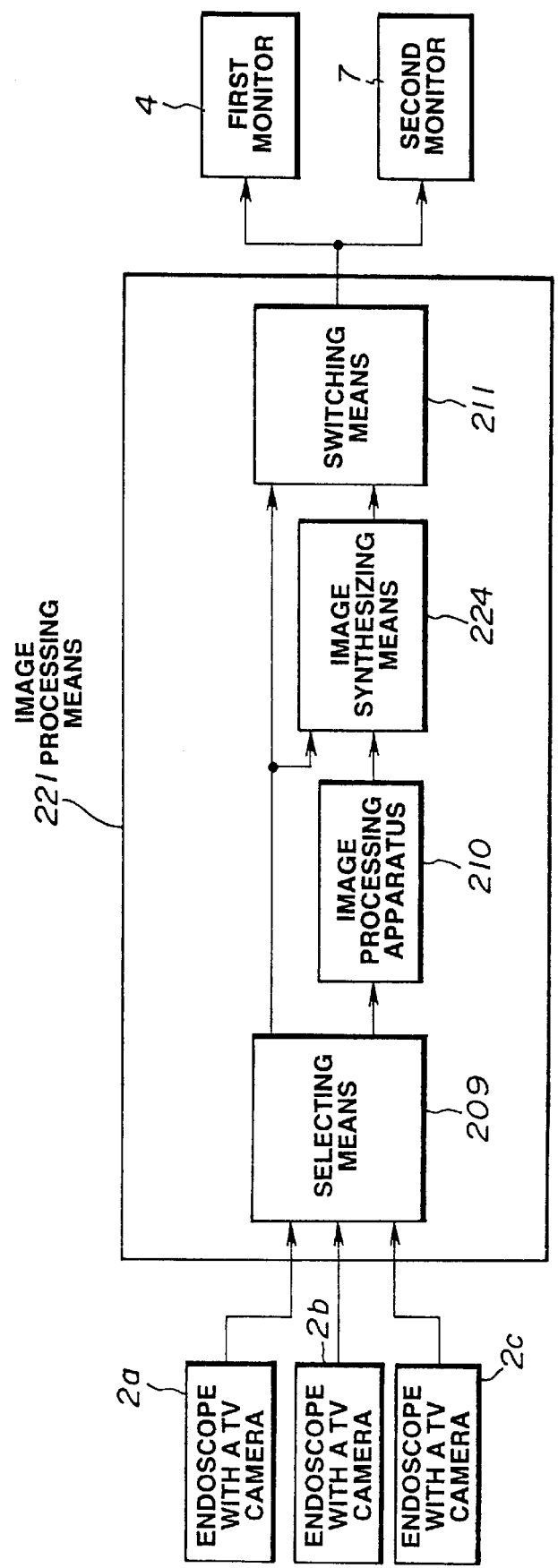

FIG. 49 is a block diagram showing the twenty-second embodiment.

The image processing apparatus 221 of this embodiment has substantially the same components as those of the twentieth embodiment shown in FIG. 43. A difference from the twentieth embodiment lies in that an image synthesizing means 224 is interposed between an image processing means 210 and a switching means 211. The image synthesizing means 224 synthesizes an output of a selecting means 209 with an output of the image processing means 210, and supplies a synthetic signal to the switching means 211.

Figure 50A:
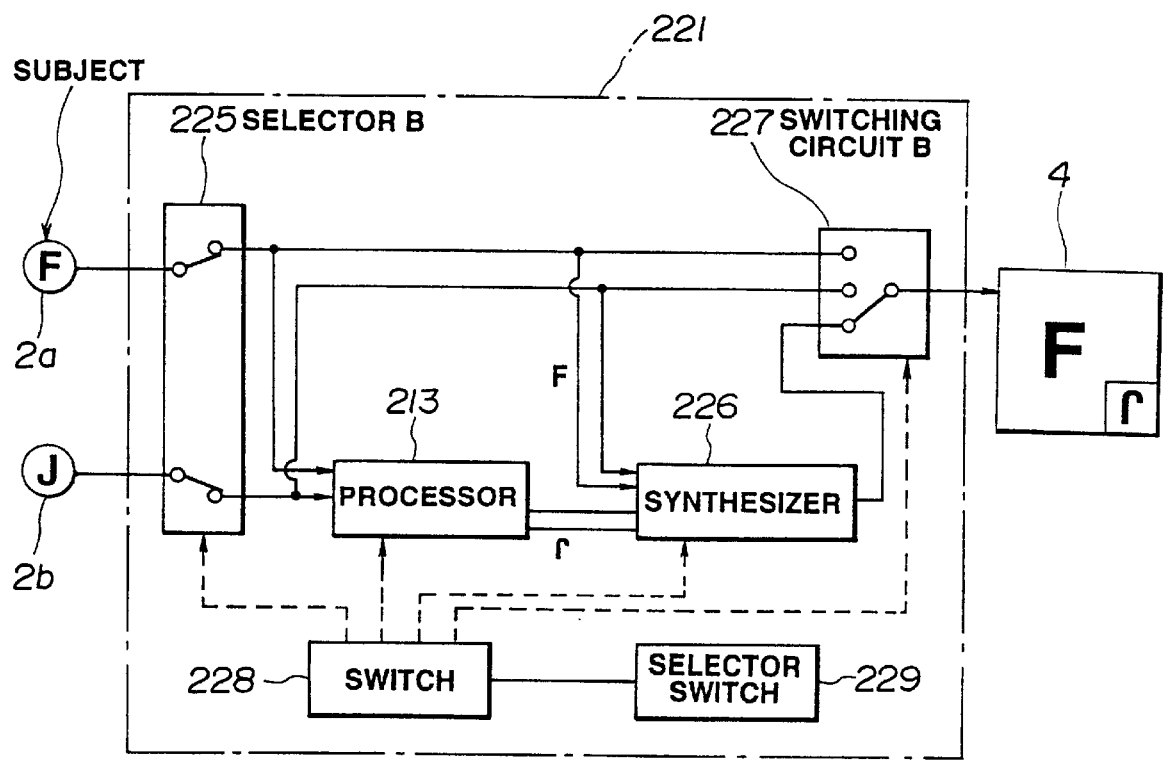
FIG. 50A is a circuit diagram showing the circuitry of the image processing apparatus.
Figure 50B:
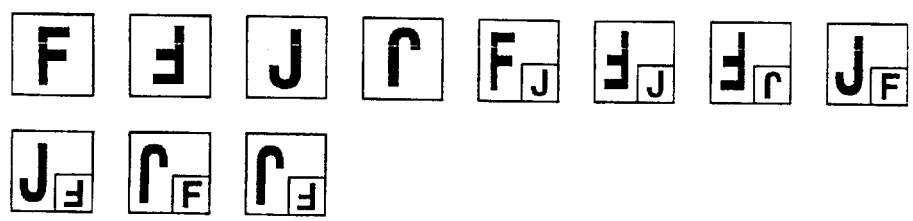
FIG. 50B shows an example of a display on a monitor in the image processing apparatus shown in FIG. 50A.

FIG. 50A shows an example of circuitry of the image processing apparatus 221. FIG. 50B shows a variety of displays.

As shown in FIG. 50A, the image processing apparatus 221 comprises a selector B 225 for selecting an input video signal, a processor 213 for processing a video signal sent from the selector B 225, a synthesizer 226 for synthesizing a plurality of video signals, a switching circuit B 227 for switching video signals to be supplied to the monitor 4, and a switch 228 and a selector switch 229 which control the selector B 225, processor 213, synthesizer 226, and switching circuit B 227.

Figure 51:
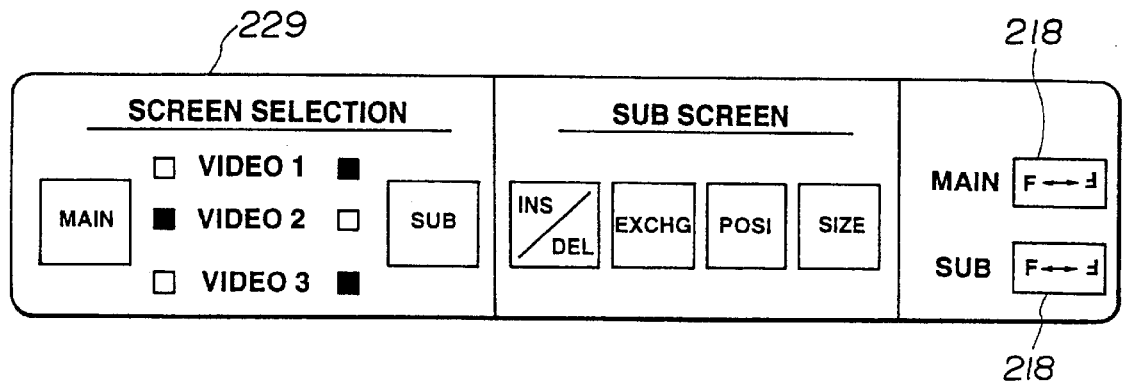

FIG. 51 is an enlarged view showing the selector switch 229 including the inverted image switches 218. The selector switch 229 includes a Screen Selection block for selecting video signals to be synthesized image-wise from among a plurality of video signals. The Screen Selection block includes a main selection switch (hereinafter, a Main switch) for selecting a main image for a synthetic image and a sub selection switch (hereinafter, a Sub switch) for selecting a sub image for the synthetic image. Every time the Main switch is pressed, any of Videos 1 to 3 corresponding to input video signals; that is, any of outputs of endoscopes 2a to 2c each having a TV camera is selected. A currently selected input signal is indicated with a lighting lamp adjacent to any of Videos 1 to 3. The same applies to the Sub switch.

A Sub Screen block of the selector switch 229 selects any of various functions involving a sub image. For example, an Ins/Del switch is used to select whether a main image should be synthesized with a sub image. "Ins" means that images are synthesized.

The system configuration of FIG. 48 includes two endoscopes and one monitor. Description proceeds using this configuration as an example.

Referring to FIGS. 48, 50A, 50B, and 51, the operations of components in this embodiment will be described.

An image of a subject F provided by the endoscope 2a and an image of a subject J provided by the endoscope 2b, which are shown in FIG. 48, are processed by the image processing apparatus 221 according to an entry made at the selector switch 229. A synthetic image is then displayed on the first monitor 4. Synthetic display enables the surgeon A to observe the F and J images merely by viewing the first monitor 4 and eventually to carry out a surgical procedure. However, since the surgeon A is opposed to the endoscope 2b, when a raw image provided by the endoscope 2b is displayed as it is, the surgeon A finds the image vertically and laterally inverse. With a given entry made at the selector switch 229, the image processing apparatus 221 visualizes an inverted image, which is made by vertically and laterally inverting the J image provided by the endoscope 2b, on the first monitor 4. That is to say, the image shown in FIG. 50A appears on the monitor 4.

Referring to FIGS. 50A, 50B, and 51, the operation of the image processing apparatus 221 for visualizing a synthetic image on the first monitor 4 will be described below.

When a video signal representing a subject F is selected by pressing any of Videos 1 to 3 using the Main switch in the selector switch 229, the selector B 225 selects the F image. For synthesizing the F image with a J image, first, the J image is designated using the Sub switch in the selector switch 229. The Ins/Del switch is then pressed, whereby the synthesizer 226 synthesizes a video signal representing the F image with a video signal representing the J image. At this time, the F image is displayed as a main image, and the J image is displayed as a sub image. For producing an inverted image of the J image serving as a sub image similarly to the one on the first monitor 4, the Sub inverted image switch 218 is pressed. With an instruction entered by pressing the switch, a processed video signal representing an inverted J image is fed from the processor 213 to the synthesizer 226. The inverted J image can then be synthesized with the F image as mentioned above. Thus, the circuitry shown in FIG. 50A can display an inverted image of the F image, a raw image of the J image, or any of a variety of combined images on the first monitor 4 according to an instruction entered at the selector switch 229. Examples of displays are shown in FIG. 50B. Depending on an entry made at the selector switch 229 and instructions concerning inversion issued from the Main and Sub switches, erect images or inverted images of the F and J images can be displayed independently, or the erect image or inverted image of the F or J image and the erect image or inverted image of the J or F image can be displayed as a main image and a sub image.

Next, other switches in the selector switch 229 will be described. When an Exchg switch is pressed, the synthesizer 226 synthesizes video signals representing main and sub images in reverse. This means that the main and sub images are exchanged for each other. When a Posi switch is pressed, the display position of a sub image changes. When a Size switch is pressed, the size of a sub image changes. These processing is executed by the synthesizer 226.

In this embodiment, two endoscopic images can be displayed on the first monitor 4. By changing entries to be made at the selector switch 229, display forms can be changed. The surgeon A will not have a vertically and laterally inverse view during a surgical procedure. Even when the position of the surgeon A or first monitor 4 changes, a desired image can be displayed on a monitor by making an entry at the selector switch 229.

Next, the twenty-third embodiment will be described.

An image processing apparatus of this embodiment is substantially identical to the one of the twenty-second embodiment. A particular difference from the twenty-second embodiment lies in a configuration in which a processed image such as a synthetic image or an inverted image, or a raw image can be selected independently for each display means. Components identical to those of the twentieth or twenty-second embodiment will be assigned the same reference numerals. No mention will be made of the components as well as the mode of operation identical to that of the twentieth or twenty-second embodiment.

Figure 52:
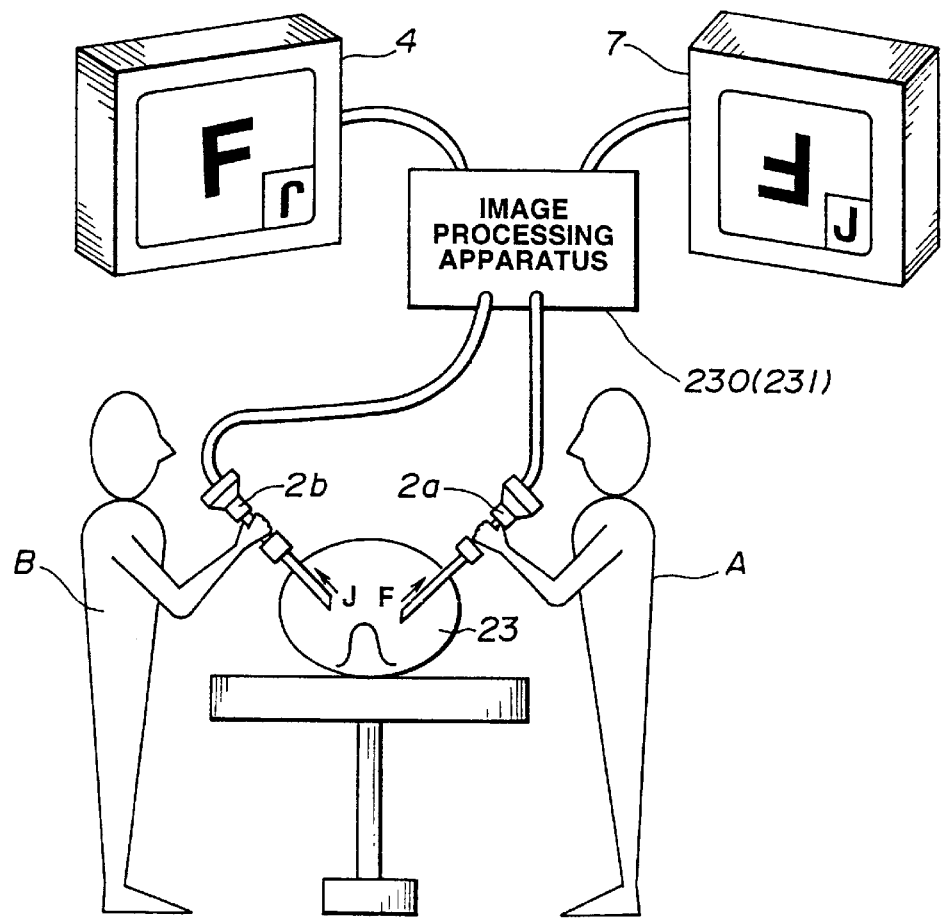
FIGS. 52 to 54 relate to the twenty-third embodiment of the present invention.

FIG. 52 briefly shows the twenty-third embodiment.

Differences of the twenty-third embodiment from the twenty-second embodiment shown in FIG. 48 are that the endoscope 2b is held by the surgeon B but not by the endoscope support 220 and that a second monitor 7 is included.

Figure 53:
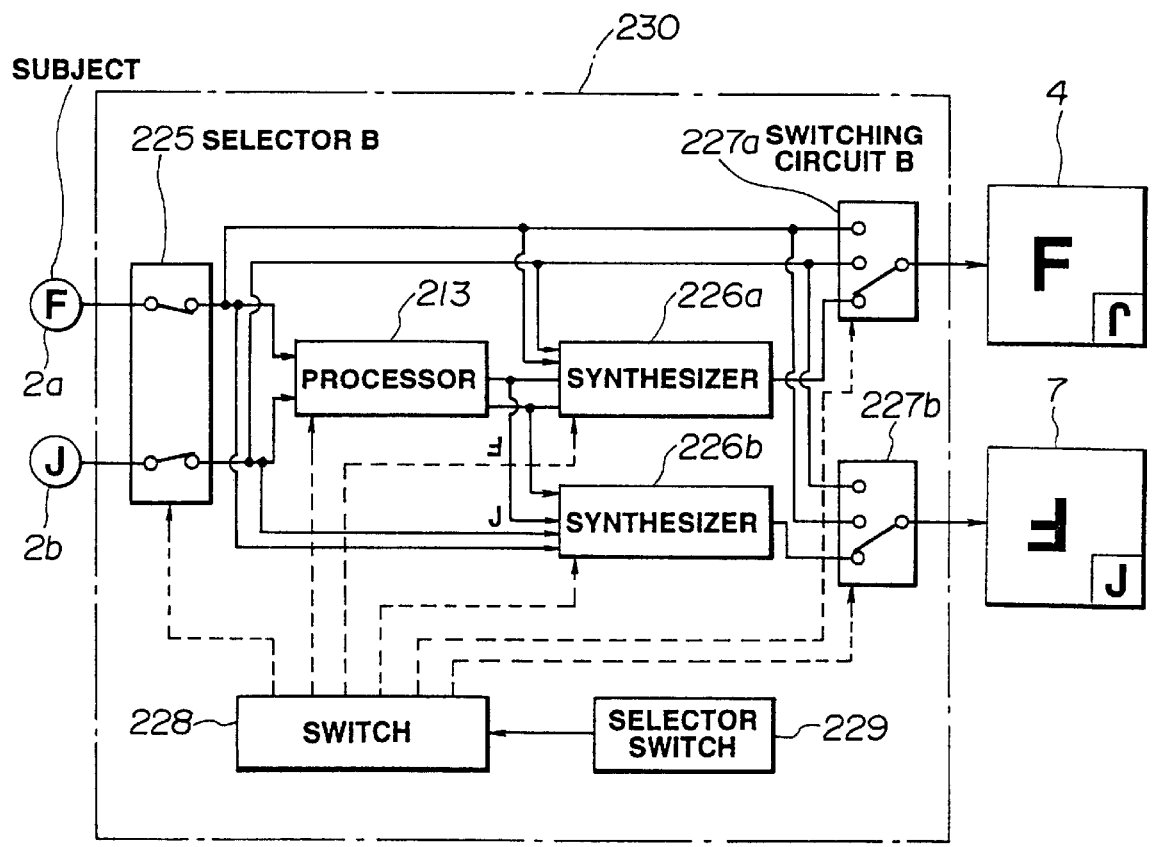
Figure 54:
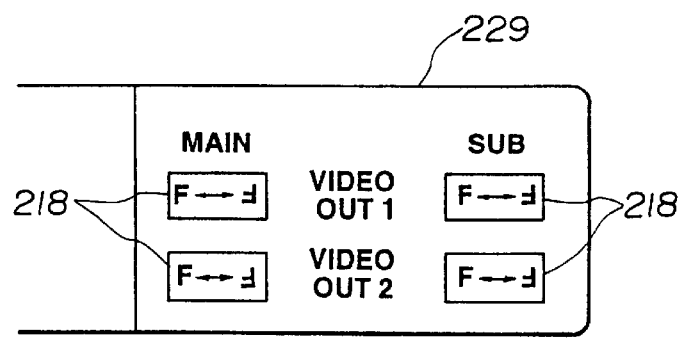

FIG. 53 shows an example of circuitry of an image processing apparatus 230 shown in FIG. 52. Differences from the twenty-second embodiment are that pluralities of synthesizers 226 and switching circuits B 227 are included for the system configuration of FIG. 53 and that inverted image switches 218 are installed, as shown in FIG. 54, for each video output in the selector switch 229.

The image processing apparatus 230 shown in FIG. 53 includes synthesizers 226a and 226b each synthesizing an output of the processor 213 with an output of the selector B 225 according to an instruction sent from the switch 228, a switching circuit B 227a for selectively supplying an output of the selector B 225 and a synthetic output of the synthesizer 226a, and a switching circuit B 227b for selectively supplying an output of the selector B 225 and a synthetic output of the synthesizer 226b.

In the aforesaid system configuration, as shown in FIG. 52, an image of a subject F provided by the endoscope 2a and an image of a subject J provided by the endoscope 2b are processed by the image processing apparatus 230. A synthetic image is displayed on each of the first monitor 4 and the second monitor 7. When the same image as the one appearing on the first display 4 is displayed on the second display 7, the surgeon B finds it vertically and laterally inverse. The image processing apparatus 230 is therefore designed to, as shown in FIG. 53, produce an inverted image using the video signals representing the F and J images appearing on the first monitor 4 and then display the inverted image on the second monitor 7.

Next, the operation of the image processing apparatus 230 will be described specifically. As shown in FIG. 53, a synthetic image is displayed on the first monitor 4 in the same manner as that in the twenty-second embodiment. For displaying an image on the second monitor 7, the Main and Sub inverted image switches 218 of Video Out 2 in the selector switch 229 shown in FIG. 54 are pressed. The image processing apparatus 230 then allows the synthesizer 226b to synthesize an inverted F image made by vertically and laterally inverting an F image on the first monitor 4 and a raw J image, and causes the switching circuit B 227b to display the synthetic image on the second monitor 7. Thus, when synthetic images are displayed on the first monitor 4 and second monitor 7 respectively, the selector B 225, processor 213, synthesizer 226a, synthesizer 226b, switching circuit B 227a, and switching circuit B 227b are controlled by making entries at the selector switch 229. In the circuitry of the image processing apparatus 230 shown in FIG. 53, any of a variety of combinations of the F and J images can be displayed on the first monitor 4 and second monitor 7 merely by making entries at the selector switch 229. Any of the images shown in FIG. 50B can be displayed.

Owing to the embodiment, the surgeons A and B will not have a vertically and laterally inverse view during a surgical procedure. Furthermore, video signals can be processed independently for each of monitors. Even if the number of surgeons or monitors changes, cable connections need not be modified.

Next, the twenty-fourth embodiment will be described.

An image processing apparatus of the twenty-fourth embodiment is substantially identical to the one of the twenty-third embodiment. However, the image processing apparatus of the twenty-fourth embodiment includes a third switching means for selectively supplying the same image as a first display image that is different from the display image of the first monitor 4 and an inverted image of the first display image. Components identical to those of the twenty-third embodiment will be assigned the same reference numerals. No mention will be made of the components as well as the modes of operation identical to those of the twenty-third embodiment. The difference alone will be described.

Figure 55:
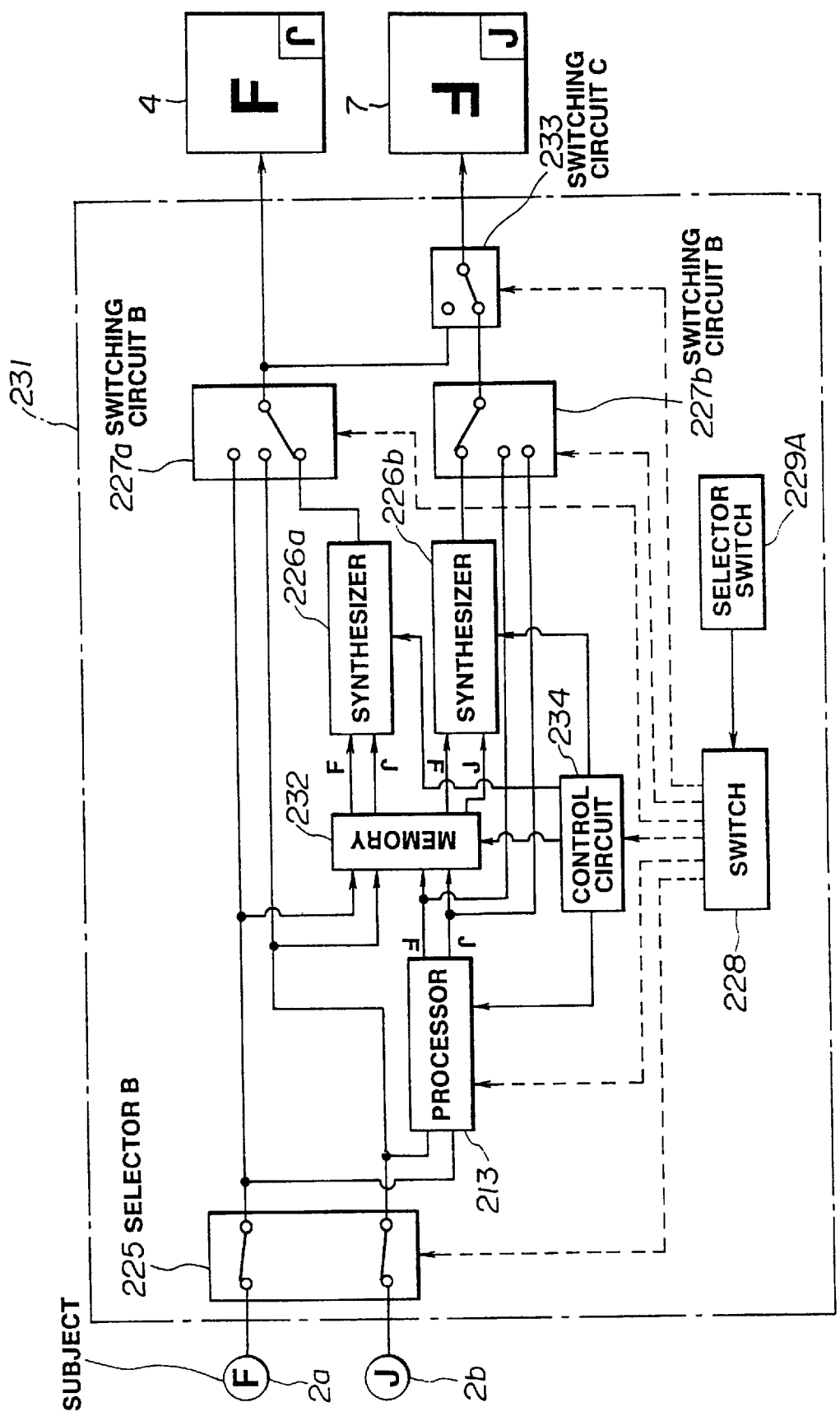
FIGS. 55 and 56 relate to the twenty-fourth embodiment of the present invention.

FIG. 55 shows an example of circuitry of an image processing apparatus 231 of this embodiment.

Figure 56:
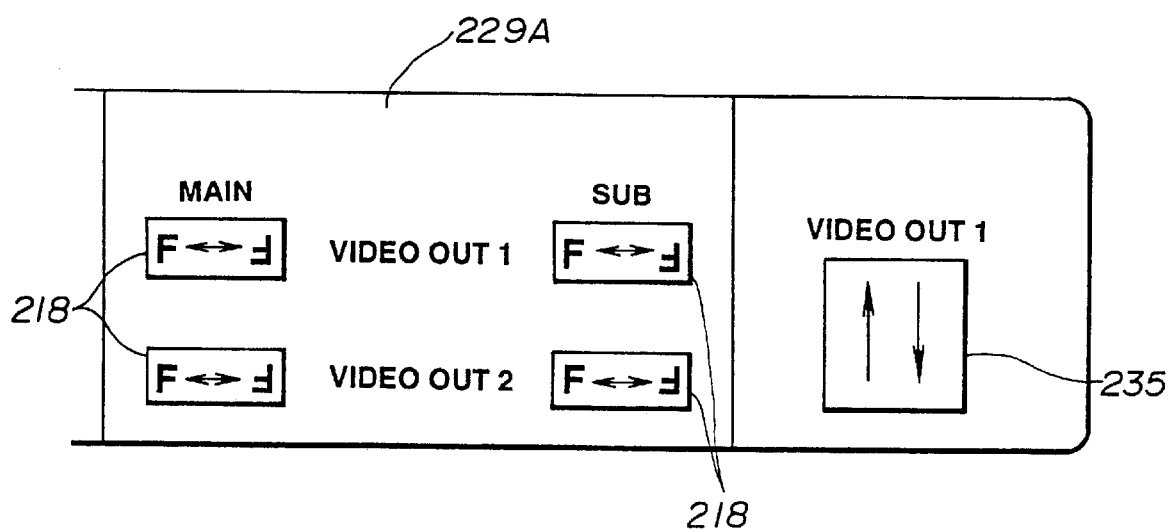

In the image processing apparatus 231, the processor 213 is succeeded by a memory 232 for temporarily storing video signals, a switching circuit C 233 for selecting a video signal to be displayed on the second monitor 7, and a control circuit 234 for controlling the processor 213, memory 232, and synthesizers 226a and 226b. The switching circuit C 233 selects an output of the switching circuit B 227a or 227b and supplies the selected output to the second monitor 7. The switch 228 shown in FIG. 55 controls the switching circuit C 233 and control circuit 234. A selector switch 229A shown in FIG. 56 has the same components as those of the selector switch 229 and further includes an image inversion switch 235 for automatically producing an inverted image of an image represented by a video signal of Video Out 1; that is, an image to be displayed on the first monitor 4 and displaying the inverted image on the second monitor 7.

In the foregoing configuration, as described in conjunction with FIG. 52 showing the twenty-third embodiment, when an inverted image of an image appearing on the first monitor 4 viewed by the surgeon A is displayed on the second monitor 7 viewed by the surgeon B, the surgeon B would find it more helpful. The image processing apparatus 231 therefore has the circuitry shown in FIG. 55.

Selected video signals representing raw images of F and J are processed by the processor 213. Processed video signals representing inverted images are stored in the memory 232. For displaying a synthetic image on the first monitor 4, the control circuit 235 issues a control signal to each of the memory 232 and synthesizer 226a. A resultant synthetic image signal is then supplied to the first monitor 4 via the switching circuit B 227a.

For displaying an image on the second monitor 7, the video signals representing the F and J images and having been supplied from the memory 232 to the synthesizer 226*a* are image-wise inverted vertically and laterally. Inverted video signals are then sent to the synthesizer 227*b*. Thus, a synthetic inverted image signal is produced. At this time, when the image inversion switch 235 in the selector switch 229A is pressed, the synthetic inverted image signal is selected by the switching circuit C 233. An inverted image of a whole image appearing on the first monitor 4 shown in FIG. 55 is displayed automatically. When the image inversion switch 235 is pressed again, the switching circuit C 233 is switched over to an output stage of the switching circuit B 227*a*. The same image as that appearing on the first monitor 4 is then displayed.

This embodiment enables the surgeon B to have a desired view, of which right and left hands are consistent with those of the surgeon B, on the second monitor 7 with ease. Furthermore, even if the image on the first monitor 4 is changed, the second monitor can visualize either a unique image or the same image as the one appearing on the first monitor 4.

Next, the twenty-fifth embodiment will be described.

Figure 57:
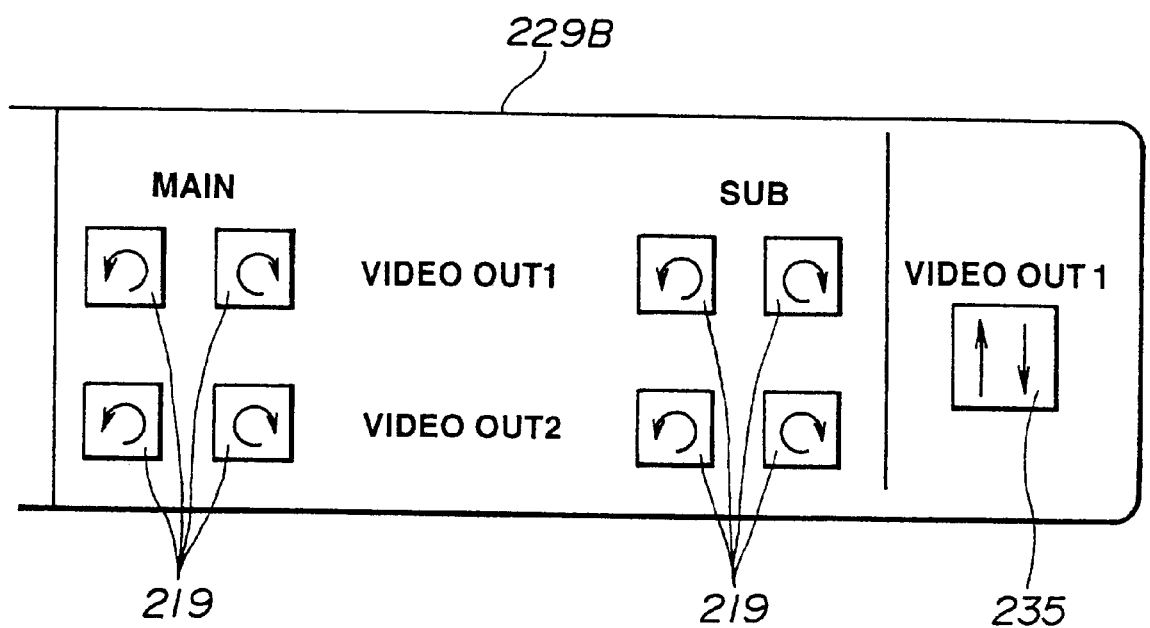
FIGS. 57 and 58 relate to the twenty-fifth embodiment of the present invention.

The twenty-fifth embodiment is substantially identical to the twenty-fourth embodiment. A difference lies in that the selector switch 229A in the twenty-fourth embodiment (See FIG. 56) has four inverted image switches 218, while a selector switch 229B in this embodiment includes, as shown in FIG. 57, a turn switch 219. In response to an instruction issued from the turn switch 219, the processor 213 turns an image. The other components are identical to those of the twenty-fourth embodiment.

Figure 58:
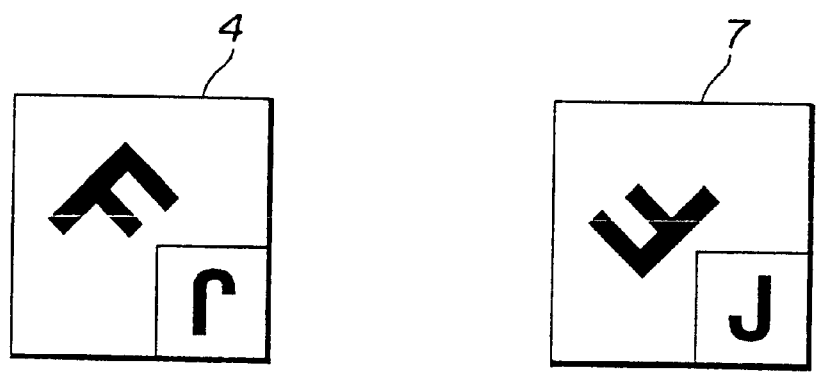

FIG. 58 shows examples of displays on the first monitor 4 and second monitor 7 in the situation shown in FIG. 52, wherein the endoscope 2*a* is turned right and an F image is tilted accordingly.

In the state shown in FIG. 58, for returning the F image on the first monitor 4 to an original angle, the turn switch 219 on the left hand of Video Out 1 in the selector switch 229B is pressed. The F image then turns counterclockwise so as to return to an erect image. At this time, when the image inversion switch 235 in the selector switch 229B has been pressed, as described in conjunction with the twenty-fourth embodiment, an inverted image made by inverting the F image appearing on the first monitor 4 is automatically displayed on the second monitor 7. The image on the second monitor 7 is therefore also returned to an original angle. The same applies to an J image provided by the endoscope 2*b*.

As mentioned above, this embodiment employs the turn switch 219 and image inversion switch 235. When an image on a monitor is turned with the turn of the endoscope 2*a* or 2*b*, if only the image on the first monitor 4 is returned to an original angle, the image on the second monitor 7 is also returned to the original angle. Surgeons can proceed with a surgical procedure smoothly without a trouble.

Next, the twenty-sixth embodiment will be described.

Figure 59:
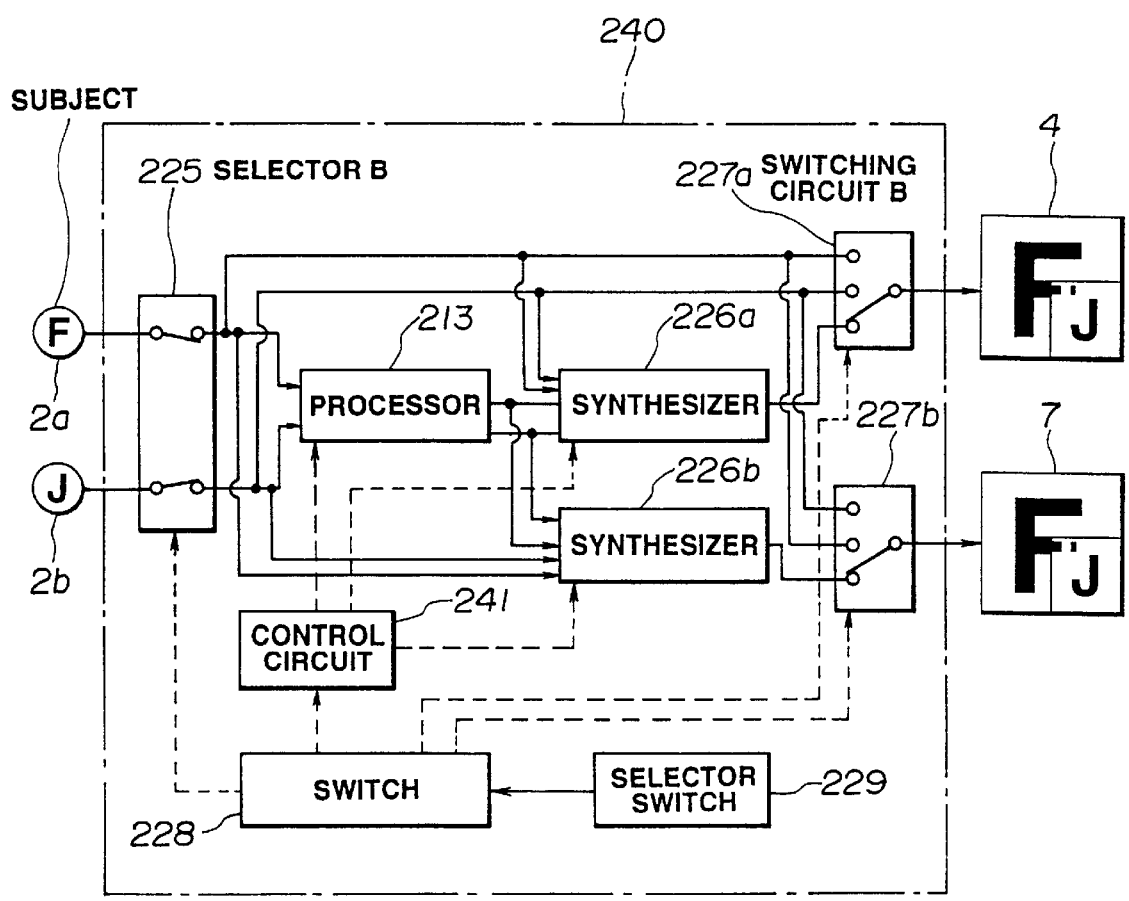
FIGS. 59 and 60J relate to the twenty-sixth embodiment of the present invention.

The twenty-sixth embodiment is substantially identical to the twenty-third embodiment. A difference lies in that, as shown in FIG. 59, an image processing apparatus 240 of this embodiment has a control circuit 241 installed in the stage succeeding the switch 228. The other components are identical to those of the twenty-third embodiment.

Figure 60:
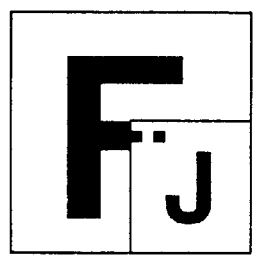
FIG. 60A is the first explanatory diagram showing an example of a display on a monitor provided by the image processing apparatus shown in FIG. 59.
FIG. 60B is the second explanatory diagram showing an example of a display on a monitor provided by the image processing apparatus shown in FIG. 59.
FIG. 60C is the third explanatory diagram showing an example of a display on a monitor provided by the image processing apparatus shown in FIG. 59.
FIG. 60D is the fourth explanatory diagram showing an example of a display on a monitor provided by the image processing apparatus shown in FIG. 59.
FIG. 60E is the fifth explanatory diagram showing an example of a display on a monitor provided by the image processing apparatus shown in FIG. 59.
FIG. 60F is the sixth explanatory diagram showing an example of a display on a monitor provided by the image processing apparatus shown in FIG. 59.
FIG. 60G is the seventh explanatory diagram showing an example of a display on a monitor provided by the image processing apparatus shown in FIG. 59.
FIG. 60H is the eighth explanatory diagram showing an example of a display on a monitor provided by the image processing apparatus shown in FIG. 59.
FIG. 60I is the ninth explanatory diagram showing an example of a display on a monitor provided by the image processing apparatus shown in FIG. 59.
Figure 60:
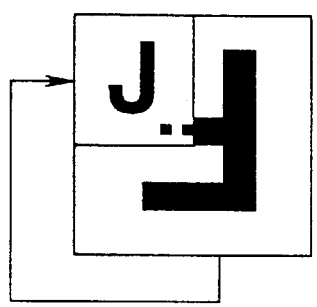
Figure 60:
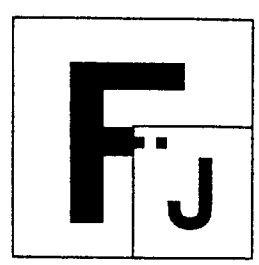
Figure 60:
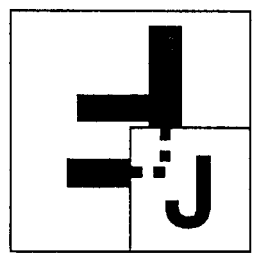
Figure 60:
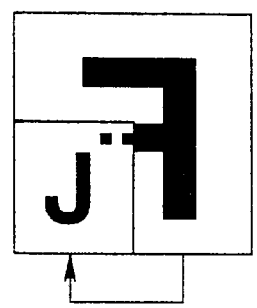
Figure 60:
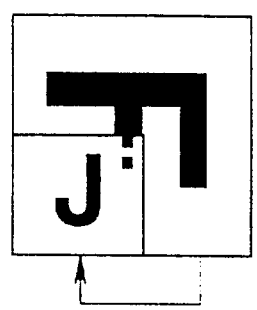
Figure 60:
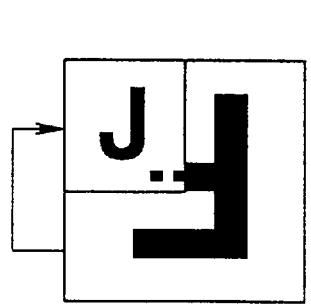
Figure 60:
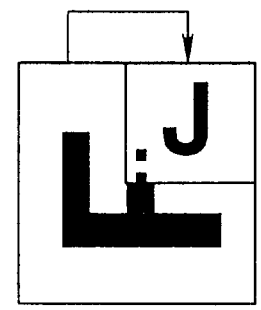
Figure 60:
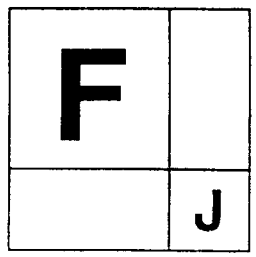
Figure 60:
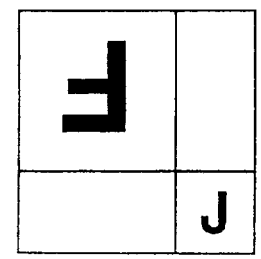

FIGS. 60A and 60B show examples of displays on monitors, wherein the image processing apparatus 240 of this embodiment has inverted an F image for the second monitor 7 and shifted a sub image for the second monitor 7. FIGS. 60D and 60D show examples of displays on monitors, wherein the image processing apparatus 230 of the twenty-third embodiment has inverted an F image for the second monitor 7.

The modes of operation of this embodiment having the foregoing configuration will be described in conjunction with FIGS. 52, 54, 59, and 60A to 60J.

In the situation shown in FIG. 52, when an erect image of F is displayed on the second monitor 7 as shown in FIG. 59, the surgeon B finds it vertically and laterally inverse. The F image should therefore be inverted. The Main inverted image switch 218 of Video Out 2 in the selector switch 229 shown in FIG. 54 is pressed, whereby a signal is transmitted to each of the switch 228, control circuit 241, and synthesizer 226*b* in the image processing apparatus 240 shown in FIG. 59. The F image on the second monitor 7 is then inverted.

At this time, the control circuit 241 sends a control signal to the synthesizer 226*b* so that a sub image is shifted diagonally, or in this example, from the right lower corner of the monitor to the left upper corner thereof. As a result, an image shown in FIG. 60B appears on the second monitor 7.

When the image processing apparatus 230 of the twenty-third embodiment is used, if the F image on the second monitor 7 is inverted, since the control circuit 241 is not included, a sub image is not shifted. Consequently, an image shown in FIG. 60D appears on the second monitor 7.

FIG. 60B is compared with FIG. 60D. A main image appearing on the second monitor 7 as shown in FIG. 60B is identical to a main image appearing on the first monitor 4 as shown in FIG. 60A (a dotted portion of an F image serving as a main image that is a portion of the F image masked by a sub image is identical to an associated portion of the other F image). The surgeons A and B can therefore observe the same portion of F. In case of the image processing apparatus 230 of the twenty-third embodiment, as shown in FIGS. 60D and 60C, a dotted portion of an F image serving as a main image or a portion of the F image masked by a sub image is different from the one of the other F image. The surgeons A and B therefore observe different portions of F. In other words, when the image processing apparatus 240 of this embodiment is used, the same range of F is visualized on each of the first monitor 4 and second monitor 7.

Similarly to the display of an inverted image, a mirror image can be displayed. In FIG. 60E, the F image on the second monitor 7 has been laterally inverted in order to produce a mirror image, and the sub image has been shifted to a symmetric position. In FIGS. 60F to 60H, the F image serving as a main image has been turned clockwise in units of 90° and the sub image has also been turned clockwise in units of 90°. In FIGS. 60E to 60H, the sub image has been shifted for the same purpose as that mentioned in conjunction with FIG. 60B; that is, for visualizing the same range of F on each of the first monitor 4 and second monitor 7.

For displaying an inverted image, a mirror image, or a turned image, as mentioned above, a sub image is shifted. When F appears as an erect image on the second monitor 7, a shifted sub image is returned to the original position.

As mentioned above, according to the present embodiment, even when an F image serving as a main image on either of monitors is inverted, the same range of F can be visualized as a main image for both the surgeon A viewing the first monitor 4 and the surgeon B viewing the second monitor 7. The surgeons A and B can therefore proceed with a surgical procedure smoothly. In particular, when a surgical procedure is conducted under endoscopic observation, since a surgeon manipulates an endoscope and another surgeon manipulates a therapeutic appliance while observing a lesion on a monitor, it is a must that two monitors visualize the same range of a subject.

When the displays as those shown in FIGS. 60C and 60D appear, if the endoscope is moved so that the F image is shifted to the left upper corner of the first monitor 4 and thus parted from the sub image, the F image on the second monitor 7 approaches the sub image located at the right lower corner. This phenomenon does not occur in this embodiment. Optimal images can be displayed all the time.

In this embodiment, image compositions are as shown in FIGS. 60A, 60B, 60E, and 60F to 60H. Image compositions shown in FIGS. 60I and 60J may be adopted as variants.

Specifically, when the F image on the second monitor 7 is inverted by pressing the Main inverted image switch 218 of Video Out 2 shown in FIG. 54, the control circuit 241 shown in FIG. 59 allows each of the synthesizers 226a and 226b to execute image construction, and sends a control signal instructing production of a multi-image to each of the synthesizers 226a and 226b. Consequently, images shown in FIG. 60I and 60J are displayed on the monitors.

As long as these multi-images are concerned, even when the F image on the second monitor 7 is inverted, the whole of the F image is displayed on each of the first monitor 4 and second monitor 7. The image composition of this variant is concerned with an inverted image. Alternatively, a multi-image including a mirror image or a turned image can be constructed.

In this variant, even when the F image on one of monitors is inverted, the whole of the F image appears on each of the monitors. The F image serving as a main image will not be masked by a sub image, thus ensuring smooth proceeding of a surgical procedure. Even when the F image is to be displayed as a mirror image or a turned image but not as an inverted image, since the control circuit 241 should only issue a control signal instructing each of the synthesizers 226a and 226b to produce a multi-image, software can be programmed readily.

A multi-image composition may be adopted even in normal operation mode. In this case, there is a problem that the F image serving as a main image appear small. In this variant, therefore, unless the inverted image switch 218 is pressed, a multi-image is not produced.

Next, the twenty-seventh embodiment will be described.

FIG. 61 shows an operation room, in which a surgical procedure is in progress under endoscopic observation, from above. Surgeons A and B who are assisted by nurses A and B have inserted therapeutic appliances 304 and 305 and a first rigid endoscope 306a into a patient's body cavity using trocars and cannulas 301, 302, and 303, having pierced the wall of the body cavity.. A TV camera 307 is connected to the first endoscope 306a (hereinafter, the first endoscope 306a to which the TV camera 307 is connected will be referred to as merely the first endoscope 306a). A video signal sent from the TV camera 307 is fed to and processed by an image synthesizing display unit 308 serving as an image processing apparatus, and then displayed on each of first and second TV monitors 309 and 310 and recorded in a VTR 311.

The first TV monitor 309 is viewed mainly by the surgeon A, while the second TV monitor 310 is viewed mainly by the surgeon B.

Image input means connectable to the image synthesizing display unit 308 include not only the first endoscope 306a but also an image recording/reproducing apparatus 312 having a capability of a printer to record or reproduce an endoscopic image on or from, for example, a magneto-optical disk, and a second endoscope 306b to which a TV camera is connected and which will be described later. The image synthesizing display unit 308 synthesizes images supplied from the first and second endoscopes 306a and 306b and the image recording/reproducing apparatus 312 (for example, one image is used as a main image and another image is used as a sub image, and a synthetic image is constructed as a picture-in-picture image having the main image and sub image), and then displays the synthetic image on each of the first and second TV monitors 309 and 310 and records the image on the VTR 311.

The first embodiment 306a is connected to a light source unit 314 via a light guide cable 313 and thus supplied illumination light. An image provided by the first endoscope 306a is sent to the image synthesizing display unit 308. The image synthesizing display unit 308 produces a video signal in which the image provided by the first endoscope 306a is synthesized with an image supplied from the image recording/reproducing apparatus 312, and sends the video signal to each of the first monitor 309 and second monitor 310 for visualization.

The surgeon A holds the first endoscope 306a and therapeutic appliance 305 and proceeds with a surgical procedure while viewing the first TV monitor 309. The surgeon B holds the therapeutic appliance 304, and when needed, the second endoscope 306b with a TV camera, which will be described later, and proceeds with the surgical procedure while viewing the second monitor 310.

As shown in FIG. 62, the image synthesizing display unit 308 comprises A/D converters 321a, 321b, and 321c for converting video signals sent from the first and second endoscopes 306a and 306b and the image recording/reproducing appliance 312 into digital forms, an input selector 322 that is stationed in the output stage of the A/D converters 321a, 321b, and 321c and selects two of signals sent from the A/D converters 321a, 321b, and 321c, a synthesizer 323 for producing a synthetic image constructed as a picture-in-picture image using the video signals selected by the input selector 322, an output selector 324 for selecting a raw image that has not been synthesized with any other image or a synthetic image supplied from the synthesizer 323, a D/A converter 325 for converting an output signal of the output selector 324 into an analog form, a CPU 326 for controlling the input selector 322, output selector 324, and synthesizer 323, and an operation panel 327 for use in instructing the CPU 326 to pass control.

The operation panel 327 is, as shown in FIG. 63, composed of Select switches 331a and 331b for use in selecting a video signal for a main image of a synthetic image, a Select indicator 332 for indicating a number of an input means from which a selected video signal is supplied, Select switches 333a and 333b for use in selecting a video signal for a sub image, a Select indicator 334 for indicating a number of an input means from which a selected video signal is supplied, and an Ins/Del switch 335 for determining whether a synthetic image should be produced.

Next, the modes of operation of an endoscope system having the foregoing system configuration will be described. Input means connected to the image synthesizing display unit 308 are assigned identification numbers. For example, the first endoscope 306a is assigned identification number 1, the second endoscope 306b is assigned identification number 2, and the image recording/reproducing apparatus 312 is assigned identification number 3. By designating an identification number, an input means is selected at the operation panel 327. Endoscopic images of a lesion in a patient's body cavity produced before treatment are recorded in advance as still and animated images in the image recording/reproducing apparatus 312.

The first endoscope 306a is used to produce a current endoscopic image of the lesion in the patient's body cavity. For displaying the image on each of the first and second TV monitors 309 and 310, first, identification number 1 of the first endoscope 306a is selected using the Select switches 331a and 331b on the operation panel 327. At this time, 1 appears in the Select indicator 332. With an instruction entered at the operation panel 327, the CPU 326 issues a control signal so that the input selector 322 is switched over to the output stage of the first endoscope 306a, and thus selects a video signal sent from the first endoscope 306a. The CPU 326 controls the output selector 324, so that an input video signal is converted into an analog form by the D/A converter 325 and supplied as an animated image to the first monitor 309, second monitor 310, and VTR 311 as shown in FIG. 64A.

The same applies to the case in which a current endoscopic image of the lesion in the patient's body cavity is produced by manipulating the second endoscope 306b designated with the identification number entered using the Select switches 333a and 333b, and then displayed on each of the first and second TV monitors 309 and 310. Another case to which the foregoing modes of operation apply is such that: an animated image of an endoscopic image rendering a lesion is retrieved from the image recording/reproducing apparatus 312 and displayed on each of the first and second TV monitors 309 and 310. A still image of an endoscopic image rendering the lesion may be retrieved from the image recording/reproducing apparatus 312, and, as shown in FIG. 64B, supplied as a still image to each of the first and second TV monitors 309 and 310 and the VTR 311.

Next, assume that a synthetic image is to be produced using a current endoscopic image of a lesion in a patient's body cavity produced by the first endoscope 306a as a main image and a still image of an endoscopic image of the lesion retrieved from the image recording/reproducing apparatus 312 as a sub image. For example, identification number 1 indicating the first endoscope 306a is designated using the Select switches 331a and 331b for a main image on the operation panel 327. "1" then appears in the Select indicator 332. Thereafter, identification number 3 indicating the image recording/reproducing apparatus 312 is designated using the Select switches 333a and 333b for a sub image on the operation panel 327. "3" then appears in the Select indicator 334. The Ins/Del switch 335 is then turned on, whereby the CPU 326 issues a control signal so as to control the input selector 322. An image provided by the first endoscope 306a is then supplied as a main image to the synthesizer 323, and a still image retrieved from the image recording/reproducing apparatus 312 is supplied as a sub image to the synthesizer 323. Under the control of the CPU 326, the synthesizer 323 produces a synthetic image constructed as a picture-in-picture image using the image provided by the first endoscope 306a as a main image and the still image retrieved from the image recording/reproducing apparatus 312 as a sub image, and then supplies the synthetic image to the output selector 324. Under the control of the CPU 326, the output selector 324 is switched over to the output stage of the synthesizer 323. The synthetic image signal is then converted into an analog form by the D/A converter 325, and then, as shown in FIG. 64C, displayed as a synthetic image on each of the first and second TV monitors 309 and 310 as well as the VTR 311.

Even when the second endoscope 306b is used in place of the first endoscope 306a, if only identification number 2 indicating the second endoscope 306b should be designated using the Select switches 331a and 331b for a main image on the operation panel 327, the foregoing modes of operation are executed. No mention will therefore be made of them. When a still image retrieved from the image recording/reproducing apparatus 312 is used as a main image and an image provided by the first endoscope 306a or second endoscope 306b is used as a sub image, if only the identification numbers should be designated using the Select switches 331a and 331b for a main image and the Select switches 333a and 333b for a sub image, a synthetic image having a still image as a main image and an animated image as a sub image can be produced as shown in FIG. 64D. When either an animated image retrieved from the image recording/reproducing apparatus 312 or an image provided by the first endoscope 306a or second endoscope 306b is used as a main image and an animated image that is not selected as a main image is used as a sub image, a synthetic image having animated images as a main image and a sub image can be produced as shown in FIG. 64E.

Next, when a first still image retrieved from the image recording/reproducing apparatus 312 is used as a main image and a second still image retrieved from the image recording/reproducing apparatus 312 is used as a sub image, identification number 3 indicating the image recording/reproducing apparatus 312 is designated using the Select switches 313a and 313b for a main image on the operation panel 327 so that the image recording/reproducing apparatus 312 will supply the first still image. "3" then appears in the Select indicator 332. Thereafter, identification number 3 indicating the image recording/reproducing apparatus 312 is designated using the Select switches 333a and 333b for a sub image on the operation panel 327. "3" then appears in the Select indicator 334. When the same kind of images are used as a main image and a sub image, the synthesizer 323 stores the first still image retrieved from the image recording/reproducing apparatus 312 as a main image in a frame memory that is not shown. Thereafter, the image recording/reproducing apparatus 312 is operated in order to supply the second still image. Moreover, the Ins/Del switch 335 is turned on. The synthesizer 323 then produces a synthetic image having the first still image as a main image and the second still image as a sub image. Thus, a synthetic image having still images as a main image and a sub image can be produced as shown in FIG. 64F.

As mentioned above, according to the image synthesizing display unit 308 of this embodiment, as shown in FIGS. 64A to 64F, any of synthetic images of various compositions can be produced readily merely by inputting a plurality of video signals and then selecting any of the input video signals. Image information required for conducting a surgical procedure under endoscopic observation can therefore be made available in a variety of forms.

The image recording/reproducing apparatus 312 is included in order to record or reproduce an image on or from a magneto-optical disk. The present invention is not limited to this system configuration but can also apply to a system configuration including a hard disk drive or a VTR and will still have the same advantage.

Next, the twenty-eighth embodiment will be described.

The twenty-eighth embodiment is substantially identical to the twenty-seventh embodiment. Different components alone will be described. Identical components will be assigned the same reference numerals, of which no mention will be made.

An image synthesizing display unit 308a of the twenty-eighth embodiment comprises, as shown in FIG. 65, a switching circuit 341 made up of a main image selection switch 441a for selecting a main image that is an output of the input selector 322 and a sub image selection switch 341b for selecting a sub image, and an inverting circuit 342 for inverting a main image and a sub image that are supplied from the input selector 322 and selected by the switching circuit 341, and then supplying inverted images to the synthesizer 323. An operation panel 327a in the twenty-eighth embodiment has, as shown in FIG. 66, the same components as those of the operation panel 327 in the twenty-seventh embodiment, and further includes inversion switches 351 and 352 for use in instructing inversion of a main image and a sub image. The other components are identical to those of the twenty-seventh embodiment.

Next, the modes of operation of the image synthesizing display unit 308a of the twenty-eighth embodiment having the foregoing components will be described.

For displaying an inverted image as a main image, the inversion switch 351 for inverting a main image on the operation panel 327a is pressed. The main image selection switch 341a in the switching circuit 341 is switched over to the inverting circuit 342 in response to a control signal sent from the CPU 326. An inverted image inverted by the inverting circuit 342 as shown in FIG. 67A is supplied from the image synthesizing display unit 308a through the output selector 324 and D/A converter 325. When the inversion switch 351 is pressed again, the display image is returned to a raw image.

For inverting a synthetic image, the Select switches 331a and 331b for a main image and the Select switches 333a and 333b for a sub image are used to designate a main image and a sub image in the same manner as that in the twenty-seventh embodiment. The Ins/Del switch 335 is then turned on. At this time, when the inversion switch 351 for inverting a main image is pressed, the main image selection switch 341a in the switching circuit 341 is switched over to the inverting circuit 342 in response to a control signal sent from the CPU 326. After inverted by the inverting circuit 342, the main image is supplied to the synthesizer 323. The synthesizer 323 produces a synthetic image using the main image inverted by the inverting circuit 342 and a sub image fed as a raw image via the sub image selection switch 341b. A synthetic image having an inverted image as a main image and a raw image as a sub image, as shown in FIG. 67B, is supplied from the image synthesizing display unit 308a through the output selector 324 and D/A converter 325. When the inversion switch 351 is pressed again, the main image is returned to a raw image.

An inverted image is usable as a sub image only when a synthetic image is selected. When the Ins/Del switch 335 on the operation panel 327a is pressed and the sub image inversion switch 352 is pressed, the sub image selection switch 341b in the switching circuit 341 is switched over to the inverting circuit 342. Inversion is then executed. An inverted image is then supplied to the synthesizer 323. The synthesizer 323 produces a synthetic image using a main image and a sub image that are inverted by the inverting circuit 342. A synthetic image that looks as shown in FIG. 67C or 67D depending on the setting of the main image is supplied from the image synthesizing display unit 8a through the output selector 324 and D/A converter 325. When the inversion switch 352 is pressed again, the sub image is returned to a raw image.

The other modes of operation are identical to those of the twenty-seventh embodiment.

As mentioned above, the image synthesizing display unit 308a has the same advantage as the twenty-seventh embodiment does. Furthermore, an inverted image of an image produced by an endoscope lying on the opposite side of a surgeon during a surgical procedure can be displayed on a monitor. The surgeon can therefore manipulate a therapeutic appliance without any sense of unnaturalness. In particular, when a still image recorded in the image recording/reproducing apparatus 312 is derived from the opposed endoscope, if an inverted image of the still image is displayed on the monitor, the surgeon finds the image helpful in identifying a lesion being treated. This results in improved operability.

Next, the twenty-ninth embodiment will be described. The twenty-ninth embodiment is substantially identical to the twenty-seventh embodiment. Different components alone will be described. Identical components will be assigned the same reference numerals, of which no mention will be made.

An image synthesizing display unit 308b of the twenty-ninth embodiment has, as shown in FIG. 68, the same components as those of the first embodiment and further includes an image memory 361 in the stage preceding the synthesizer 323. An operation panel 327b in the twenty-ninth embodiment is, as shown in FIG. 69A, composed of Select switches 331a and 331b for use in selecting a video signal, a Select indicator 332 for indicating a number of an input means that supplies a selected video signal, an Ins/Del switch 335 for use in determining whether a synthetic image should be produced, and a Freeze switch 371 for allowing the CPU 326 to control the image memory 361 and fetch a still image from the image memory 361. The other components are identical to those in the twenty-seventh embodiment.

The modes of operation to be effected when the Freeze switch 371 shown in FIG. 69A is not functioned are identical to those of the twenty-seventh embodiment. A mode of operation different from that of the twenty-seventh embodiment will be described.

To begin with, for displaying a still image on the first monitor 309, the Freeze switch 371 on the operation panel 327b is pressed. Video signals selected by the input selector 322 are then stored temporarily in the image memory 361. The image memory 361 retains the state until the Freeze switch 371 is pressed again. In response to a control signal sent from the CPU 326, the output selector 324 is switched over to the output stage of the image memory 361. A still image held in the image memory 361 is supplied from the image synthesizing display unit 308b. At this time, when the Freeze switch 371 is pressed, the output image is returned to an animated image.

Next, for displaying a synthetic image, the Select switches 331a and 331b on the operation panel 327b are used to designate a video signal provided by the first endoscope 306a. The Freeze switch 371 is then pressed, whereby video signals selected by the input selector 322 are temporarily stored in the image memory 361. Thereafter, when the Ins/Del switch 335 is pressed, the image memory 361 and synthesizer 323 are controlled according to a control signal sent from the CPU 326. A video signal (animated image) sent from the first endoscope 306a and selected by the input selector 322 and a still image provided by the first embodiment 306a and held in the image memory 361 are synthesized by the synthesizer 323. The output selector 325 is switched over to the output stage of the synthesizer 323, whereby a synthetic image is supplied from the image synthesizing display unit 308b. At this time, when the Freeze switch 371 on the operation panel 327b is pressed, the image provided by the first endoscope 306a is stored in the image memory 361. A synthetic image having an animated image and a latest still images, which are provided by the first endoscope 306a, as the one shown in FIG. 70A or 70B is supplied from the image synthesizing display unit 308b.

An image composition shown in FIG. 70C or 70D is also available, wherein an animated image provided by the first endoscope 306a and a still image provided by the second endoscope 306b are synthesized. For another image composition shown in FIG. 70E or 70F, a still image provided by the first endoscope 306a and an animated image provided by the second endoscope 306b are synthesized. For realizing these image compositions, an operation panel 327c shown in FIG. 69B is employed. The operation panel 327c has the same composition as those of the operation panel 327 (See FIG. 63) in the twenty-seventh embodiment and further includes the Freeze switch 371. By pressing the Freeze switch 371, a video signal sent from an input means and designated for a sub image is temporarily stored in the image memory 361, and then synthesized with a main image by the synthesizer 323.

According to the image synthesizing display unit 308b of this embodiment, unlike that of the twenty-seventh or twenty-eighth embodiment, a still image rendering a lesion need not be stored in advance in the image recording/reproducing apparatus 312 but a still image rendering a lesion that has not been treated can be produced readily. Moreover, a synthetic image composed of an animated image and a still image rendering a lesion that has not been treated can be displayed during treatment. Furthermore, a still image rendering a lesion that is being treated can be fetched readily. The progress of treatment can therefore be grasped easily. Since any of synthetic images of various compositions can be produced readily at the operation panel, image information required for a conducting surgical procedure under endoscopic observation can be offered in a variety of forms.

Next, the thirtieth embodiment will be described. The thirtieth embodiment is substantially identical to the twenty-ninth embodiment. Different components alone will be described. Identical components will be assigned the same reference numerals, of which no mention will be made.

As shown in FIG. 71, an output selector 324a in an image synthesizing display unit 308c of the thirtieth embodiment includes selection switches 381, 382, and 383 for selecting an output image for the first and second TV monitors 309 and 310 as well as the VTR 311 which serve as display means. An operation panel 327d in the thirtieth embodiment is, as shown in FIG. 72, similarly to the one in the twenty-ninth embodiment, composed of an Ins/Del switch 335 for use in determining whether a synthetic image should be produced, a Freeze switch 371 for allowing the CPU 326 to control the image memory 361 and fetch a still image, a main image setting switch 391 for use in designating a main image, a sub image setting switch 392 for use in designating a sub image, and mode setting switches 393, 394, and 395 for specifying an image composition for the first and second TV monitors 309 and 310 and the VTR 311 respectively. By pressing the main image setting switch 391 and sub image setting switch 392 repeatedly, input means are changed continuously. A designated input means is indicated in an indicator 96 composed of, for example, LEDs. The other components are identical to those in the twenty-ninth embodiment.

For example, for displaying an animated image, which is a raw image provided by the first endoscope 306a and has not been processed, on the first TV monitor 309, as shown in FIG. 72, the main image setting switch 391 is used to designate the first endoscope 306a. The mode setting switch 393 is set to the neutral position. The CPU 326 then issues a control signal. With the control signal, the selection switch 381 for the first TV monitor 309 in the output selector 324a is switched over to the output stage of the input selector 322 in order to select an animated image signal. The animated signal is then displayed on the first TV monitor 309.

Likewise, for displaying a still image provided by the first endoscope 6a on the second TV monitor 310, the main image setting switch 391 is used to designate the first endoscope 306a. The mode setting switch 394 is set to the still mode position. Next, the Freeze switch 371 is pressed. Thus, a video signal sent from the first endoscope 306a and selected by the input selector 322 is temporarily stored in the image memory 361. With a control signal sent from the CPU 326, the selection switch for the second TV monitor 310 in the output selector 324a is switched over to the output stage of the image memory 361 in order to select a still image signal. A still image is then displayed on the second TV monitor 310.

For displaying a synthetic image, for example, for recording a synthetic image, which has an animated image provided by the first endoscope 306a as a main image and a still image provided by the second endoscope 306b as a sub image, in the VTR 311, the main image setting switch 391 is used to designate the first endoscope 306a and the sub image setting switch 392 is used to designate the second endoscope 306b. The mode setting switch 394 is set to the still mode position. The Freeze switch 371 is then pressed. A video signal sent from the second endoscope 306b and selected by the input selector 322 is temporarily stored in the image memory 361. A synthetic image having an animated image provided by the first endoscope 306a as a main image and a still image provided by the second endoscope 306b as a sub image is then produced. In response to a control signal sent from the CPU 326, the selection switch for the second TV monitor 310 in the output selector 324a is switched over to the output stage of the synthesizer 323 in order to select a synthetic image signal. Consequently, a synthetic image having the animated image provided by the first endoscope 306a as a main image and the still image provided by the second endoscope 306b is supplied to the VTR 311.

The other combinations of kinds of images can be specified at the operation panel 327d in the same manner as mentioned above, of which no mention will be made.

As mentioned above, according to the image synthesizing display unit 308c of this embodiment, a composition of an output image can be specified for each of the first and second TV monitor 309 and 310 and the VTR 311 which serve as image output means. In addition to the advantage of the twenty-ninth embodiment, this embodiment has the advantage that since a synthetic image can be produced in any of various compositions depending on a purpose of an output means, image information required for conducting a surgical procedure under endoscopic observation can be offered in a variety of forms.

That is to say, a conventional endoscope system described in, for example, Japanese Patent Application No.5-334585 is configured so that each of a plurality of output means can selectively display a raw image and a processed image. However, an image composition cannot be designated for each output means. When a processed image such as a synthetic image is selected, the same synthetic image is supplied to each of all output means including a TV monitor and a VTR. For displaying a synthetic image on the TV monitor and recording a raw image on tape in the VTR, an output signal of a TV camera must be supplied as an input signal to the VTR and an output signal of an image processing apparatus must be supplied as an input signal to the TV monitor. This embodiment has resolved this problem.

Similarly to the thirtieth embodiment, even the twenty-seventh or twenty-eighth embodiment can be configured so that an output image composition can be specified for each of the first and second TV monitors 309 and 310 and the VTR 311 which serve as image output means. This configuration provides the same advantage as that described previously.

In the twenty-seventh to thirtieth embodiments, the number of image output means is three; the first and second TV monitors 309 and 310 and the VTR 311. The number of image output means is not limited to three. Each of the twenty-seventh to thirtieth embodiments can be configured so that an image is displayed on one or more output means. This configuration still have the same advantage as that described previously.

The output means for recording an image has been described as a VTR. Alternatively, the output means for recording an image may be a magneto-optical disk drive, a WORM or phase change type optical disk drive, a hard disk drive, or a DAT unit.

In the twenty-seventh to thirtieth embodiments, the first and second embodiments 306a and 306b serving as image input means are rigid endoscopes with TV cameras. Alternatively, an electronic endoscope having a solid-state imaging device such as a CCD at the distal end thereof will do. The present invention is not limited to these rigid endoscopes but also applies to flexible endoscopes. The present invention is not restricted to medical endoscopes but also applies to industrial endoscopes. Even for these applications, the present invention still has the same advantages as those described previously.

Next, the thirty-first embodiment will be described.

As shown in FIG. 73, an image processing apparatus 451 of the thirty-first embodiment further comprises an enlarging circuit 452 for enlarging an image provided by an image inverting circuit 419 and a moving circuit 453 for moving an image enlarged by the enlarging circuit. A synthesizer 417 produces a picture-in-picture image having images handled by the enlarging circuit 452 and moving circuit 453 as a main image and a sub image. A selector switch 421a selects a normal image provided by a selector switch 421b or a picture-in-picture image.

The selector switch 421a is designed to select a main image of a picture-in-picture image, a sub image of a picture-in-picture image, or a normal image.

A selector 422 in the thirty-first embodiment further includes a zoom ratio knob 455 for use in designating a zoom ratio at which the enlarging circuit 52 enlarges an image (for example, 1.0, 1.1, or 1.2 times) and a move button 456 for use in instructing the moving circuit 453 to move a main image. A normal image knob 425a, a picture-in-picture main image knob 425b, or a picture-in-picture sub image knob 425c is set to an image signal position A, B, C, or D, thus selecting a main Image of a picture-in-picture image, a sub image of a picture-in-picture image, or a normal image.

Next, the modes of operation of this embodiment will be described.

In the image processing apparatus 451, assume that a picture-in-picture image, which is composed of a main image represented by an image signal D and a sub image represented by an image signal B, and a normal image represented by an image signal C are to be supplied by means of the selector switch 421b. In this case, the normal image knob 425a is set to C, the picture-in-picture main image knob 425b is set to D, and the picture-in-picture sub image knob 425c is set to B. Thus, the image signals D, B, and C are selected, and supplied to an output channel for a picture-in-picture image composed of a main image and a sub image and to an output channel for a normal image.

Next, a selection knob 426a in the selector circuit 422 is set to a picture-in-picture mode position in order to select a picture-in-picture image. Selection knobs 426b and 426c are set to normal mode positions in order to select a normal image. Thus, a picture-in-picture image (synthetic image) and a normal image are supplied.

As a result, the image signal C is supplied as a normal image. A picture-in-picture image (synthetic image) composed of a main image represented by the image signal D and a sub image represented by the image signal B is supplied as shown in FIG. 74A.

As shown in FIG. 74A, when the main image D is vignetted by the sub image B, the main image is moved. For zooming in the main image at the ratio of 1.2 times in order to make the main image easy-to-see, the zoom ratio knob 55 in the selector 422 is set to the 1.2 position. The enlarging circuit 452 then enlarges the main image (FIG. 74B). When the move button 456 is pressed, the moving circuit 453 moves the main image in the screen (FIG. 74C).

As mentioned above, according to the image processing apparatus 451 of this embodiment, the enlarging circuit 52 enlarges a main image at a zoom ratio designated with the zoom ratio knob 455 in the selector 422. When the move button 456 is pressed, the moving circuit 453 moves the main image. Thus, even when a main image is vignetted by a sub image, the main image can be enlarged without causing a desired portion to be vignetted. Such an image suitable for observation can be displayed efficiently.

The selector 422 selects any of image signals A, B, C, and D. The present invention is not limited to this mode of operation. Alternatively, a plurality of picture-in-picture images may be produced using a plurality of image signals or a plurality of normal images may be selected.

The number of output channels is three. Alternatively, needless to say, a plurality of output channels may be included.

The enlarging circuit 452 and moving circuit 453 are included. Alternatively, either of them may be included. Even in this configuration, the advantage of the enlarging circuit 452 or moving circuit 453 can be made available.

The present invention is not limited to the field of endoscopy.

In the present invention, it will be apparent that a wide range of different embodiments can be formed on the basis of the present invention without departing from the spirit and scope of the invention. This invention is limited to the accompanying claims but not restricted to any specific embodiments.

What is claimed is:

1. An image processing system, comprising:
   an image means for imaging a subject to produce raw images;
   an image input means for inputting said raw images produced by said image means;
   an image processing means for processing said raw images fed to said image input means to produce at least one kind of transformed image consisting of a turned image or a mirror image;

a synthetic image producing means for synthesizing at least two images among said raw images and a plurality of transformed images which are different from one another and which are produced by said image processing means so as to produce a first synthetic image while producing a second synthetic image which is different from said first synthetic image;

an image output means having a first image output unit for outputting said first synthetic image and a second image output unit for outputting said second synthetic image;

a first display means for displaying images supplied from said first image output unit; and a second display means separate from said first display means for displaying images supplied from said second image output unit.

2. An image processing system according to claim 1, wherein each of the first and second synthetic images produced by the synthetic image producing means includes at least a first image area and a second image area, and wherein the synthetic image producing means produces a plurality of the synthetic images by allocating first and second different images from among both the transformed image and the raw images to the first image area and the second image area, respectively.

3. An image processing system according to claim 2, wherein the first image area is a main image area in a picture-in-picture image, and the second image area is a sub-image area in the picture-in-picture image.

4. An image processing system according to claim 2, wherein the image processing means includes an image data transforming means for transforming image data of the first image area by enlarging, reducing, or moving the first different image to be allocated to the first image area.

5. An image processing system according to claim 4, wherein the image data transforming means transforms image data of the first image area by enlarging, reducing, or moving the first different image to be allocated to the first image area according to a display position of the second different image to be allocated to the second image area in the first different image to be allocated to the first image area.

6. An image processing system according to claim 2, further comprising a second image display position setting means for setting a display position of the second different image to be allocated to the second image area in the first different image to be allocated to the first image area.

7. An image processing system according to claim 6, wherein the second image display position setting means sets the display position of the second different image to be allocated to the second image area in the first different image to be allocated to the first image area according to the first different image to be allocated to the first image area.

8. An image processing apparatus, comprising:

a first image input means for inputting raw images;

a second image input means for inputting raw images different from the raw images fed to the first image input means;

an image processing means for processing at least one raw image among the raw images from the first and second image input means to produce at least one kind of transformed image;

a synthetic image producing means for synthesizing at least two images from among the raw images and at least one transformed images produced by the image processing means so as to produce at least a first synthetic image and a second synthetic image;

a first image output unit for outputting the first synthetic image produced by the synthetic image producing means to a first monitor; and a second image output unit for outputting the second synthetic image signal produced by the synthetic image producing means to a second monitor separate from the first monitor.

9. An image processing apparatus according to claim 8, wherein each of the first and second synthetic images produced by the synthetic image producing means includes at least a first image area and a second image area, and wherein the synthetic image producing means produces a plurality of synthetic images by allocating different images from among both the transformed image and the raw images to the first and second image areas.

10. An image processing apparatus according to claim 9, wherein the first image area is a main image area in a picture-in-picture image, and the second image area is a sub-image area in a picture-in-picture image.

11. An image processing apparatus according to claim 10, wherein the image processing means includes a main image transforming means for transforming a main image by enlarging, reducing, or moving one of the different images to be allocated to the main image area.

12. An image processing apparatus according to claim 11, wherein the main image transforming means transforms the main image by enlarging, reducing, or moving the one of the different images to be allocated to the main image area according to a display position of another of the different images to be allocated to the sub-image area in the one of different images to be allocated to the main image area.

13. An image processing apparatus according to claim 10, further comprising a sub-image display position setting means for setting a display position of another of the different images to be allocated to the sub-image area in one of the different images to be allocated to the main image area.

14. An image processing apparatus according to claim 12, wherein the sub-image display position setting means sets a display position of the another of the different images to be allocated to the sub-image area in the one of the different images to be allocated to the main image area according to one of the different images to be allocated to the main image area.

15. An image processing apparatus according to claim 8, wherein the image processing means produces at least one turned image or mirror image as the transformed image.

16. An image processing apparatus according to claim 15, further comprising a turn value setting means for setting a quality of turn for the at least one turned image to be produced by the image processing means.

17. An image processing apparatus according to claim 8, further comprising a character data generating means for generating at least state character data indicating a state of the first and second synthetic images supplied from the first and second image output unit, and a character superposing means for superposing state character data generated by the character data generating means on the first and second synthetic images supplied from the first and second image output unit.

18. An image processing apparatus according to claim 17, further comprising a character superposition time setting means for setting a time interval during which the state character data is superposed by the character superposing means.

19. An image processing apparatus according to claim 8, wherein the transformed image includes at least one of a turned image and a mirror image produced by the processing means so as to produce the first synthetic image while producing the second synthetic image which is different from the first synthetic image.

20. An image processing apparatus according to claim 19, wherein the turned image is made by turning a raw image 180°.

21. An image processing apparatus according to claim 8, wherein the raw images are still and animated images.

22. An image processing apparatus according to claim 8, wherein the raw images are endoscopic images.

23. An endoscope image processing system, comprising:

a first image input means for inputting raw images from an endoscope which is inserted into a lumen to image a subject to produce raw images;

a second image input means for inputting raw images different from said raw images fed to said first image input means;

an image processing means for processing at least one raw image among the raw images from said first and second image input means to produce at least one kind of transformed image consisting of a turned image or a mirror image;

a synthetic image producing means from synthesizing at least two images among said raw images and transformed images produced by said image processing means;

an image output means for outputting images synthesized by said synthetic image producing means;

a first display means for displaying one of said images synthesized by said synthetic image producing means and outputted from said image output means; and a second display means for displaying another one of said images synthesized by said synthetic image producing means and outputted from said image output means, said second display means being separate from said first display means.

* * * * *